United States Patent
Nguyen et al.

(10) Patent No.: US 11,793,531 B2
(45) Date of Patent: Oct. 24, 2023

(54) AXIAL LENGTHENING THROMBUS CAPTURE SYSTEM, TENSIONING SYSTEM AND EXPANDABLE FUNNEL CATHETER

(71) Applicant: Vascular Medcure, Inc., Anaheim, CA (US)

(72) Inventors: Thanh Van Nguyen, Anaheim, CA (US); Rajan Hansji, Anaheim, CA (US); Duy Nguyen, Anaheim, CA (US)

(73) Assignee: Vascular Medcure, Inc., Anaheim, CA (US)

( * ) Notice: Subject to any disclaimer, the term of this patent is extended or adjusted under 35 U.S.C. 154(b) by 0 days.

(21) Appl. No.: 17/090,330

(22) Filed: Nov. 5, 2020

(65) Prior Publication Data

US 2021/0128185 A1 May 6, 2021

Related U.S. Application Data

(60) Provisional application No. 63/064,289, filed on Aug. 11, 2020, provisional application No. 62/930,990, filed on Nov. 5, 2019.

(51) Int. Cl.
*A61B 17/221* (2006.01)
*A61B 17/22* (2006.01)
*A61B 17/00* (2006.01)

(52) U.S. Cl.
CPC .. *A61B 17/221* (2013.01); *A61B 2017/00871* (2013.01); *A61B 2017/2212* (2013.01); *A61B 2017/22038* (2013.01)

(58) Field of Classification Search
CPC .......... A61B 17/221; A61B 2017/2212; A61B 2017/2215; A61B 2017/2217;
(Continued)

(56) References Cited

U.S. PATENT DOCUMENTS 3,506,011 A 4/1970 Silverman
5,011,488 A 4/1991 Ginsburg
(Continued)

FOREIGN PATENT DOCUMENTS

CN 102036611 4/2011
CN 103284775 A 9/2013
(Continued)

OTHER PUBLICATIONS

US 8,668,714 B2, 03/2014, Cully et al. (withdrawn)
(Continued)

*Primary Examiner* — Kankindi Rwego
(74) *Attorney, Agent, or Firm* — Shumaker & Sieffert, P.A.

(57) ABSTRACT

Systems and methods can remove material of interest, including blood clots, from a body region, including but not limited to the circulatory system for the treatment of pulmonary embolism, deep vein thrombosis, cerebrovascular embolism, and other vascular occlusions. The capture system can include a tubular body comprising a first end, a second end, and an axial length therebetween, the first end having an opening and a capture guide. The capture system can include one or more tensioners coupled to the capture guide. The tubular body has a first configuration in which the first end and the capture guide are expanded while the second end and a majority of the tubular body remains compressed. The tubular body is transformable to a second configuration by application of tension by the tensioners. The catheter can remove a large volume of clot.

30 Claims, 32 Drawing Sheets

(58) Field of Classification Search
CPC .... A61B 17/22031; A61B 2017/22034; A61B 2017/22035; A61B 2017/22038; A61B 2017/22039; A61B 2017/22041; A61B 17/320016; A61B 17/32056; A61B 17/3207; A61B 17/320758; A61B 2017/320064; A61B 2017/320716; A61B 2017/320766; A61B 2017/320775; A61B 2017/00867; A61B 2017/00871
USPC ........................................................ 606/200
See application file for complete search history.

(56) References Cited

U.S. PATENT DOCUMENTS

| | | |
|---|---|---|
| 5,102,415 A | 4/1992 | Guenther et al. |
| 5,135,484 A | 8/1992 | Wright |
| 5,846,251 A | 12/1998 | Hart |
| 5,868,708 A | 2/1999 | Hart |
| 5,895,398 A | 4/1999 | Wensel et al. |
| 5,935,139 A | 8/1999 | Bates |
| 5,947,985 A | 9/1999 | Imran |
| 6,066,149 A | 5/2000 | Samson et al. |
| 6,126,635 A | 10/2000 | Simpson et al. |
| 6,165,196 A | 12/2000 | Stack et al. |
| 6,179,859 B1 | 1/2001 | Bates et al. |
| 6,210,370 B1 | 4/2001 | Chi-Sing et al. |
| 6,221,006 B1 | 4/2001 | Dubrul et al. |
| 6,264,663 B1 | 7/2001 | Cano |
| 6,270,477 B1 | 8/2001 | Bagaoisan et al. |
| 6,391,044 B1 | 5/2002 | Yadav et al. |
| 6,432,122 B1 | 8/2002 | Gilson et al. |
| 6,569,181 B1 | 5/2003 | Burns |
| 6,605,102 B1 | 8/2003 | Mazzocchi et al. |
| 6,620,182 B1 | 9/2003 | Khosravi et al. |
| 6,635,070 B2 | 10/2003 | Leeflang et al. |
| 6,645,224 B2 | 11/2003 | Gilson et al. |
| 6,663,650 B2 | 12/2003 | Sepetka et al. |
| 6,824,545 B2 | 11/2004 | Sepetka et al. |
| 6,840,950 B2 | 1/2005 | Stanford et al. |
| 6,887,256 B2 | 5/2005 | Gilson et al. |
| 6,945,977 B2 | 9/2005 | Demarais et al. |
| 7,094,249 B1 | 8/2006 | Broome et al. |
| 7,220,271 B2 | 5/2007 | Clubb et al. |
| 7,232,432 B2 | 6/2007 | Fulton et al. |
| 7,491,210 B2 | 2/2009 | Dubrul et al. |
| 7,621,870 B2 | 11/2009 | Berrada et al. |
| 7,662,165 B2 | 2/2010 | Gilson et al. |
| 7,766,921 B2 | 8/2010 | Sepetka et al. |
| 7,780,696 B2 | 8/2010 | Daniel et al. |
| 7,785,342 B2 | 8/2010 | Gilson et al. |
| 7,901,426 B2 | 3/2011 | Gilson et al. |
| 8,070,769 B2 | 12/2011 | Broome |
| 8,092,486 B2 | 1/2012 | Berrada et al. |
| 8,236,024 B2 | 8/2012 | Stanford et al. |
| 8,252,017 B2 | 8/2012 | Paul, Jr. et al. |
| 8,255,193 B2 | 8/2012 | Humphrey et al. |
| 8,298,252 B2 | 10/2012 | Krolik et al. |
| 8,313,503 B2 | 11/2012 | Cully et al. |
| 8,337,520 B2 | 12/2012 | Cully et al. |
| 8,388,644 B2 | 3/2013 | Parker |
| 8,444,661 B2 | 5/2013 | Nair et al. |
| 8,460,335 B2 | 6/2013 | Carpenter |
| 8,475,487 B2 | 7/2013 | Bonnette et al. |
| 8,491,623 B2 | 7/2013 | Vogel et al. |
| 8,545,526 B2 | 10/2013 | Martin et al. |
| 8,613,717 B2 | 12/2013 | Aklog et al. |
| 8,657,849 B2 | 2/2014 | Parker |
| 8,696,622 B2 | 4/2014 | Fiorella |
| 8,734,374 B2 | 5/2014 | Aklog et al. |
| 8,771,289 B2 | 7/2014 | Mohiuddin et al. |
| 8,777,976 B2 | 7/2014 | Brady et al. |
| 8,795,305 B2 | 8/2014 | Martin et al. |
| 8,795,322 B2 | 8/2014 | Cully et al. |
| 8,801,748 B2 | 8/2014 | Martin |
| 8,864,792 B2 | 10/2014 | Eckhouse et al. |
| 8,919,389 B2 | 12/2014 | Gries |
| 8,926,642 B2 | 1/2015 | Nelson |
| 8,932,319 B2 | 1/2015 | Martin et al. |
| 8,948,848 B2 | 2/2015 | Merhi |
| 8,956,384 B2 | 2/2015 | Berrada et al. |
| 8,968,330 B2 | 3/2015 | Rosenbluth et al. |
| 8,998,944 B2 | 4/2015 | Thornton |
| 9,254,371 B2 | 2/2016 | Martin et al. |
| 9,283,066 B2 | 3/2016 | Hopkins et al. |
| 9,301,769 B2 | 4/2016 | Brady et al. |
| 9,308,007 B2 | 4/2016 | Cully et al. |
| 9,358,022 B2 | 6/2016 | Morsi |
| 9,408,620 B2 | 8/2016 | Rosenbluth et al. |
| 9,427,244 B2 | 8/2016 | Lund-Clausen et al. |
| 9,463,036 B2 | 10/2016 | Brady et al. |
| 9,526,864 B2 | 12/2016 | Quick |
| 9,579,116 B1 | 2/2017 | Nguyen et al. |
| 9,636,206 B2 | 5/2017 | Nguyen et al. |
| 9,655,633 B2 | 5/2017 | Leynov et al. |
| 9,744,024 B2 | 8/2017 | Nguyen et al. |
| 9,844,386 B2 | 12/2017 | Nguyen et al. |
| 9,931,495 B2 | 4/2018 | Aboytes |
| 9,999,493 B2 | 6/2018 | Nguyen et al. |
| 10,045,790 B2 | 8/2018 | Cox et al. |
| 10,070,879 B2 | 9/2018 | Nguyen et al. |
| 10,143,482 B2 | 12/2018 | Nguyen et al. |
| 10,238,482 B2 | 3/2019 | Nguyen et al. |
| 10,292,723 B2 | 5/2019 | Brady |
| 10,314,600 B2 | 6/2019 | Morsi |
| 10,376,275 B2 | 8/2019 | Nguyen et al. |
| 10,383,751 B2 | 8/2019 | Ferrera et al. |
| 10,456,236 B2 | 10/2019 | Nguyen et al. |
| 10,512,479 B2 | 12/2019 | Nguyen et al. |
| 10,687,834 B2 | 6/2020 | Follmer et al. |
| 11,259,824 B2 | 3/2022 | Brady et al. |
| 11,278,307 B2 | 3/2022 | Bruzzi et al. |
| 2002/0095171 A1* | 7/2002 | Belef .......................... 606/200 |
| 2002/0169474 A1 | 11/2002 | Kusleika et al. |
| 2003/0176884 A1 | 9/2003 | Berrada et al. |
| 2003/0216770 A1 | 11/2003 | Persidsky et al. |
| 2004/0039411 A1 | 2/2004 | Gilson et al. |
| 2004/0073198 A1 | 4/2004 | Gilson et al. |
| 2004/0087971 A1 | 5/2004 | Arnott |
| 2004/0098025 A1 | 5/2004 | Sepetka et al. |
| 2004/0098033 A1 | 5/2004 | Leeflang et al. |
| 2005/0085826 A1 | 4/2005 | Nair et al. |
| 2005/0228417 A1 | 10/2005 | Teitelbaum et al. |
| 2006/0025804 A1 | 2/2006 | Krolik et al. |
| 2006/0155305 A1 | 7/2006 | Freudenthal et al. |
| 2006/0212062 A1 | 9/2006 | Farascioni |
| 2007/0010702 A1 | 1/2007 | Wang et al. |
| 2007/0088382 A1 | 4/2007 | Bei et al. |
| 2007/0093744 A1 | 4/2007 | Elmaleh |
| 2007/0112374 A1 | 5/2007 | Paul et al. |
| 2007/0282303 A1 | 12/2007 | Nash et al. |
| 2008/0167678 A1 | 7/2008 | Morsi |
| 2009/0292307 A1 | 11/2009 | Razack |
| 2010/0211095 A1 | 8/2010 | Carpenter |
| 2010/0249815 A1 | 9/2010 | Jantzen et al. |
| 2010/0268264 A1 | 10/2010 | Bonnette et al. |
| 2011/0125181 A1 | 5/2011 | Brady et al. |
| 2011/0166586 A1 | 7/2011 | Sepetka et al. |
| 2012/0172915 A1 | 7/2012 | Fifer et al. |
| 2012/0172916 A1 | 7/2012 | Fifer et al. |
| 2012/0197285 A1 | 8/2012 | Martin et al. |
| 2012/0271403 A1 | 10/2012 | Gries |
| 2012/0310251 A1 | 12/2012 | Sepetka et al. |
| 2012/0330346 A1 | 12/2012 | Frimerman |
| 2012/0330350 A1 | 12/2012 | Jones et al. |
| 2013/0102996 A1 | 4/2013 | Strauss |
| 2013/0178891 A1 | 7/2013 | Russell et al. |
| 2013/0184738 A1 | 7/2013 | Laroya et al. |
| 2013/0184741 A1 | 7/2013 | Laroya et al. |
| 2013/0197567 A1 | 8/2013 | Brady et al. |
| 2013/0238009 A9 | 9/2013 | Hopkins et al. |
| 2013/0267993 A1 | 10/2013 | Carpenter |
| 2013/0338703 A1 | 12/2013 | Hansen et al. |
| 2014/0005712 A1 | 1/2014 | Martin |
| 2014/0005713 A1 | 1/2014 | Bowman |

(56) References Cited

U.S. PATENT DOCUMENTS

| | | |
|---|---|---|
| 2014/0005717 A1 | 1/2014 | Martin et al. |
| 2014/0046358 A1 | 2/2014 | Cully et al. |
| 2014/0052103 A1 | 2/2014 | Cully et al. |
| 2014/0128894 A1 | 5/2014 | Sepetka et al. |
| 2014/0249568 A1 | 9/2014 | Adams et al. |
| 2014/0249571 A1 | 9/2014 | Tsutsui et al. |
| 2014/0276403 A1 | 9/2014 | Follmer et al. |
| 2014/0276922 A1 | 9/2014 | McLain et al. |
| 2014/0277013 A1 | 9/2014 | Sepetka et al. |
| 2014/0324091 A1 | 10/2014 | Rosenbluth et al. |
| 2014/0350593 A1 | 11/2014 | Laroya et al. |
| 2014/0371781 A1 | 12/2014 | Morgan |
| 2015/0005781 A1 | 1/2015 | Lund-Clausen et al. |
| 2015/0018929 A1 | 1/2015 | Martin et al. |
| 2015/0088190 A1 | 3/2015 | Jensen |
| 2015/0196380 A1 | 7/2015 | Berrada et al. |
| 2015/0265299 A1 | 9/2015 | Cooper et al. |
| 2015/0297251 A1 | 10/2015 | Sos |
| 2015/0306311 A1 | 10/2015 | Pinchuk et al. |
| 2016/0022290 A1 | 1/2016 | Johnson et al. |
| 2016/0022291 A1 | 1/2016 | Johnson et al. |
| 2016/0038271 A1 * | 2/2016 | Johnsen et al. |
| 2016/0192953 A1 | 7/2016 | Brady |
| 2016/0235422 A1 | 8/2016 | Al-Jilaihawi et al. |
| 2016/0256180 A1 | 9/2016 | Vale et al. |
| 2017/0035445 A1 | 2/2017 | Nguyen et al. |
| 2017/0086960 A1 | 3/2017 | Nguyen et al. |
| 2017/0143359 A1 | 5/2017 | Nguyen et al. |
| 2017/0224366 A1 | 8/2017 | Nguyen et al. |
| 2017/0259042 A1 | 9/2017 | Nguyen et al. |
| 2018/0055619 A1 | 3/2018 | Nguyen et al. |
| 2018/0125512 A1 | 5/2018 | Nguyen et al. |
| 2018/0296315 A1 | 10/2018 | Nguyen et al. |
| 2018/0303499 A1 * | 10/2018 | Bonneau ................ A61B 1/307 |
| 2019/0015122 A1 | 1/2019 | Nguyen et al. |
| 2019/0099194 A1 | 4/2019 | Nguyen et al. |
| 2019/0142445 A1 | 5/2019 | Morsi |
| 2019/0216589 A1 | 7/2019 | Nguyen et al. |
| 2020/0029985 A1 | 1/2020 | Nguyen et al. |
| 2020/0197031 A1 | 6/2020 | Nguyen et al. |
| 2020/0222171 A1 | 7/2020 | Nguyen et al. |
| 2021/0128185 A1 | 5/2021 | Nguyen et al. |
| 2022/0071646 A1 | 3/2022 | Brady et al. |

FOREIGN PATENT DOCUMENTS

| | | |
|---|---|---|
| CN | 103841905 | 6/2014 |
| CN | 104042304 | 9/2014 |
| CN | 104053410 A | 9/2014 |
| CN | 104068910 A | 10/2014 |
| CN | 104168845 A | 11/2014 |
| EP | 1221307 | 7/2002 |
| JP | 2011508635 A | 3/2011 |
| JP | 2013085657 A | 5/2013 |
| JP | 2015522345 A | 8/2015 |
| WO | WO99/39648 | 8/1999 |
| WO | WO 03/077799 | 9/2003 |
| WO | WO 2006/138391 | 12/2006 |
| WO | WO 2007/047818 | 4/2007 |
| WO | WO 2008/070996 | 6/2008 |
| WO | WO 2009/055782 | 4/2009 |
| WO | WO 2009/086482 | 7/2009 |
| WO | 2014141226 A1 | 9/2014 |
| WO | WO 2015079401 | 6/2015 |
| WO | WO 2017/024258 | 2/2017 |
| WO | WO 2018/148174 | 8/2018 |
| WO | 2021092235 A1 | 5/2021 |

OTHER PUBLICATIONS

Invitation to Pay Additional Fees dated Dec. 23, 2020 in PCT/US2020/059194 in 3 pages.
PCT Search Report and Written Opinion dated Mar. 4, 2021 in PCT Application No. PCT/US2020/059194 in 20 pages.
Extended European Search Report dated Mar. 1, 2019 in EP Application No16833959.6 in 7 pages.
Notice of Allowance in U.S. Appl. No. 15/230,109 dated Oct. 17, 2016 in 7 pages.
Notice of Allowance in U.S. Appl. No. 15/376,448 dated Mar. 8, 2017 in 9 pages.
Notice of Allowance in U.S. Appl. No. 15/376,448 dated Sep. 18, 2017 in 9 pages.
Notice of Allowance in U.S. Appl. No. 15/428,076 dated Apr. 10, 2017 in 16 pages.
Notice of Allowance in U.S. Appl. No. 15/604,531 dated Feb. 7, 2018 in 8 pages.
Notice of Allowance in U.S. Appl. No. 15/687,789 dated Apr. 20, 2018 in 9 pages.
Notice of Allowance in U.S. Appl. No. 15/845,086 dated Jul. 23, 2018 in 9 pages.
Notice of Allowance in U.S. Appl. No. 16/011,251 dated Nov. 14, 2018 in 9 pages.
Notice of Allowance in U.S. Appl. No. 16/127,154 dated Mar. 29, 2019 in 11 pages.
Notice of Allowance in U.S. Appl. No. 16/207,768 dated Aug. 8, 2019 in 10 pages.
Notice of Allowance in U.S. Appl. No. 16/361,757 dated May 13, 2019 in 10 pages.
PCT Search Report and Written Opinion dated Dec. 1, 2016 in PCT Application No. PCT/US2016/045862 in 8 pages.
PCT Search Report and Written Opinion dated May 24, 2018 in PCT Application No. PCT/US2018/016976 in 10 pages.
Office Action dated May 20, 2020 in CN Application No. 201680050206.2 in 7 pages.
Extended European Search Report dated Sep. 10, 2020 in EP Application No. 20175999.0 in 9 pages.
Extended European Search Report dated Oct. 29, 2020 in EP Application No. 18751739.6 in 11 pages.

* cited by examiner

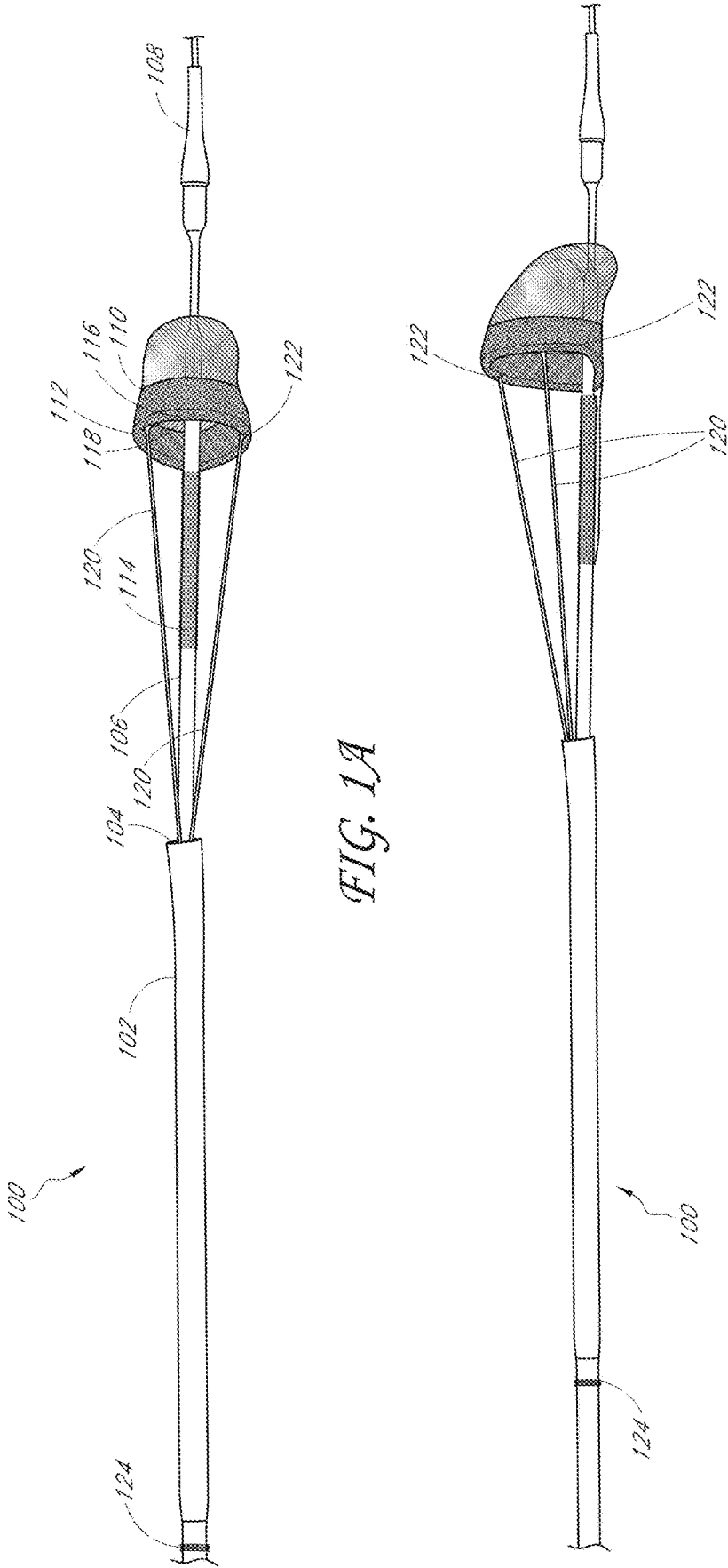

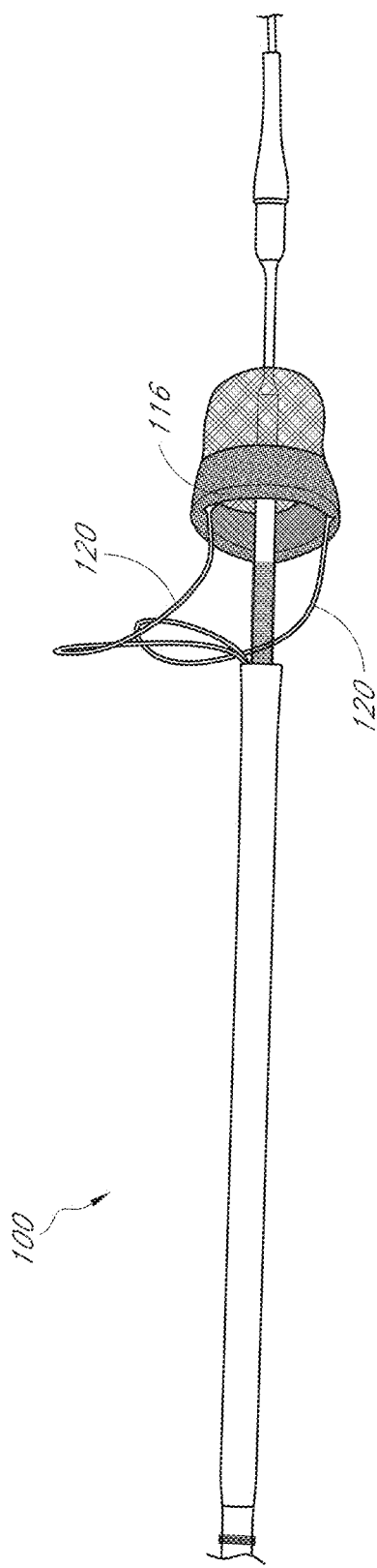
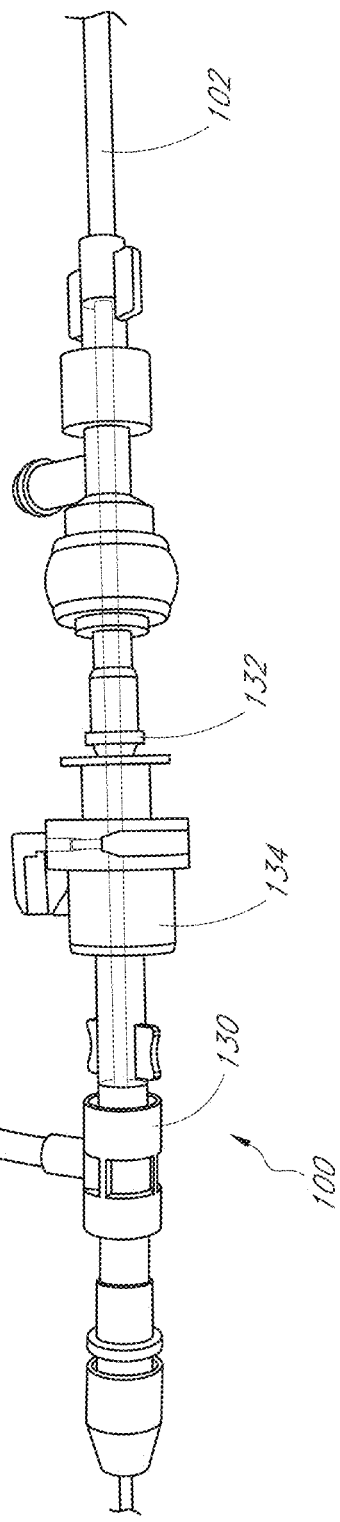
FIG. 2A
FIG. 2B

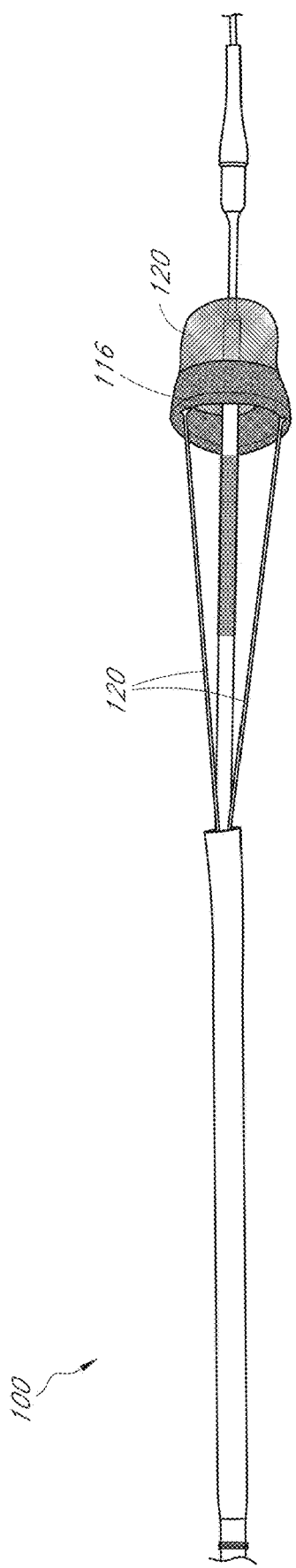
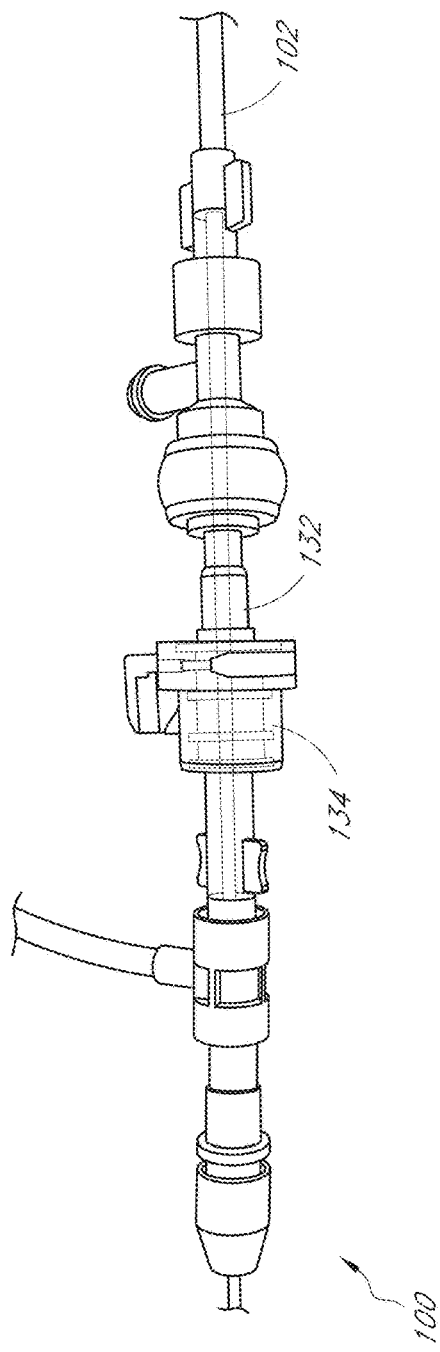
FIG. 3A
FIG. 3B

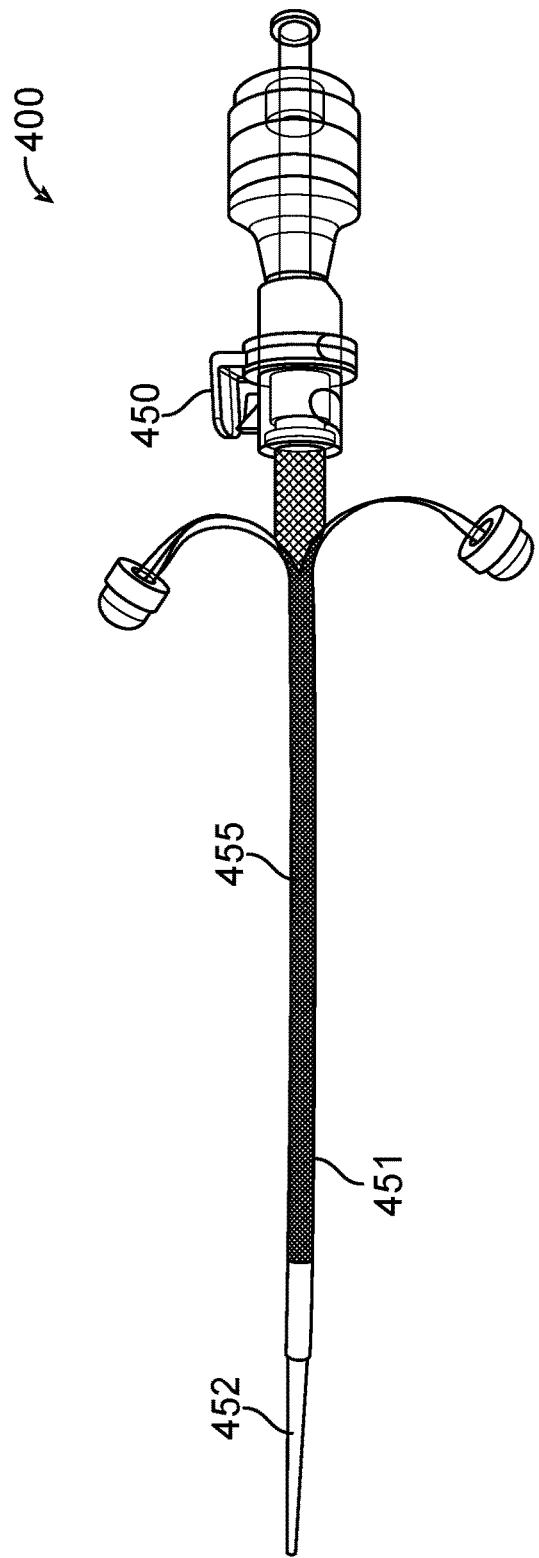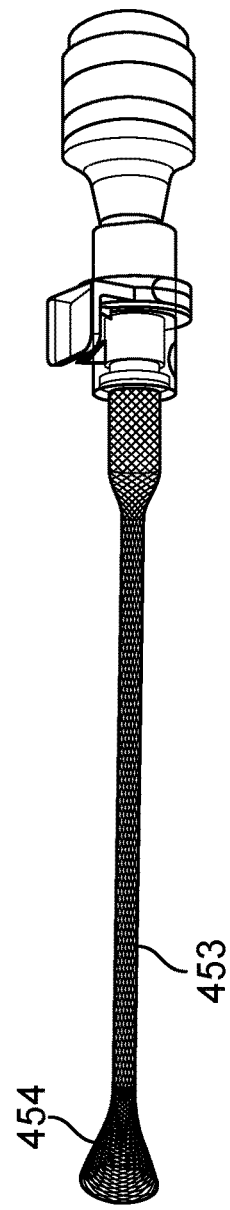
FIG. 20
FIG. 21

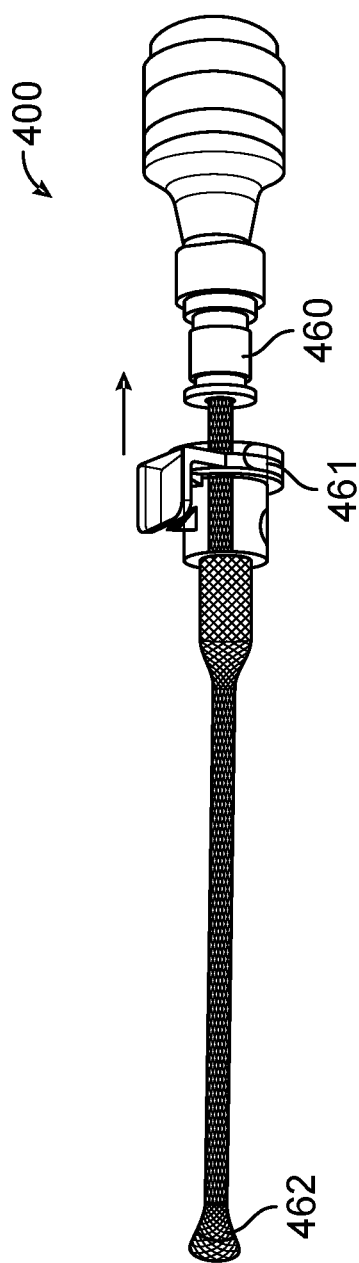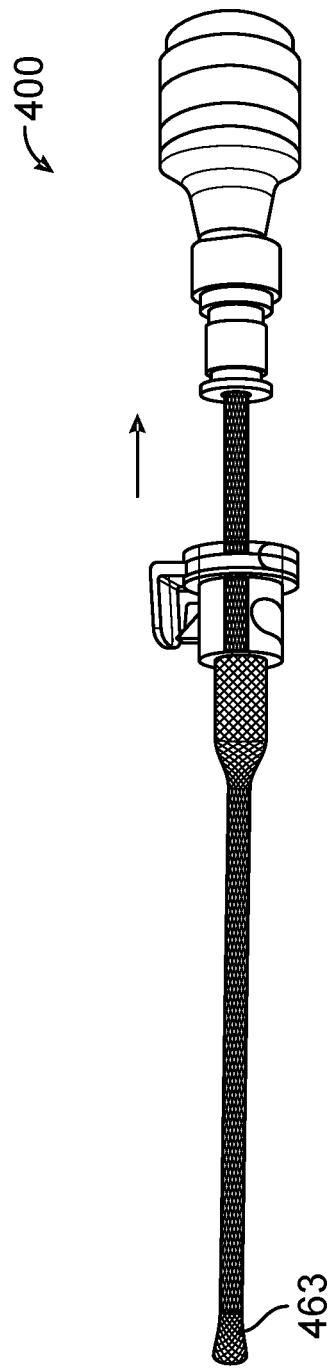
FIG. 22
FIG. 23

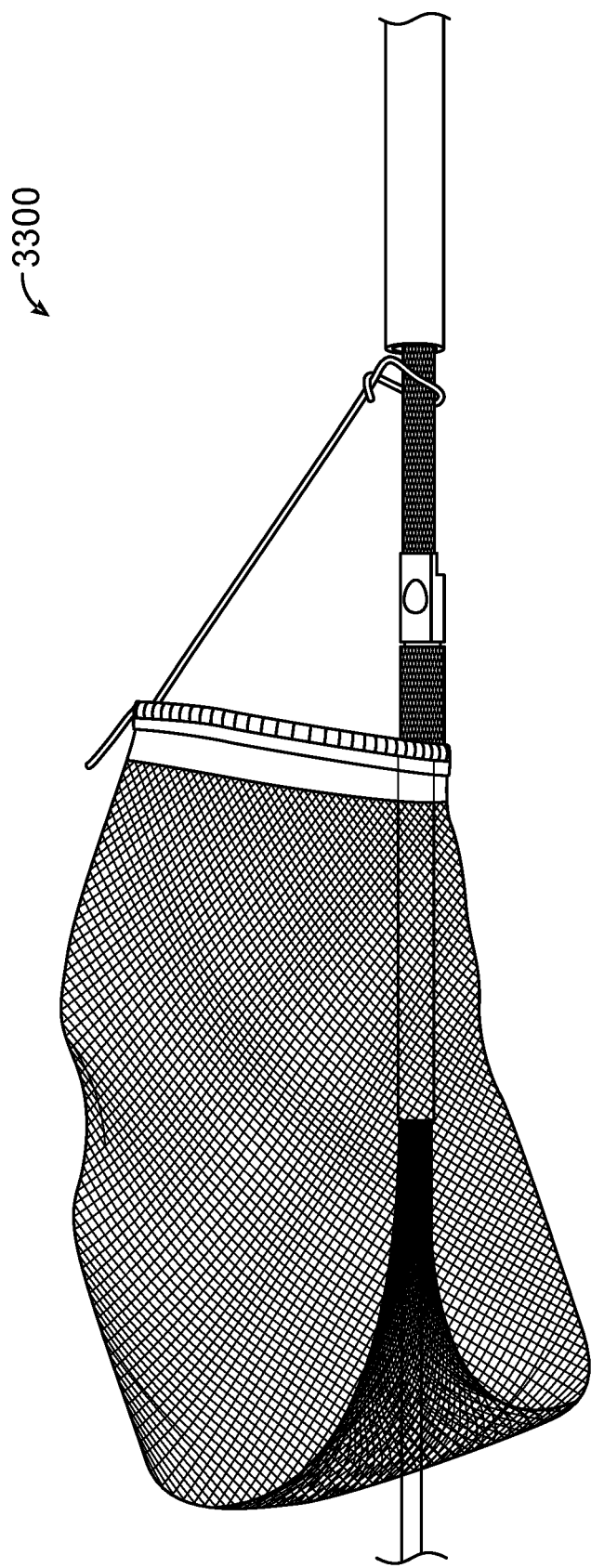

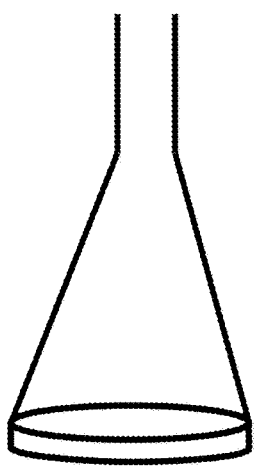
FIG. 34C
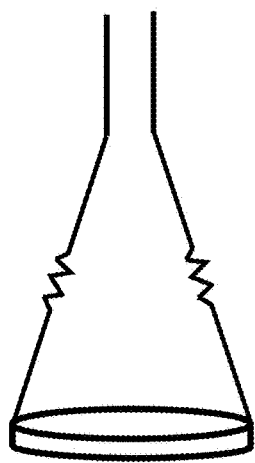
FIG. 34B
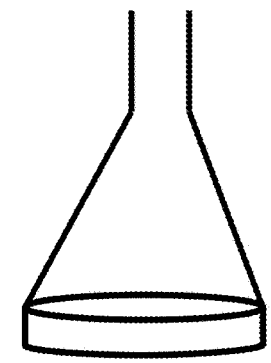
FIG. 34A
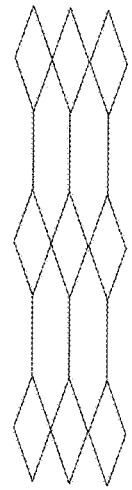
FIG. 35
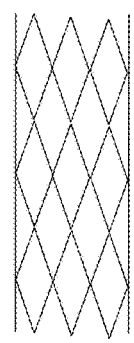
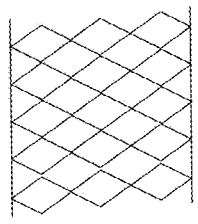

US 11,793,531 B2

AXIAL LENGTHENING THROMBUS CAPTURE SYSTEM, TENSIONING SYSTEM AND EXPANDABLE FUNNEL CATHETER

PRIORITY CLAIM

This application claims the benefit under 35 U.S.C. § 119(e) as a nonprovisional application of each of U.S. Provisional App. Nos. 62/930,990 filed on Nov. 5, 2019 and 63/064,289 filed on Aug. 11, 2020. Each of the aforementioned priority applications is hereby incorporated by reference in their entireties. This application incorporates by reference U.S. Pat. Nos. 9,579,116, 9,744,024, and 9,999,493, each of, which are hereby incorporated by reference in their entireties.

BACKGROUND

Field

The invention relates to, in some aspects, systems and methods to remove materials of interest, including blood clots, from a body region, including but not limited to the circulatory system for the treatment of pulmonary embolism (PE), deep vein thrombosis (DVT), cerebrovascular embolism, and other vascular occlusions.

Description of the Related Art

It is understood that undesirable materials such as blood clots (which could be referred to as thrombi, thromboemboli, or emboli herein) in the blood vessels may partially or completely occlude blood vessels in areas of the coronary, cerebrovascular, pulmonary, peripheral venous, and peripheral arterial circulation resulting in myocardial infarction, stroke, pulmonary embolism, deep vein thrombosis, and infarction of an extremity respectively.

Various therapies and devices are known to either dissolve, debulk and/or aspirate the emboli. For instance, anticoagulant agents such as heparin and warfarin help stabilize blood clots and prevent further forming of clots while thrombolytic agents such as urokinase, streptokinase, and tPA assist in dissolving blood clots. These agents can be delivered via systemic infusion or catheter-based infusion to the intended location. While thrombolytic agents can be effective in dissolving blood clots, they require a long time duration in order for the agents to dissolve the blood clots; thus patients may need to remain in the hospital intensive care unit (ICU) during thrombolytic infusion. Relatively long lengths of stay can increase healthcare costs significantly. A major limitation for these thrombolytic agents is that they can potentially cause intracranial, gastrointestinal, retroperitoneal, and pericardial bleeding, among other sites, which can be often life-threatening and cause significant morbidity and mortality risks.

Mechanical debulking and/or aspiration devices can be used to remove the obstruction. These mechanical techniques can either macerate, aspirate, or a combination thereof in order to remove the blood clots. An advantage of mechanical therapy is that it can remove thrombus directly from the blockage area and immediately eliminates the obstruction and may be superior to thrombolytic agents in some cases. However, current mechanical therapies have some major limitations. There is minimal to no flow during the procedure thus there is little time before patients may become hemodynamically instable. The debris removed from mechanical treatment can travel distally creating additional embolization. The small size devices are unable to remove large amount of blood clots in short time periods thus patients may become hemodynamically instable.

In some situations, the clot can be either acute, subacute and/or chronic and adhere to the vessel wall. Aspiration devices may be able to remove loose or partially adherent clot but not organized clot. Additionally, there is the potential of devices clogging at the catheter tip if the clot is more organized.

In some situations, the clot removed is highly organized and the amount of clot is substantial that makes it difficult to remove through a small catheter lumen.

Catheter-based removal of blood clots from larger blood vessels (e.g., pulmonary arteries) have had limited success compared to smaller blood vessels (e.g., coronary arteries). Catheter pulmonary embolectomy is where pulmonary emboli are removed percutaneously using several techniques. Fragmentation thrombectomy breaks blood clots into smaller pieces, most of which travel further downstream, resulting in distal embolization. It is sometimes used in combination with thrombolytics. With the rheolytic thrombectomy, high velocity saline jets create a Venturi effect and draw the fragments of the clot into the catheter. This method poses risk of hemolysis. Finally the aspiration techniques draw the clot into a catheter via suction. All of these techniques rely on the catheter used to remove the clots from blood vessels. The users use small catheters to remove or break up large amounts of blood clot. This procedure is therefore time-consuming and inefficient. Once the blood clots are broken into small pieces, the debris can migrate distally and create unwanted emboli. Rheolytic therapy poses the risk of hemolysis. Additionally, the ability to suction is limited due the small catheter size suctioning large emboli. These limitations cause in some cases unnecessary duress to the user and risk to the patient. There is a need to remove large amount of thrombus using small devices.

Catheter-based removal of blood clots in general also has a major limitation when distal working space within a body lumen is limited. Conventional devices may require full axial and/or radial deployment and expansion to be functional, and as such flexibility to use such devices for a variety of clinical situations involving differing clot or other material sizes to be removed can be very limited. Therefore, conditions where there is limited distal space of blood vessels can render these conventional devices ineffective.

It is evident that all of the therapeutic options available to patients with blood clots or other undesirable material in blood vessels and other body lumens have limitations. Anticoagulation only limits propagation of clots but does not actively remove it. Thrombolytic therapy poses a risk of major bleeding. Catheter embolectomy is not effective to manage removal of material in large vessels. Additionally, these devices require distal space to fully deploy to be functional thus ineffective in tight distal spaces. Surgical embolectomy can be highly effective but highly invasive, and has a high rate of morbidity and mortality. There is a need for a direct mechanical treatment that is as or more effective as surgical embolectomy removing large blood clots but can be performed using endovascular techniques and restore immediate blood flow, and cause a lower incidence of complications.

SUMMARY

In some embodiments, disclosed herein is a capture system for selected materials within a body. The capture system can include a capture assembly configured to isolate unwanted material, e.g., emboli, thrombi and other foreign materials from the vascular system. The capture system can be used to remove acute, subacute and chronic or organized clot. As clot or thrombus is formed and deposited on to the vessel, the acute clot rarely or minimally adheres to the vessel wall. The adherence to the vessel wall increases as the clot ages, eventually making the clot difficult to remove. Thus, a device with high resistance is needed to remove some clot formations.

The capture system can include a shape memory tubular body comprising a first end, a second end, and an axial length therebetween. The first end of the shape memory tubular body has an opening. The shape memory tubular body is transformable to a first expanded configuration in which the first end is expanded but the second end and a majority of the shape memory tubular body is compressed. The shape memory tubular body is folded between the first end and the second end. The shape memory tubular body has a first expanded axial length in the first expanded configuration. The shape memory tubular body is transformable to a second expanded configuration in which the shape memory tubular body has a second expanded axial length greater than the first expanded axial length.

Emboli, thrombi and other foreign materials can be removed from the vascular system using various method such as balloon embolectomy, basket, filter or collection bag. As the volume of clot increases, the challenge to remove through a catheter lumen is more difficult resulting in either getting stuck within the catheter lumen or unable to remove the balloon, basket, filter or collection bag from the vascular system. Thus, a device that can remove the large volume of clot is beneficial particularly if the device is expandable.

In some embodiments, a capture system is provided. The capture system can include a tubular body comprising a first end, a second end, and an axial length therebetween. The first end can include an opening and a capture guide. The capture system can include one or more tensioners coupled to the capture guide. In some embodiments, the tubular body has a first configuration in which the first end and the capture guide are expanded while the second end and a majority of the tubular body remains compressed and the tubular body has a first expanded axial length and a first width along the first expanded axial length. In some embodiments, the tubular body is transformable to a second configuration by application of tension by the tensioners, the tubular body has a second expanded axial length greater than the first expanded axial length and the tubular body has a second width along the second expanded axial length.

In some embodiments, the capture system can include a first member comprising a central lumen. In some embodiments, the capture system can include a second member disposed within the central lumen. In some embodiments, the capture guide forms the opening. In some embodiments, the one or more tensioners extend proximally from the capture guide. In some embodiments, the tubular body comprises a shape memory material. In some embodiments, a width of the shape memory body along the second expanded axial length is substantially the same as a width of the shape memory body along the first expanded axial length. In some embodiments, the one or more tensioners are equally spaced around the circumference of the capture guide. In some embodiments, the one or more tensioners are unequally spaced around the circumference of the capture guide. In some embodiments, the one or more tensioners are configured to apply tension to the capture guide such that the capture guide is rigid. In some embodiments, the one or more tensioners are rigid. In some embodiments, the one or more tensioners are flexible. In some embodiments, the one or more tensioners comprise a suture. In some embodiments, the one or more tensioners are configured to limit or prevent deflection of the capture guide. In some embodiments, the one or more tensioners comprises one or more metallic wires. In some embodiments, the one or more tensioners comprise one or more polymeric filaments. In some embodiments, the capture guide comprises a shape memory material. In some embodiments, the capture guide comprises a Nitinol loop. In some embodiments, the capture guide is configured to conform to different vessel diameters. In some embodiments, the capture guide is configured to conform to different geometric configurations.

In some embodiments, a method of retrieving a material is provided. The method can include positioning a capture system near a material. In some embodiments, the clot capture system can include a tubular body comprising a first end, a second end, and an axial length therebetween. The first end can include an opening and a capture guide. The clot capture system can include one or more tensioners coupled to the capture guide. The tubular body can have a first configuration in which the first end and the capture guide are expanded while the second end and a majority of the tubular body remains compressed. The method can include transforming the tubular body to a second configuration by application of tension by the tensioners. The tubular body can have a second expanded axial length greater than the first expanded axial length and the tubular body can have a second width along the second expanded axial length.

In some embodiments, the material comprises an emboli, thrombi, or other foreign material. In some embodiments, positioning the capture system comprises positioning a capture system within the vascular system of a patient. In some embodiments, the material is a clot adhered to a vessel wall. In some embodiments, the method can include capturing the clot by axially lengthening the tubular body. In some embodiments, the method can include removing the clot by retracting the tubular body. In some embodiments, the capture guide withstands high resistance without deflecting. In some embodiments, the capture guide conforms to the inner wall of the vessel. In some embodiments, the capture guide is held fixed by the one or more tensioners. In some embodiments, the capture guide is unable to deflect during removal of the material. In some embodiments, transforming the tubular body to a second configuration further comprises scraping the vessel wall with the capture guide. In some embodiments, the capture guide scores, scrapes, cuts, or shears the material.

In some embodiments, a catheter system is provided. The catheter system can include an expandable guide catheter comprising an expandable shaft and an expandable funnel tip. The catheter system can include a cover disposed over the expandable shaft and the expandable funnel tip. In some embodiments, the cover is configured to be removed to expand the expandable shaft and the expandable funnel tip.

In some embodiments, the expandable funnel tip comprises a dual layer structure. In some embodiments, the expandable funnel tip comprises an inner braid layer and an outer braid layer. In some embodiments, the expandable funnel tip comprises at least one coated layer. In some embodiments, the expandable shaft comprises a dual layer structure. In some embodiments, the expandable shaft comprises an inner braid layer and an outer braid layer. In some embodiments, the expandable shaft comprises at least one coated layer. In some embodiments, the catheter can include a dilator. In some embodiments, the catheter can include an obturator. In some embodiments, the expandable guide catheter comprises a braided layer. In some embodiments, the braid wire has diameter from 0.0003" to 0.030". In some embodiments, the braid pattern can be 1×1, 2×2, paired wire 1×1, paired wire 2×2, or any combination thereof. In some embodiments, the expandable guide catheter comprises an expandable distal end. In some embodiments, the expandable guide catheter comprises a dual braid layer. In some embodiments, the expandable guide catheter comprises a polymeric coating. In some embodiments, the expandable guide catheter comprises a coating. In some embodiments, the expandable guide catheter comprises a mesh. In some embodiments, the expandable guide catheter comprises an inner portion which provides decreased surface area, decreased surface contact, and/or decreased friction relative to an object within a lumen of the guide catheter.

In some embodiments, a method of retrieving a thrombus is provided. The method can include accessing an interior of a blood vessel. The method can include advancing expandable guide catheter through the blood vessel. In some embodiments, the expandable guide catheter comprising a portion that is compressed by a cover. The method can include expanding the expandable guide catheter by removing the cover.

In some embodiments, the method can include using balloon embolectomy to remove material from the body. In some embodiments, the method can include using a basket to remove material from the body. In some embodiments, the method can include using filter to remove material from the body. In some embodiments, the method can include using a collection bag to remove material from the body. In some embodiments, the method can include aiding the introduction of the expandable guide catheter into the vasculature with a dilator.

In some embodiments, a system can comprise, not comprise, consist essentially of, or consist of any number of features of the disclosure.

In some embodiments, a method can comprise, not comprise, consist essentially of, or consist of any number of features of the disclosure.

BRIEF DESCRIPTION OF THE DRAWINGS

FIG. 1A illustrates an embodiment of a catheter system with tensioners.

FIG. 1B illustrates the embodiment of the catheter system shown in FIG. 1.

FIG. 2A illustrates a close-up view of the distal end of the catheter system with the tensioners in an inactivated state.

FIG. 2B illustrates a close-up view of the proximal end of the catheter system with the tensioners in an inactivated state.

FIG. 3A illustrates a close-up view of the distal end of the catheter system with the tensioners in an activated state.

FIG. 3B illustrates a close-up view of the proximal end of the catheter system with the tensioners in an activated state.

FIG. 4A illustrates a basket loading tool pre-loaded onto the delivery catheter.

FIG. 4B illustrates the basket loading tool of FIG. 4A slid over a tubular body or a basket.

FIG. 4C illustrates the basket loading tool of FIG. 4A slid over a nosetip.

FIG. 4D illustrates a first member slid over the tubular body or the basket.

FIG. 4E illustrates the tubular body located within the first member.

FIG. 4F illustrates the basket loading tool of FIG. 4A slid over the first member to remove the basket loading tool.

FIG. 4G illustrates the basket loading tool of FIG. 4A removed.

FIG. 5A illustrates a basket loading tool pre-loaded onto a delivery catheter.

FIG. 5B illustrates the basket loading tool slid towards a tubular body or a basket.

FIG. 5C illustrates the basket loading tool slid over the tubular body or the basket.

FIG. 20 illustrates an expandable funnel catheter in a loaded configuration.

FIG. 21 illustrates the expandable funnel catheter of FIG. 20 in the expanded configuration.

FIG. 22 illustrates the expandable funnel catheter of FIG. 20 with the funnel beginning to fold inward.

FIG. 23 illustrates the expandable funnel catheter of FIG. 20 with the funnel folded inward.

FIG. 33 illustrates a single suture configuration.

FIG. 34A illustrates a non-limiting capture guide configuration.

FIG. 34B illustrates another non-limiting capture guide configuration.

FIG. 34C illustrates another non-limiting capture guide configuration.

FIG. 35 illustrates non-limiting different expandable funnel shaft configurations of laser cut patterns.

DETAILED DESCRIPTION

Figure 4A:
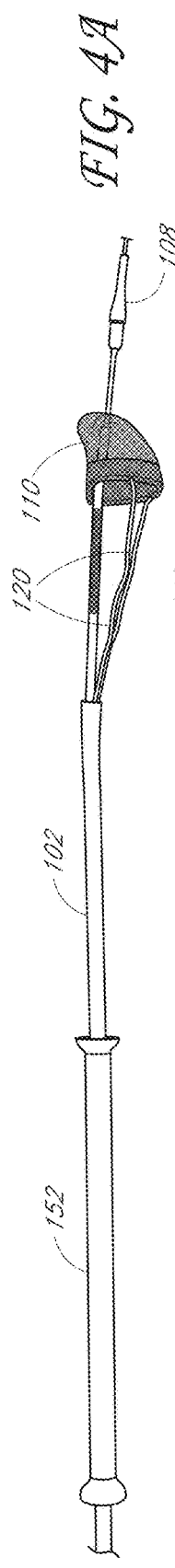
FIGS. 4A-4G illustrate a method of loading the catheter system into a delivery catheter using a loading tool, and, in particular.

In some embodiments, disclosed herein are capture systems and methods to retrieve and remove materials including emboli, thrombi, blood clots, stones/calculi, and/or foreign materials from the body of the patient (including devices, such as luminal devices positioned at least partially within the patient and associated with vascular or nonvascular systems). The capture systems and methods can remove materials from the vascular system, including but not limited to devices within or connected to the vascular system, such as stents, filters, and indwelling catheters including but not limited to dialysis catheters. The capture systems and methods can remove materials nonvascular areas to treat, for example, gallstones, kidney stones, common bile duct stones, and the like. The capture systems can be delivered percutaneously or via other techniques in a body of the patient.

The capture system can include a first member. The first member can comprise a central lumen. The first member can be an outer sheath. The first member can comprise at least one lumen. The first member can function to cover a portion of the capture system, such as a tubular body.

The capture system can include a second member. The second member can comprise a central lumen. The second member can be an inner sheath. The second member can comprise at least one lumen. The second member can be a pushrod. The second member can function to move a portion of the capture system, such as the tubular body.

The capture system can include the tubular body. The tubular body can comprise a shape memory material. The tubular body can be a shape memory body. The tubular body can include a first end, a second end, and an axial length therebetween. The first end of the tubular body can have an opening. In some embodiments, the second end of the tubular body can be coupled to the second member.

During use of the capture system, the tubular body is transformable to a first configuration in which the first end is expanded while the second end and a majority of the tubular body remains compressed within the central lumen of the first member. In some embodiments, the second end is positioned proximal to the first end. The tubular body has a first expanded axial length and a first width along the first expanded axial length in the first configuration.

During use of the capture system, the tubular body is transformable to a second configuration. In some embodiments, the tubular body transforms via movement between the first member and the second member. In some embodiments, the tubular body transforms via movement of one or more tensioners. In some embodiments, the tubular body has a second expanded axial length greater than the first expanded axial length and the shape memory body has a second width along the second expanded axial length. In some embodiments, the second width of the shape memory body along the second expanded axial length is substantially the same as the first width of the shape memory body along the first expanded axial length.

The capture system is used to remove emboli, thrombi and other foreign materials from the vascular system. The capture system can be used to remove acute, subacute and chronic or organized clot. As clot or thrombus is formed and deposited on to the vessel, the clot or thrombus minimally adheres to the vessel wall. With time, the clot or thrombus increases its wall adherence eventually becoming difficult to remove. Thus, a capture system with high resistance is needed to remove this degree of clot formation.

The capture system comprises a capture guide. In some embodiments, the capture guide comprises nitinol. In some embodiments, the capture guide comprises a loop. In some embodiments, the capture guide comprises a nitinol loop. The capture guide can be a ring-shaped guide attached to a circumference of the proximal-facing opening of the tubular body. In some embodiments, the capture guide at least partially circumscribes the first end opening. In some embodiments, the capture guide fully partially circumscribes the first end opening. In some embodiments, the capture guide forms a continuous loop. In some embodiments, the capture guide forms a non-continuous loop. The capture guide can be radially expanded during use. The capture guide can be compressed during delivery.

The capture system comprises a tubular body. The tubular body can be a wire braided mesh. The tubular body can have an expanded portion extending from the opening. The expanded portion can be considered the basket. The tubular body can form a wire braided basket. The tubular body can be porous, semi-permeable, and non-porous. The tubular body can include nitinol braided, woven, or non-woven mesh, or nitinol wire. In some embodiments, the tubular body is coated with a hydrophilic or hydrophobic agent, or noncoated. In some embodiments, the tubular body includes a shape memory metal or material. In some embodiments, the tubular body does not include a shape memory metal or material.

The capture guide is positioned at the first end of the tubular body and forms the opening. The tubular body extends from the first end to the fold. In some embodiments, a portion of the tubular body is compressed and extends from the folded distal end to the second end. The tubular body is designed to axially lengthen. In some embodiments, the tubular body is configured to roll out, invert, evert, and/or variably lengthen proximally from the first configuration to the second configuration. The second axial length can be different from the first axial length. In some embodiments, the width of the capture assembly does not substantially change from the first configuration to the second configuration.

The capture system can include a proximal-facing opening of the tubular body. The tubular body can be expanded to dynamic fold point which serves as the effective expanded distal end of the tubular body. The compressed reserve length segment of the tubular body can be about or at least about 10%, 20%, 30%, 40%, 50%, 60%, 70%, 80%, 90% or more of the absolute axial length of the tubular body. In some embodiments, the second end of the tubular body can remain inverted, rolled up, and/or otherwise radially compressed. In some embodiments, the second end of the tubular body can be circumscribed by the second member. In some embodiments, the second end of the tubular body can be fixed to the second member at an attachment site. The dynamic fold point can vary along the length of the tubular body depending on the length of the segment that is expanded. The dynamic fold point floats and is not directly attached to the first member or the second member, and as such moves when the expanded segment of the tubular body axially lengthens.

The capture system can include the first member and the second member described herein. The capture guide and tubular body can attach to a series of coaxial shafts. The second member can be disposed within the central lumen of the first member. The capture guide and tubular body can initially deploy in short and low profile. This initial deployment can be the first configuration described herein. The capture guide and tubular body can then lengthen to increase the basket length to capture the clot or other material.

The capture guide functions to open and maintain the basket opening to capture, collect, receive and remove the clot or other material. The capture guide can conform to different vessel diameter and geometric configurations such as round, oval, ellipse, or other vessel cross-sectional shapes. The capture guide can be positioned at different angles or angular orientations relative to the vessel. In some methods of use, the capture guide will deflect upon encountering resistance as the loop is retracted proximally.

In some embodiments, the capture system can include one or more features to enable the capture guide, such as a nitinol loop, to withstand high resistance without deflecting while conforming to the vessels. The capture system can include one or more features to enable the capture guide to scrape the clot or other foreign material from the vessel wall. The capture system can include one or more features that maintain the shape of the capture guide, for instance during proximal retraction to axially lengthen the tubular body. The capture system can include one or more features to reduce or prevent deflection of the capture guide.

FIGS. 1A and 1B illustrate an embodiment of a capture system 100. The capture system 100 can include a first member 102 or outer sheath. The first member 102 can include a central lumen 104. The central lumen 104 can be sized to accept one or more components of the capture system 100. The capture system 100 can include a second member 106. The second member 106 can be disposed within the central lumen 104.

The capture system 100 can include a tubular body 110. The tubular body 110 can include a first end 112 and a second end 114. The second end 114 attachment point can be further inside the second member 106 than what is shown in FIG. 1A. The second end 114 attach point can be anywhere along the length of the second member. The tubular body 110 can include an axial length between the first end 112 and the second end 114. The first end 112 can include a capture guide 116. The capture guide 116 can define an opening 118. In some embodiments, the second end 114 can be coupled to the second member 106. In some embodiments, the second end 114 can be disposed within the second member 106. In some embodiments, the second end 114 can be coupled to the nose tip 108. In some embodiments, the second end 114 can be coupled to a third member. In some embodiments, the second end 114 can couple to an inner guidewire lumen. In some embodiments, the capture guide 116 can be coupled to the second member 106.

The capture system 100 can include at least part of the tubular body 110 compressed in a first configuration. The first end 112 of the tubular body 110 is expanded. The capture guide 116 is expanded. The tubular body 110 has a first expanded axial length and a first width along the first expanded axial length. The capture system 100 can include a nose tip 108 extending beyond distal end or dynamic fold of the tubular body 110.

The tubular body 110 is transformable to a second configuration. In some embodiments, the tubular body 110 is transformable via movement of the tensioners as described herein. In some embodiments, the tubular body 110 is transformable via movement of the first member 102, movement of the second member 106, and/or movement between the first member 102 and the second member 106. In some embodiments, the tubular body 110 is transformable via movement of the first member 102, movement of the second member 106, and/or movement of the third member. The tubular body 110 has a second expanded axial length greater than the first expanded axial length and the shape memory body has a second width along the second expanded axial length. In some embodiments, the second width of the shape memory body along the second expanded axial length is substantially the same as the first width of the shape memory body along the first expanded axial length.

In some embodiments, the tubular body 110 is configured to invert, evert, or roll out. The compressed reserve length segment of the tubular body 110 is about or at least about 10%, 20%, 30%, 40%, 50%, 60%, 70%, 80%, 90% or more of the absolute axial length of the tubular body 110, or ranges including any two of the foregoing values. The compressed reserve length segment of the tubular body 110 remains inverted, rolled up, and/or otherwise radially compressed and circumscribed by the up to the point of the fold or inversion of the tubular body 110. The dynamic fold point varies along the length of the tubular body 110 depending on the length of the compressed reserve length segment that is expanded. The dynamic fold point floats and moves proximally when the expanded segment of the tubular body 110 axially lengthens.

The tubular body 110 can include a mesh net-like structure with a proximal-facing opening at one end. The tubular body 110 can be made of a shape memory metal or polymer, a non-shape memory metal such as stainless steel, or another non-shape memory fabric, or other material. In some embodiments, conventional net-like structures such as used in IVC and other embolic filters can be utilized with systems and methods herein. In some embodiments, a thrombus capture device can be configured to axially lengthen throughout a working range, with or without radially shortening the tubular body 110 throughout the working range.

In some embodiments, the proximal end opening of the tubular body 110 can include a capture guide 116. The capture guide 116 can take the form of a radially expandable shape memory partial or full ring-like annular structure. In some embodiments, a significant portion of the surface area and/or the axial length of the mesh of the tubular body 110 remains in a compressed configuration, as the other end of the tubular body 110 and the capture guide 116 are expanded. The tubular body 110 can be a generally tubular net-like mesh structure that is collapsible, expandable and configured to axially lengthen or shorten, such as within a working range, while maintaining or substantially maintaining its diameter within the working range to retrieve. The tubular body 110 can capture foreign or otherwise unwanted materials within the body, including the vascular system such as blood clots, thrombus and/or foreign materials.

The capture system 100 can include one or more features, tensioners, such as, for example, tethers or strings 120. FIGS. 1A and 1B show the features, tensioners, such as tethers or strings 120. The tensioner 120 can include a distal end 122 and a proximal end 124. The distal end 122 of each tensioner 120 couples to the capture guide 116. The proximal end 124 of each tensioner 120 extends through the first member 102, or outer sheath. The proximal end 124 of each tensioner 120 extends toward the proximal end of the capture system 100. In some embodiments, the proximal end 124 of each tensioner 120 couples to the first member 102. In some embodiments, the proximal end 124 of each tensioner 120 couples to a midpoint of the first member 102 or along the length of the first member 102. In some embodiment, the proximal end 124 of each tensioner 120 couples to the proximal control handle. In some embodiments, the proximal end 124 of each tensioner 120 couples to the second member 106. In some embodiments, the proximal end 124 of each tensioner 120 couples to a third member or sheath. In FIGS. 1A and 1B, the tensioners 120 are activated. The method of attaching the tensioners 120 to the nitinol loop can be of various methods such as either thermal, non-thermal, laser, chemical, mechanical. In some embodiments, the tensioner 120 and nitinol loop can be continuous or one piece. In some embodiments, the capture guide comprises a loop with either only one strut or a plurality of struts extending proximal and coupled to the first member or inner member. In some embodiments, the struts can extend to the control handle.

The proximal end 124 of each tensioner 120 can extend through the first member 102, or outer sheath. The proximal end 124 of each tensioner 120 extends toward the proximal end of the capture system 100. In some embodiments, the proximal end 124 of each tensioner 120 couples to the first member 102. In some embodiments, the proximal end 124 of each tensioner 120 couples to a midpoint of the first member 102 or along the length of the first member 102. In some embodiment, the proximal end 124 of each tensioner 120 couples to the proximal control handle as described herein.

The tensioners 120 can be connected to the tubular body 110. The tensioners 120 can be connected to the capture guide 116. The tensioners 120 can be connected to keep the basket in tension. The tensioners 120 can be connected to keep the capture guide 116 rigid. The tensioners 120 can be connected to keep the opening of the tubular body 110 from deflecting. FIG. 1A is a top view. FIG. 1B is a side view. While two tensioners 120 are shown, the capture system 100 can include any number of tensioners (e.g., one tensioner, two tensioners, three tensioners, four tensioners, five tensioners, six tensioners, seven tensioners, eight tensioners, nine tensioners, ten tensioners, between two and three tensioners, more than two tensioners, less than five tensioners, or any range of the foregoing values).

In some embodiments, the movement of the tubular body 110 is independent of the tensioners 120. The tubular body 110 can move whether the tensioner 120 is activated or deactivated. When tubular body 110 first deploys, the tensioner 120 is activated. The tubular body 110 is pulled back with tensioners 120 activated to capture clot or other material. The tubular body 110 also lengthens at the same time. The tubular body 110 has a first configuration in which the first end 112 and the capture guide 116 are expanded and one or more tensioners 120 are activated while the second end and a majority of the tubular body remains compressed and the tubular body 110 has a first expanded axial length and a first width along the first expanded axial length. The tubular body 110 is transformable to a second configuration where the tubular body 110 has a second expanded axial length greater than the first expanded axial length and the tubular body 100 has a second width along the second expanded axial length.

The capture system 100 can be used in combination with a funnel system, such as expandable funnel catheter 200, 300, 400 described herein. The funnel system can include an expandable funnel tip. The funnel system can include an expandable shaft. The funnel system can include a housing body. The housing body can be removed to allow the expandable funnel tip and/or the expandable shaft to expand. The funnel tip and the funnel shaft are expandable.

The method of retrieving a material can include any steps described herein. In some methods, a funnel system is positioned with respect to a target region within a lumen of the patient. The funnel tip can be delivered in a collapsed configuration and expanded near the material. The funnel tip can be positioned in a proximal position relative to the material. In some embodiments, a capture system is positioned. The capture system can be positioned in a distal position relative to the material. The capture system can have one or more tensioners coupled to the capture guide activated when the capture system is positioned. The capture system 100 can be transformed to lengthen over the material. The capture system 100 can be retrieved into the funnel system. The capture system 100 can retract through the expandable funnel catheter 200, 300, 400 as described herein.

FIGS. 1A and 1B show two tensioners 120. The tensioners 120 can be sutures. The tensioners 120 can be any member. The tensioners 120 can connect the capture guide 116 to the first member 102 or outer sheath. In some embodiments, the tensioners 120 can connect to a nitinol loop which forms the capture guide 116. In some embodiments, the tensioners 120 can connect to the distal end of the first member 102. In some embodiments, the tensioners 120 can extend in the lumen of the first member 102. The first member 102 can extend proximally and connect to a coupling insert of a handle of the capture system 100, described herein. FIGS. 1A and 1B show two tensioners 120 in an activated state. When activated, the tensioners 120 apply tension to the tubular body 110 and the capture guide 116.

FIG. 2A show two tensioners 120 in an inactivated state. When inactive, the tensioners 120 do not apply tension to the tubular body 110 and the capture guide 116. When inactive, the capture guide 116 can be deflected in this condition.

FIG. 2B shows the proximal end of the capture system 100. The capture system 100 can include at least one handle 130. The first member 102 can extend proximally and connect to a coupling insert 132 of the handle 130 of the capture system 100. FIG. 2B shows that the coupling insert 132 is not fully engaged in the coupling body 134. The coupling body 134 and the coupling insert 132 are semi-engaged.

FIG. 3A show two tensioners 120 in an activated state. When active, the tensioners 120 apply tension to the tubular body 110 and the capture guide 116. When active, deflection of the capture guide 116 can be reduced or limited. FIG. 3B shows that the coupling insert 132 is fully engaged in the coupling body 134. The coupling body 134 and the coupling insert 132 are engaged. When the coupling body 134 and the coupling insert 132 are engaged, the tensioners 120 apply tension to the capture guide 116.

The tension applied by the tensioners 120 can hold the capture guide 116 rigid. This rigid capture guide 116 is able to scrape the inner wall of the vessel, thereby dislodging foreign material. The rigid capture guide 116 is held under tension. The capture guide 116 is less likely to deflect when it encounters foreign material adhered to the vessel wall. In some embodiments, the capture guide 116 will score or cut the foreign material. In some embodiments, the capture guide 116 will scrape or shear the foreign material from the vessel wall. The tension applied by the tensioners 120 can be adjustable to various tension such as low, medium or high depending on the adhering degree of wall adherent clot or foreign materials. The tensioners can be, for example, tethers, strings, springs, rods, tubes, coils, wires, or laser cut metallic elements. The tensioners can be any feature configured to apply tension. The tension applied by the tensioners 120 can be adjustable as described herein with the use of a control handle. In some embodiments, the capture guide is round or elliptical shape with either one strut or a plurality of struts extending proximal and couple to the first member or inner member. In some embodiments, the struts can extend to the control handle. The capture guide with struts can be laser cut (FIG. 34). The strut can be straight, curve with features along its length to allow the strut to stretch under high tensile stress.

The tensioners 120 enable the capture guide 116 to withstand high resistance without deflecting while conforming to the vessels. In some embodiments, there are two or more tensioners 120, such as sutures or members, connecting the capture guide 116 to the distal end of the first member 102 or outer sheath. In some embodiments, the one or more tensioners 120 extend in one or more lumens of the first member 102. The first member 102 can extend proximally and connect to the coupling insert 132. The coupling insert 132 engages the couplings body 134 to activate the tensioners 120 to apply tension. Once the tensioners are activated, the capture guide 116 is held fixed and is unable to deflect during removal. Maintaining the capture guide 116 rigid during removal will help score, scrap, cut, shear and capture material adhered to the vessel wall. The tensioners 120 can be inactivated by disengage the coupling insert 132 from the coupling body 134. In some embodiments, the tensioners 120 are simultaneously activated. In some embodiments, the tensioners 120 are independently activated.

In some embodiments, the tensioner 120 can be rigid. In some embodiments, the tensioner 120 can be a solid member. In some embodiments, the tensioner 120 can be flexible. In some embodiments, the tensioner 120 can be a suture. In some embodiments, the tensioner 120 can be a tether. In some embodiments, the tensioner 120 can be one or more strings, springs, rods, tubes, coils, wires, or laser cut metallic elements. In some embodiments, the capture guide is circular in shape such as round or elliptical shape with either one strut or a plurality of struts extending proximal and couple to the first member or inner member. In some embodiments, the struts can extend to the control handle. The capture guide with struts can be laser cut (FIG. 34). The strut can be straight, or curved with features along its length to allow strut to stretch under high tensile stress. The tensioner 120 can be one or a plurality of tensioners coupled to the capture guide 116. The tensioner 120 can be made of polymeric materials such as suture filaments or metallic wires. The tensioner 120 can include filaments material such as PET, PTFE, Kevlar, Polyimide or PEEK. The tensioner 120 can include metallic wires such as stainless steel or nitinol. The metallic wires can have features such as coil, and/or zig-zag shapes to allow the wires to stretch or give under high tensile stress.

In some embodiments, the capture system can have one or more tensioners 120 coupled to the capture guide 116. In some embodiments, the capture system can have one or more tensioners 120 coupled to the tubular body 110. In some embodiments, the capture system can have one or more tensioners 120 coupled to the opening 118. The tensioners 120 can be disposed around the circumference of the opening 118.

The method of attaching the one or more tensioners 120 can be of various methods. In some embodiments, the tensioners 120 are attached to the capture guide 116. The tensioners 120 can be attached by various methods such as either thermal, non-thermal, laser, chemical, and/or mechanical methods such as a suture tied knot, wrap, or loop. In some embodiments, the one or more tensioners 120 and capture guide 116 can be continuous or one piece. In some embodiments, the one or more tensioners 120 and the capture guide 116 can be monolithically formed. In some embodiments, the one or more tensioners 120 and the capture guide 116 can be separately formed. In some embodiments, the one or more tensioners 120 and the tubular body 110 can be monolithically formed. In some embodiments, the one or more tensioners 120 and the tubular body 110 can be separately formed. In some embodiments, the capture guide 116 and the tubular body 110 can be monolithically formed. In some embodiments, the capture guide 116 and the tubular body 110 can be separately formed.

The capture system can have either one tensioner 120 or a plurality of tensioners 120. When there are two or more tensioners 120, the individual tensioners 120 can be located equal distance from each other, around the circumference of the capture guide 116. For instance, two tensioners 120 can be separated by about 180 degrees. For instance, three tensioners 120 can be separated by about 120 degrees. For instance, four tensioners 120 can be separated by about 90 degrees. When there are two or more tensioners 120, the individual tensioner 120 can be located unequal distance from each other, around the circumference of the capture guide 116. For instance, two tensioners 120 can be separated by about 120 degrees. For instance, two tensioners 120 can be separated by about 90 degrees. When there is one tensioner, the tensioner can be positioned opposite from the second member 106 connected to the capture guide 116.

In some embodiments, the capture system can have two tensioners 120. The two tensioners 120 can be diametrically opposed. The two tensioners 120 can be equally spaced. The two tensioners 120 can be symmetrical. The two tensioners 120 can be on opposite sides of the capture guide 116. The two tensioners 120 can be separated by 30 degree, 45 degrees, 60 degrees, 75 degrees, 90 degrees, 105 degrees, 120 degrees, 135 degrees, 150 degrees, 165 degrees, 180 degrees, or any range of the foregoing values. The two tensioners 120 can apply equal tension to the capture guide 116. The two tensioners 120 can be located on the lateral sides of the capture guide 116.

Referring back to FIG. 3A, the capture system can have two tensioners 120. One tensioner 120 can be on the right side of the capture guide 116 and one tensioner 120 can be on the left side of the capture guide 116. In some embodiments, the capture guide 116 can be coupled to the second member 106. The second member 106 and the two tensioners 120 can be equally spaced. The two tensioners 120 and the second member 106 can be separated by 30 degrees, 45 degrees, 60 degrees, 75 degrees, 90 degrees, 105 degrees, 120 degrees, 135 degrees, 150 degrees, 165 degrees, 180 degrees, or any range of the foregoing values. The two tensioners 120 and the second member 106 can be separated by 120 degrees in some embodiments. Other arrangements of tensioners 120 are contemplated.

In some embodiments, the capture system can have three tensioners 120. At least two tensioners 120 can be diametrically opposed. The three tensioners 120 can be equally spaced. The three tensioners 120 can be symmetrical. At least two tensioners 120 can be on opposite sides of the capture guide 116. At least two tensioners 120 can be separated by 30 degree, 45 degrees, 60 degrees, 75 degrees, 90 degrees, 105 degrees, 120 degrees, 135 degrees, 150 degrees, 165 degrees, 180 degrees, or any range of the foregoing values. The three tensioners 120 can apply equal tension to the capture guide. The three tensioners 120 can form an equilateral triangle on the capture guide. The three tensioners 120 can form an isosceles triangle. At least one tensioner 120 can be located at the top of the capture guide 116. At least one tensioner 120 can be located opposite the second member 106. The two additional tensioners 120 can be located on the lateral sides of the capture guide 116. Other arrangements of tensioners 120 are contemplated.

In some embodiments, the capture system can include one or more tensioners 120. Tension can be applied to the one or more tensioners 120 to hold the capture guide 116 taut. The one or more tensioners 120 can maintain the shape of the capture guide 116. The one or more tensioners 120 can allow the capture guide to remain rigid. The one or more tensioners 120 can allow the capture guide to scrape the clot or other foreign material from the vessel wall. The one or more tensioners 120 can be positioned to equally distribute tension to the capture guide 116. The one or more tensioners 120 can be positioned to increase the rigidity of the capture guide 116 during scraping. The one or more tensioners 120 can facilitate dislodging material from the inner wall of the vessel upon retraction of the capture guide 116. The one or more tensioners 120 can be adjusted to alter the tension applied to the capture guide 116. The one or more tensioners 120 can prevent or limit deflection of the capture guide 116 when the capture guide encounters foreign material on the vessel wall.

The one or more tensioners 120 can be configured to prevent inversion of the capture guide 116. The one or more tensioners 120 can maintain the capture guide 116 in a plane. The one or more tensioners 120 can move the capture guide 116 while maintaining the capture guide 116 perpendicular to the vessel. The one or more tensioners 120 can prevent the capture guide 116 from deflecting when interacting with deposited material. The one or more tensioners 120 can prevent the capture guide 116 from sliding over the material. one or more tensioners 120 can cause the capture guide to scrape along the vessel wall.

Figure 4B:
Figure 4C:
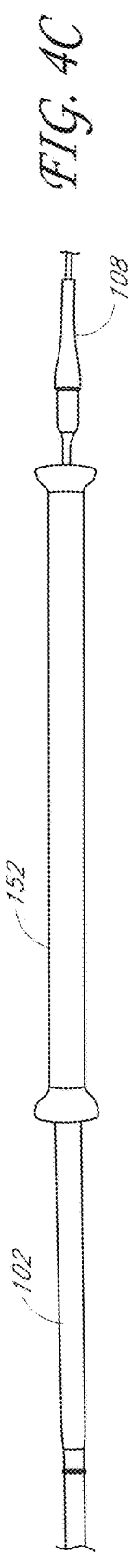

FIGS. 4A-4G shows methods of loading the tubular member 110 and the tensioners 120 into a delivery catheter. In FIG. 4A, the basket loading tool 152 is pre-loaded onto the delivery catheter. The basket loading tool 152 can be located on the outside of the first member 102 or outer sheath. In FIG. 4B, the basket loading tool 152 is slid over the tubular body 110 or basket. The basket loading tool 152 is slid distally along the length of the first member 102. In FIG. 4C, the basket loading tool 152 is slid over the nosetip 108. The tubular body 110 is located within the basket loading tool 152 in FIG. 4C.

In some embodiments, the basket loading tool 152 can include a funnel tip. In some embodiments, the basket loading tool 152 can include an expandable end. In some embodiments, the basket loading tool 152 can cause the tubular body 110 to radially compress. In some embodiments, the basket loading tool 152 can include two funnel tips. In some embodiments, the basket loading tool 152 can include two expandable ends. In some embodiments, the basket loading tool 152 can be loaded in two orientations relative to the first member 102.

Figure 4D:
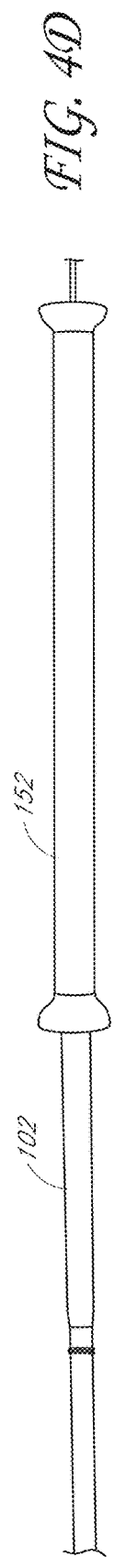
Figure 4E:
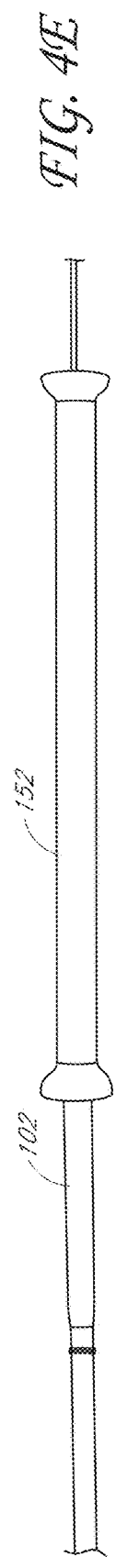

In FIG. 4D, the first member 102 or other sheath is slid over the tubular body 110 or basket. The first member 102 is slid along the inner wall of the basket loading tool 152. In FIG. 4E, the first member 102 is slid to engage the nosetip 108. The tubular body 110 is located within the first member 102 in FIG. 4E.

Figure 4F:
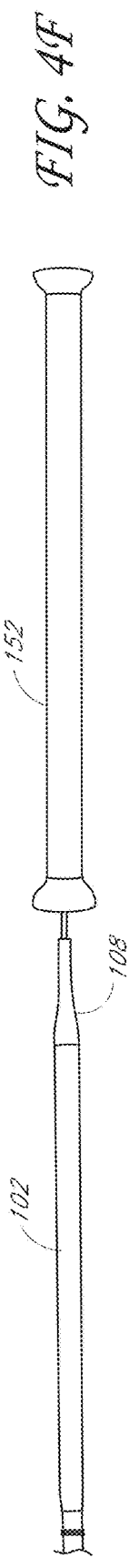
Figure 4G:
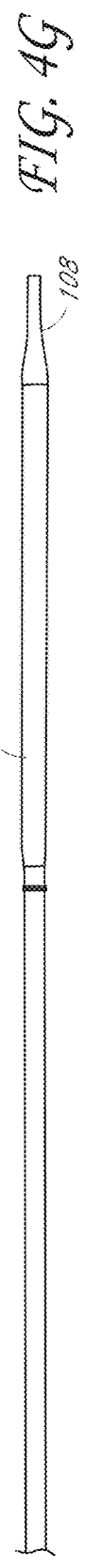

In FIG. 4F, the basket loading tool 152 is slid over the first member 102 to remove the basket loading tool 152. The tubular body 110 is located within the first member 102. In FIG. 4G, the basket loading tool 152 is removed.

Figure 5A:
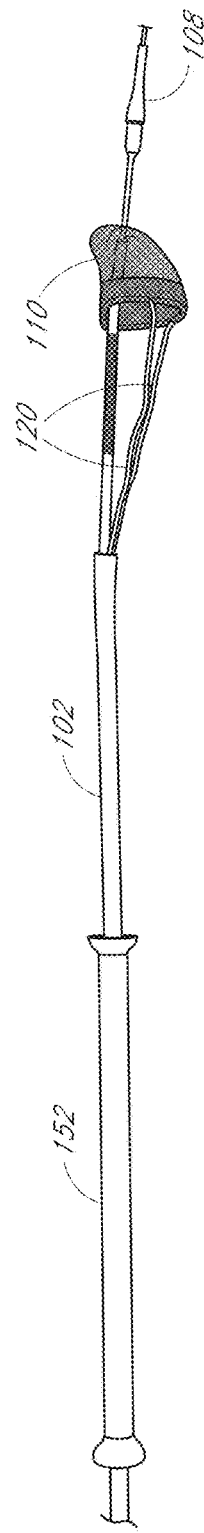
FIGS. 5A-5C illustrate a method of loading the catheter system into a delivery catheter using a loading tool, and, in particular.
Figure 5B:
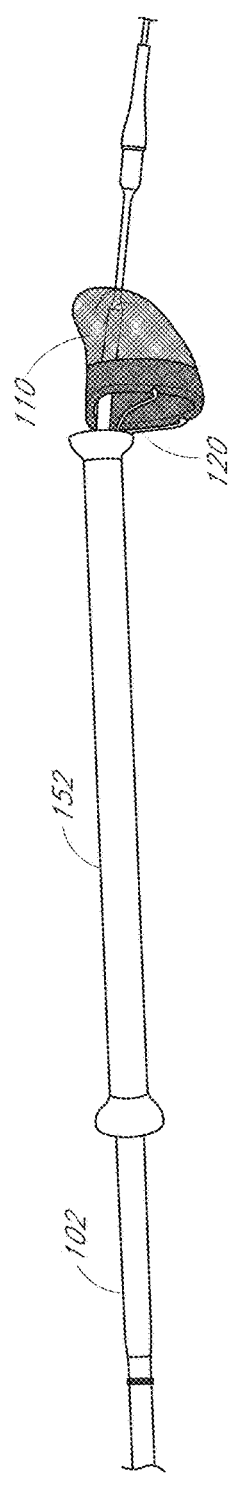
Figure 5C:
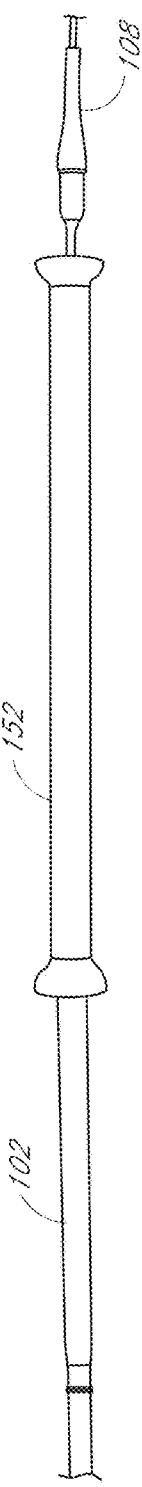

FIGS. 5A-5C shows methods of loading the tubular member 110 and the tensioners 120 into a delivery catheter. In FIG. 5A, the basket loading tool 152 is pre-loaded onto the delivery catheter. The basket loading tool can be located on the outside of the first member 102 or outer sheath. The tensioners 120 are connected to the tubular member 110. In some methods, the tensioners 120 are connected to the basket to keep the basket in tension. In some methods, the tensioners 120 apply tensions during loading of the basket with the basket loading tool 152. In other methods, the tensioners 120 do not apply tensions during loading of the basket with the basket loading tool 152.

In FIG. 5B, the basket loading tool 152 is slid toward the tubular body 110 or basket. The basket loading tool 152 is slid distally along the length of the first member 102. The tensioners 120 apply tension as the basket loading tool 152 slides to cover the tubular body 110.

In FIG. 5C, the basket loading tool 152 is slid over the tubular body 110 or basket. The basket loading tool 152 is slid distally toward the nosetip 108. In some embodiments, the tensioners 120 apply tension as the basket loading tool 152 slides to cover the tubular body 110. The proximal end 124 of the tensioners 120 are connected to the shaft of the first member 102 or outer shaft. In some methods, the basket loading tool 152 is slid over the nosetip 108. In some methods, the first member 102 or other sheath is slid over the tubular body 110 or basket. In some methods, the first member 102 is slid along the inner wall of the basket loading tool 152. In some methods, the first member 102 is slid to engage the nosetip 108. In some methods, the basket loading tool 152 is slid over the first member 102 to remove the basket loading tool 152.

Figure 6A:
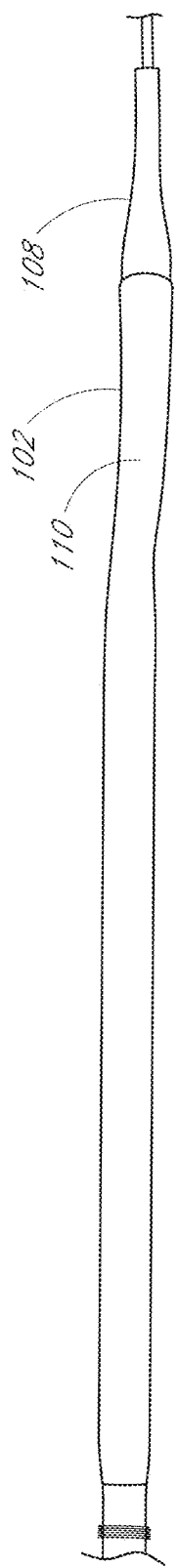
FIG. 6A illustrates a close-up view of the distal end of the catheter system loaded inside the delivery catheter.
Figure 6B:
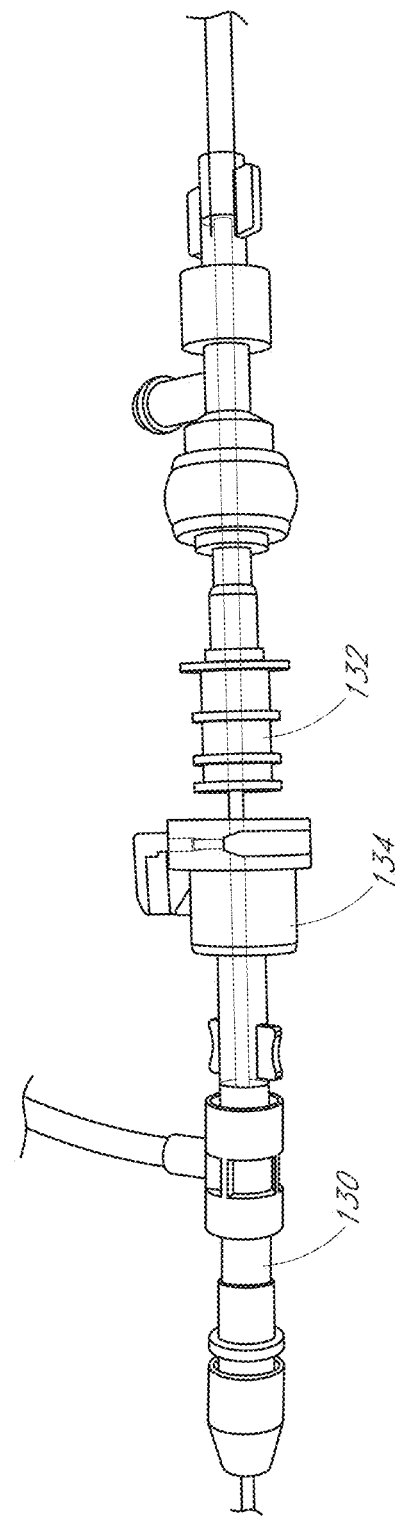
FIG. 6B illustrates a close-up view of the proximal end of the catheter system loaded inside the delivery catheter.

FIG. 6A show the distal end of the delivery catheter with the basket and tensioner loaded inside the delivery catheter. The basket or tubular member 110 is fully loaded within the first member 102. The first member 102 engages the nose tip 108. FIG. 6B shows the proximal end of the delivery catheter with the handle 130 where the coupling insert 132 is disengaged from the coupling body 134. In some methods, the tensioners 120 are not under tension when loaded inside the first member 102. In some methods, the tensioners 120 are under tension when loaded inside the first member 102, and the coupling insert 132 is engaged with the coupling body 134.

Referring back to FIG. 3A, the distal end 122 of each tensioner 120 couples to the capture guide 116. In some embodiments, the second member 106 is coupled to the capture guide 116. The capture guide 116 can be configured to be retracted to scrape the vessel wall. In some embodiments, movement of the tensioners 120 causes this movement of the capture guide 116.

Referring to FIG. 6B, the proximal end 124 of each tensioner 120 can extend toward the proximal end of the capture system 100. In some embodiments, the proximal end 124 of each tensioner 120 extends along the second member 106. In some embodiments, the proximal end 124 of each tensioner 120 does not couple to the second member 106. In some embodiments, the proximal end 124 of each tensioner 120 can extend through the first member 102. In some embodiments, the proximal end 124 of each tensioner 120 can extend through an outer sheath. The proximal end 124 of each tensioner 120 can extend to the coupling insert 132. In some methods, the tensioners 120 are not under tension when the coupling body 134 and the coupling insert 132 are separated. In some methods, the tensioners 120 are under tension when the coupling body 134 and the coupling insert 132 engaged. The tensioners 120 can be under tension within the lumen of the first member 102.

In some embodiments, pulling the handle 130 of the capture system 100 pulls the one more tensioner 120. The first member 102 can extend proximally and connect to a coupling insert 132. The coupling body 134 and the coupling insert 132 can be engaged when the capture system 100 is pulled. The movement of the handle 130 of the capture system 100 causes the one more tensioner 120 to apply tension to the capture guide 116. The tension causes the capture guide 116 to move along the vessel wall, thereby contacting, e.g., scraping the vessel wall. Further movement causes further contacting, e.g., scraping until the unwanted material is removed from the vessel wall.

Figure 7:
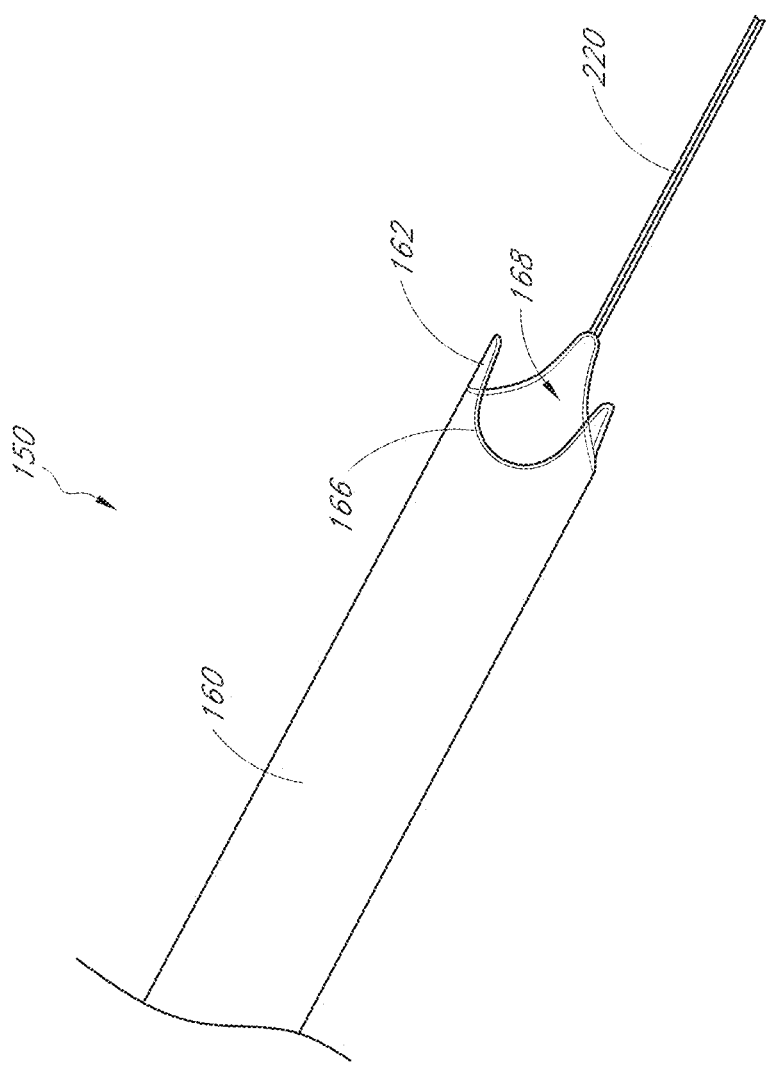
FIG. 7 illustrates an embodiment of a catheter system.

FIG. 7 shows a capture system 150. The capture system 150 can include any of the features of the capture system 100 described herein. The capture system 150 can include a tubular body 160. The tubular body 160 can include a first end 162 and a second end (not shown). The tubular body 160 can include an axial length between the first end 162 and the second end. The first end 162 can include a capture guide 166. The capture guide 166 can define an opening 168.

In some embodiments, the capture guide comprises 166 nitinol. In some embodiments, the capture guide 166 comprises a loop or loop like structure. In some embodiments, the capture guide 166 comprises an open shape. In some embodiments, the capture guide 166 comprises a closed shape. In some embodiments, the capture guide 166 comprises nitinol or other shape memory material. In some embodiments, the capture guide can be a stent-like shape. The capture guide 166 can be attached to a circumference of the proximal-facing opening of the tubular body 160. In some embodiments, the capture guide 166 at least partially circumscribes the first end opening. In some embodiments, the capture guide 166 fully partially circumscribes the first end opening. In some embodiments, the capture guide 166 forms a continuous shape. In some embodiments, the capture guide 166 forms a non-continuous shape. The capture guide 166 can have the ability to expand. The capture guide 166 can be of different geometric configurations such that it can be expanded when subject to radial forces. The capture guide 166 can have any shape.

In some embodiment, one or more tensioners 170 are attached to the capture guide 166. The tensioners 170 can have any of the features of the tensioners 120 described herein. The capture guide 166 can include one or more points or tips. In some embodiments, each tensioner 170 can couple to one of the points or tips. In some embodiments, the capture guide 166 includes two points. Other configurations are contemplated (e.g., one point, two points, three points, four points, five points, six points, or any range of the foregoing values). In some embodiments, the capture guide 166 includes two tensioners. Other configurations are contemplated (e.g., one tensioner, two tensioners, three tensioners, four tensioners, five tensioners, six tensioners, or any range of the foregoing values).

The tensioner 170 can be attached to the capture guide 166. In some embodiments, the tensioner 170 can extend within the lumen of the first member or outer sheath. In some embodiments, the tensioner 170 can extend within another inner lumen that is within or adjacent to the outer sheath wall as described herein. The outer sheath can have one or more lumens within or adjacent to its wall thickness. In some embodiments, the inner lumens can extend the entire length of the outer sheath. In some embodiments, the inner lumens can extend partially. In some embodiments, the inner lumens can terminate within the outer sheath, distally, in the middle of the outer sheath, or proximally.

The capture guide 166 has the ability to expand to larger diameter. The tensioners 170 can attach to the apex of the nitinol loop or capture guide 166. The capture guide 166 can have different geometric configurations. In some embodiments, the capture guide 166 can form a zig-zag shape, a fish mouth shape, a stent-like shape, etc. The capture guide 166 can expand when subject to radial force.

In some embodiments, the tensioners 170 extend from the capture guide 166 to the proximal end of the delivery catheter. The tensioners 170 can attach to a handle mechanism. In some embodiments, the tensioners 170 can attach to the coupling insert 132. The tensioners can be activated to apply tension when the coupling insert 132 engages the coupling body 134. In some embodiments, the tensioners 170 can be articulated to different level of tension.

Figure 8:
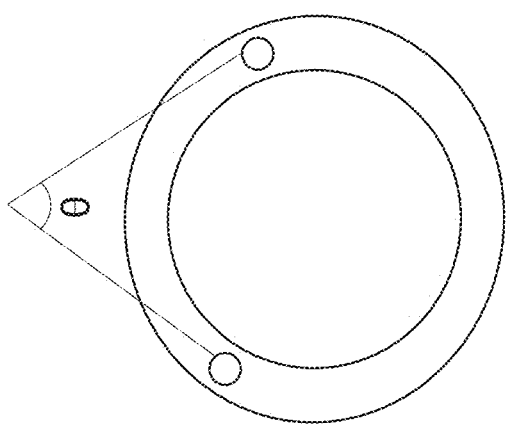
FIG. 8 illustrates a tri-lumen shaft body.

FIG. 8 illustrates a tri-lumen shaft body. The shaft body includes two inner lumens separated by the angle theta. The shaft body includes a central lumen. The first member 102 can have a tri-lumen shaft body. The second member 106 can be disposed within the central lumen. The tensioners 120, 170 can be disposed within the inner lumens. The inner lumens can guide the tensioners through the first member 102. The inner lumens can prevent tangling of the tensioners 120, 170. In some embodiments, the tensioners 120, 170 extend within the central lumen. In some embodiments, each tensioners 120, 170 extend within a separate lumen. The inner lumens are within the wall thickness of the first member 102 or outer sheath.

In some embodiments, the tubular body can axially lengthen or shorten without reducing or substantially reducing its diameter through a working length/axial range because the radially expanded portion of the tubular body is subject to none or minimal tension as it elongates or shortens axially through that axial working range. Not to be limited by theory, this can be accomplished at least in part because the tubular body can elongate axially throughout the working range by unrolling, everting, or otherwise expanding or transforming a radially compressed reserve segment of tubular body. The dynamic fold point of the radially expanded portion of the tubular mesh may not be the absolute end of the tubular mesh. Rather the second end can be located proximally thus forming a floating or dynamic fold point. The dynamic fold point is not fixed, and as such not under any, or not substantially under any tension. The radially compressed reserve segment of tubular body thus extends back proximally, and in some cases within the expanded portion of the tubular body. In some embodiments, the second end can be fixed relative to the second member, such that movement of the second member can cause movement of the second end thereby rolling out the tubular body.

In some embodiments, disclosed herein are capture systems and methods to retrieve and remove materials including emboli, thrombi, blood clots, stones/calculi, and/or foreign materials from the body of the patient. The capture systems and methods can remove materials from the vascular system. The capture systems and methods can remove materials nonvascular areas to treat, for example, gallstones, kidney stones, common bile duct stones, and the like. The capture systems can be delivered percutaneously in a body of the patient.

Figure 9:
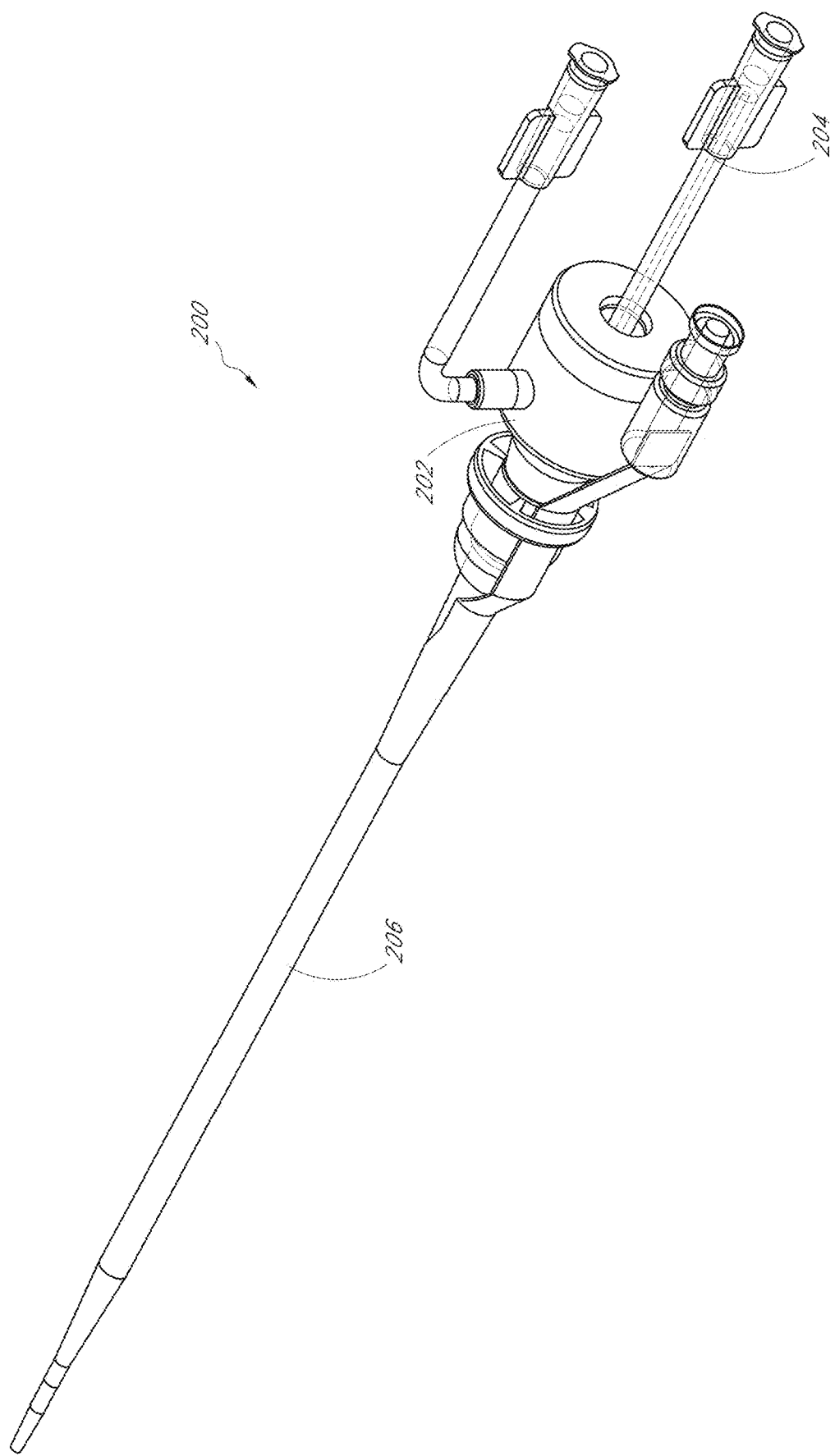
FIG. 9 illustrates an embodiment of an expandable funnel catheter in a loaded configuration.
Figure 10:
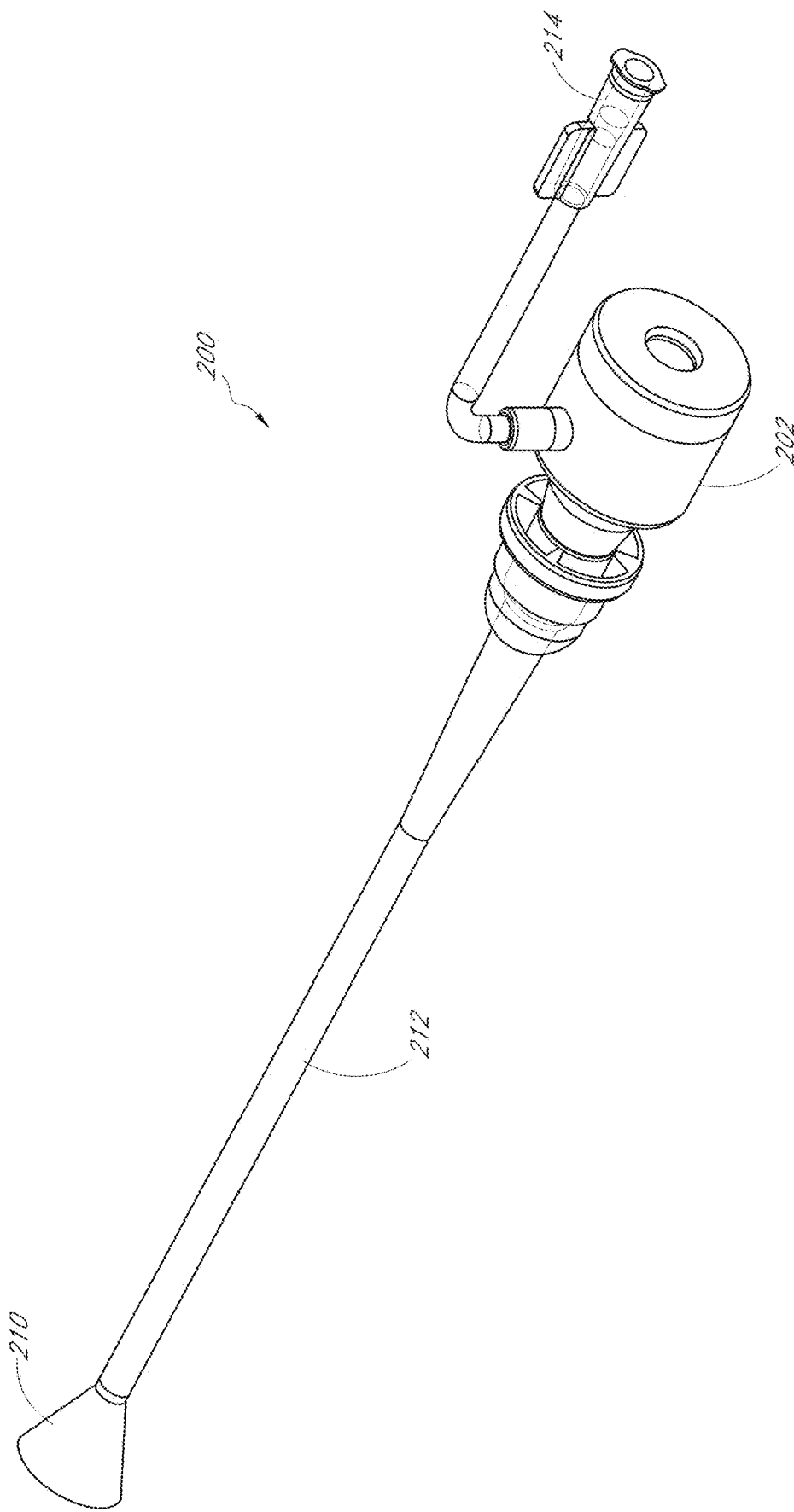
FIG. 10 illustrates an embodiment of the expandable funnel catheter in a deployed configuration.

FIGS. 9 and 10 illustrate an embodiment of an expandable funnel catheter 200. The expandable funnel catheter 200 can be utilized in combination with the capture system 100 described herein. In some embodiments, the tubular body 110, 160 is retracted though the expandable funnel catheter 200. In some embodiments, unwanted material is retracted though the expandable funnel catheter 200. In some embodiments, a tool is retracted though the expandable funnel catheter 200. In some embodiments, a collection basket is retracted through the expandable funnel catheter. In some embodiment, a collection bag is retracted through the expandable funnel catheter. In some embodiment, a collection mesh is retracted through the expandable funnel catheter. In some embodiment, an inflated device such as a balloon is retracted through the funnel catheter. In some embodiment, an expandable nitinol element such as a disk, bulb, and/or bundle is retracted through the expandable funnel catheter. In some embodiment, a polymeric plug, and/or arcuate, e.g., circular disk is retracted through the expandable funnel catheter. The expandable funnel catheter 200 can be utilized in combination with any system or method described herein. FIG. 9 illustrates the expandable funnel catheter 200 in a loaded configuration. The loaded configuration can be a delivery configuration. The loaded configuration can be a sterile packaged configuration. The expandable funnel catheter 200 can include a first hub 202. The expandable funnel catheter 200 can include a second hub 204. The expandable funnel catheter 200 can include a cover 206. The cover 206 can compress an expandable portion of the expandable funnel catheter 200. The cover 206 can be removable, as described herein. The cover can include scored or perforated features along its length to facilitate the removal. The score or perforation can be a single line or a plurality of line along its length.

FIG. 10 illustrates the expandable funnel catheter 200 in a deployed configuration. The cover 206 can be removed to transition the expandable funnel catheter 200 between the loaded configuration and the deployed configuration. The expandable funnel catheter 200 can include an expandable funnel tip 210. The expandable funnel tip 210 can be located near the end of the expandable funnel catheter 200. The expandable funnel catheter 200 can include an expandable shaft 212. The expandable funnel catheter 200 can include the first hub 202. The expandable funnel catheter 200 can include a flush port 214. The flush port 214 can extend from the first hub 202.

The expandable funnel catheter described herein can be utilized with clot capture systems. The expandable funnel catheter described herein can be utilized for material retrieval. The expandable funnel catheter described herein can be utilized in any method that requires the retraction of material through the expandable funnel catheter. The expandable funnel catheter described herein can be utilized for tubular body retrieval. The expandable funnel catheter described herein can be utilized for catheter retrieval. The expandable funnel catheter described herein can be utilized in any method that requires the retraction of tools through the expandable funnel catheter. The expandable funnel catheter can have wider application outside of removal of unwanted material. The expandable funnel catheter can be utilized in any surgical procedure. The expandable funnel catheter can be utilized in any method.

The expandable funnel catheter advantageously increases within a body lumen. The expandable funnel tip 210 of the expandable funnel catheter can expand. The expandable funnel tip 210 can expand to accommodate larger material and tools. The expandable funnel tip 210 can direct the material and/or tool to the expandable shaft 212. The expandable shaft 212 of the expandable funnel catheter can expand. The expandable shaft 212 can expand to accommodate material that is larger than the diameter of the shaft 212. The expandable shaft 212 can expand to accommodate a tool that is larger than the diameter of the shaft 212. The expandable shaft 212 can be expandable along the entire length of the shaft. The expandable shaft 212 can be expandable along a portion of the shaft. The expandable shaft 212 can be expandable near the expandable funnel tip 210.

In some embodiments, the funnel tip of the expandable funnel catheter does not expand. In some embodiments, only the funnel tip of the expandable funnel catheter expands. In some embodiments, the shaft of the expandable funnel catheter does not expand. In some embodiments, only the shaft of the expandable funnel catheter expands.

The expandable funnel catheter advantageously can be partially expanded and still be functional. The expandable funnel catheter advantageously can expand along only part of the length. The expandable funnel catheter advantageously expands when needed to remove material or accept a tool larger than the unexpanded diameter of the shaft 212. The expandable funnel catheter can facilitate removal of selected materials within a body. The expandable funnel catheter can pass material larger than the unexpanded diameter of the shaft 212 by allowing the shaft 212 to expand. The expandable funnel catheter advantageously allows flexibility in material removal depending on the size of the material.

Figure 11:
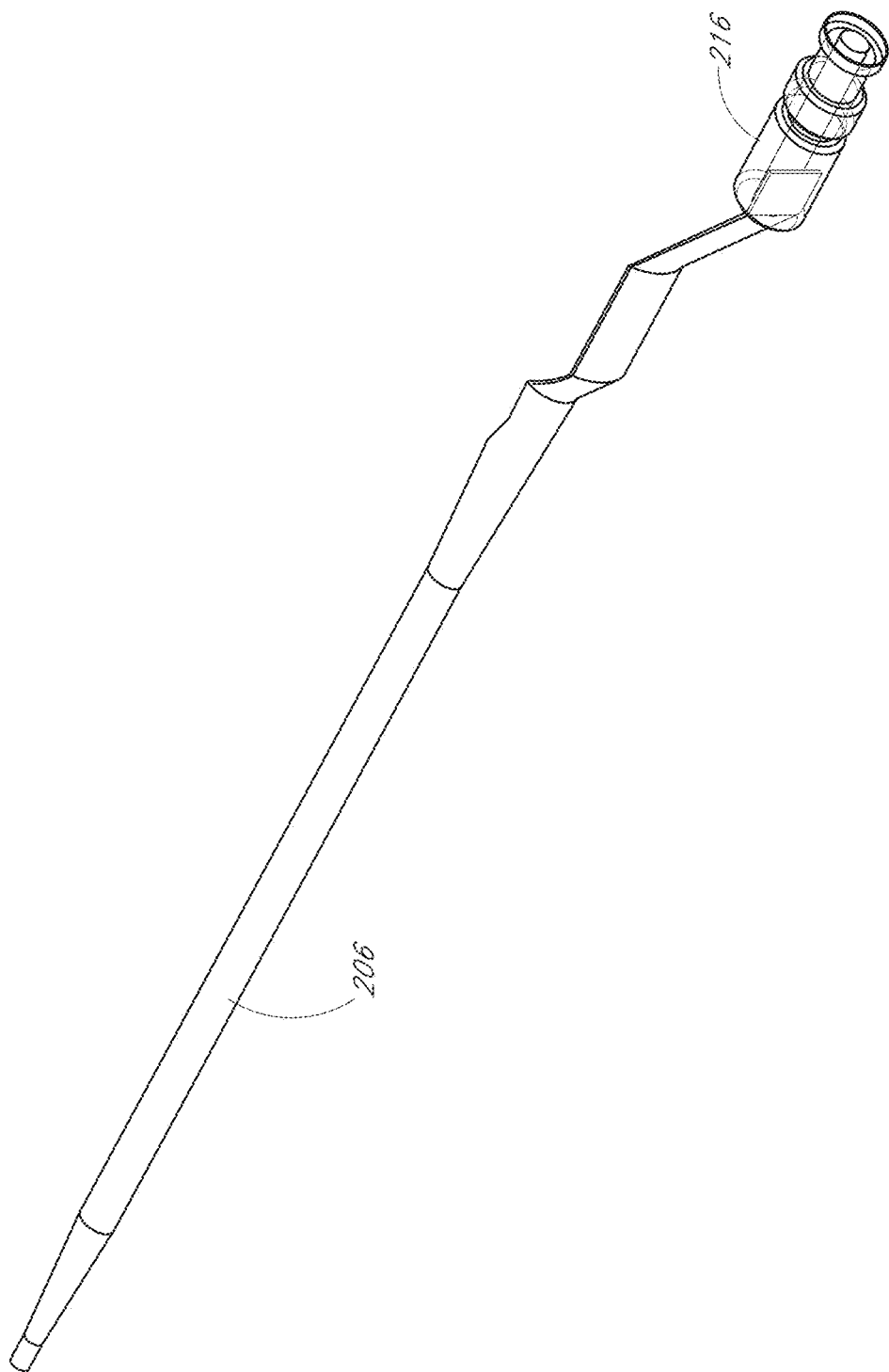
FIG. 11 illustrates an embodiment of a peel-away cover for an expandable funnel.

FIG. 11 illustrates the cover 206. The cover 206 can be a peel-away cover. The cover 206 can be utilized with the expandable funnel catheter 200. The cover 206 can compress the expandable funnel tip 210. The cover 206 can compress the expandable shaft 212. The cover 206 can include a hub 216. In some embodiments, the expandable funnel catheter 200 can be within a constraint. The cover 206 can function as a constraint to minimize the diameter of the expandable funnel catheter 200. In some embodiments, an outer sheath constrains the expandable funnel catheter 200. In some embodiments, the first member 102 constrains the expandable funnel catheter 200.

Figure 12:
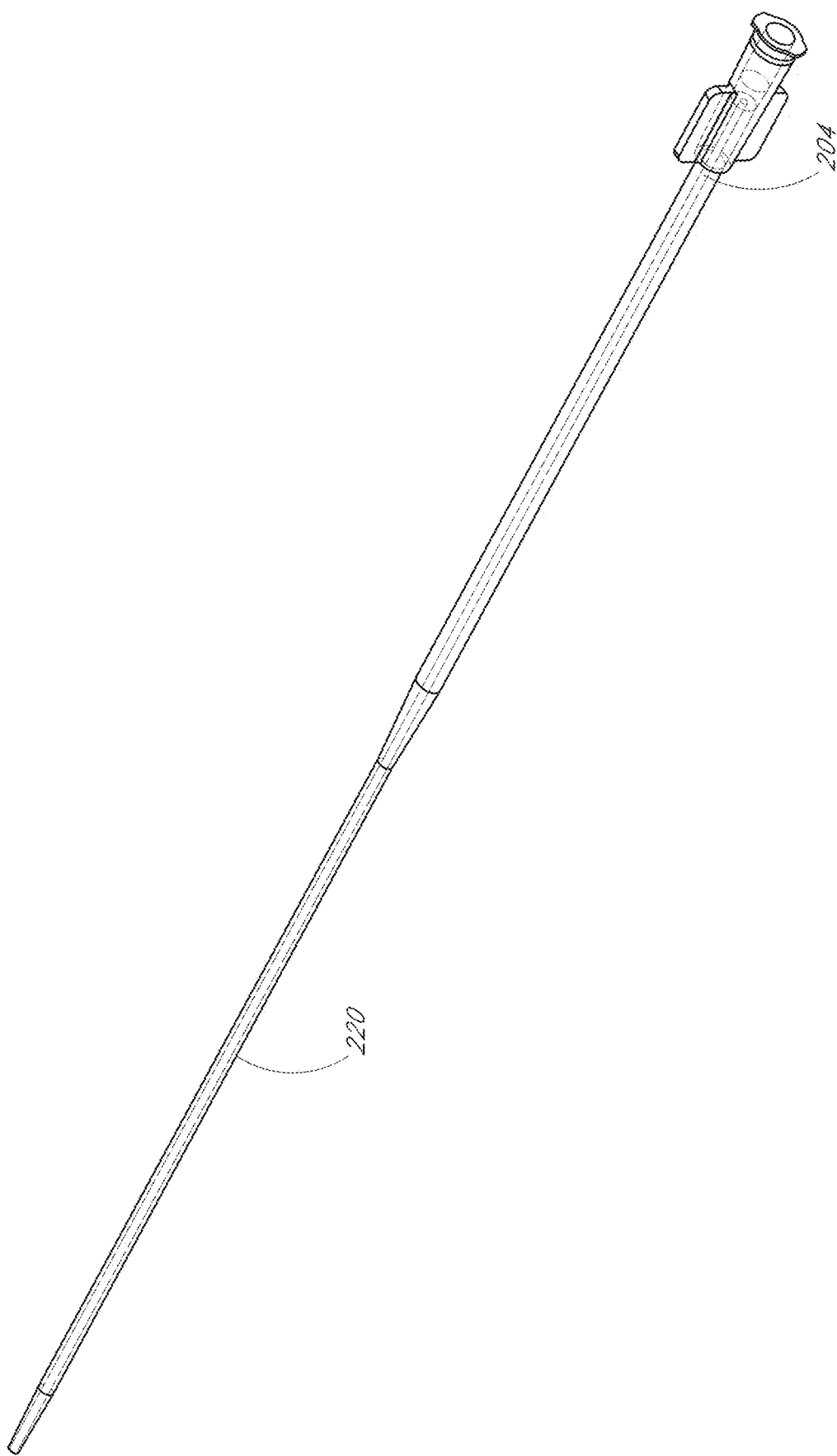
FIG. 12 illustrates an embodiment of a dilator for an expandable funnel.

FIG. 12 illustrates a dilator 220. The dilator 220 can extend through a lumen of the expandable funnel catheter 200. The dilator 220 can include the second hub 204. The dilator 220 can extend through a lumen of the expandable funnel catheter 200. In some embodiments, the dilator 220 can facilitate expansion of the expandable funnel catheter 200.

Figure 13:
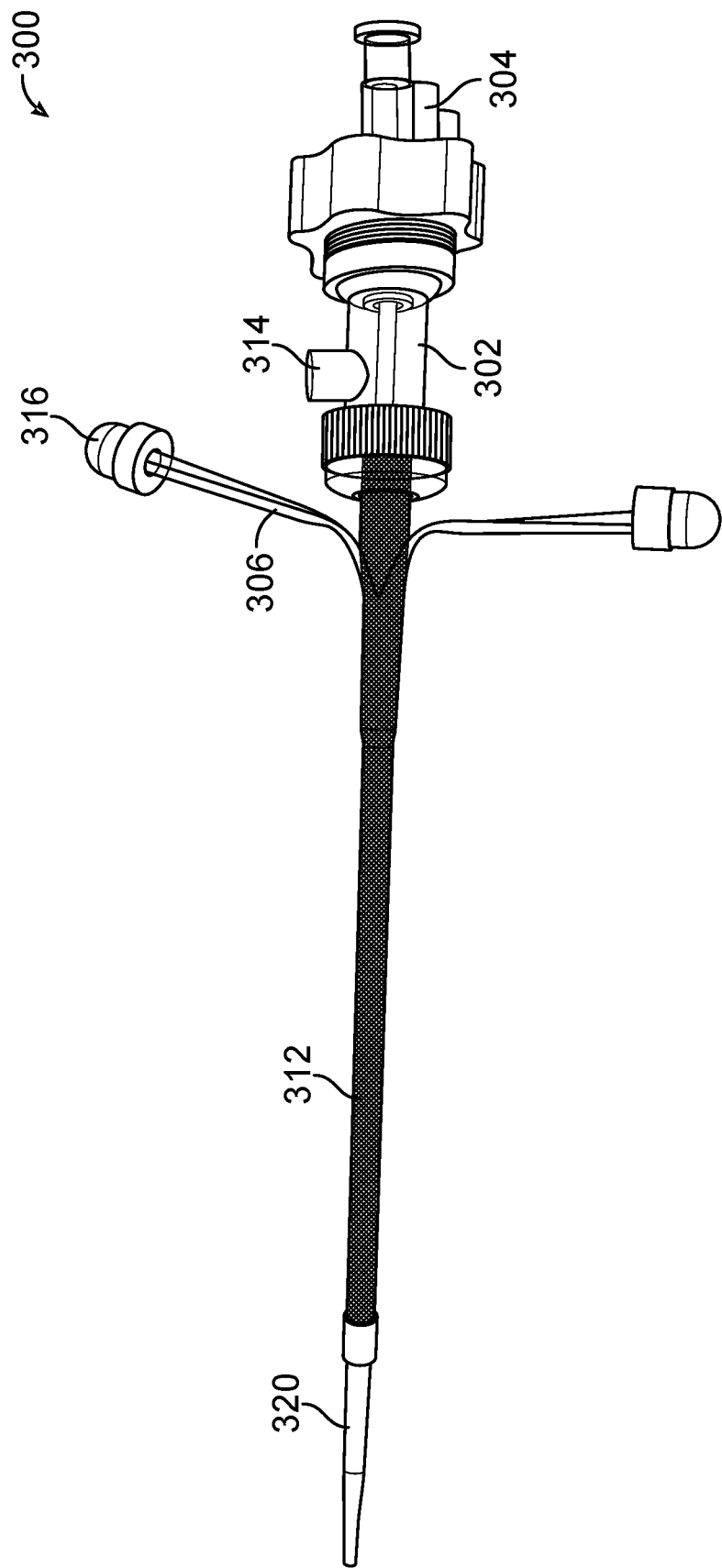
FIG. 13 illustrates an embodiment of an expandable funnel catheter in a loaded configuration.
Figure 14:
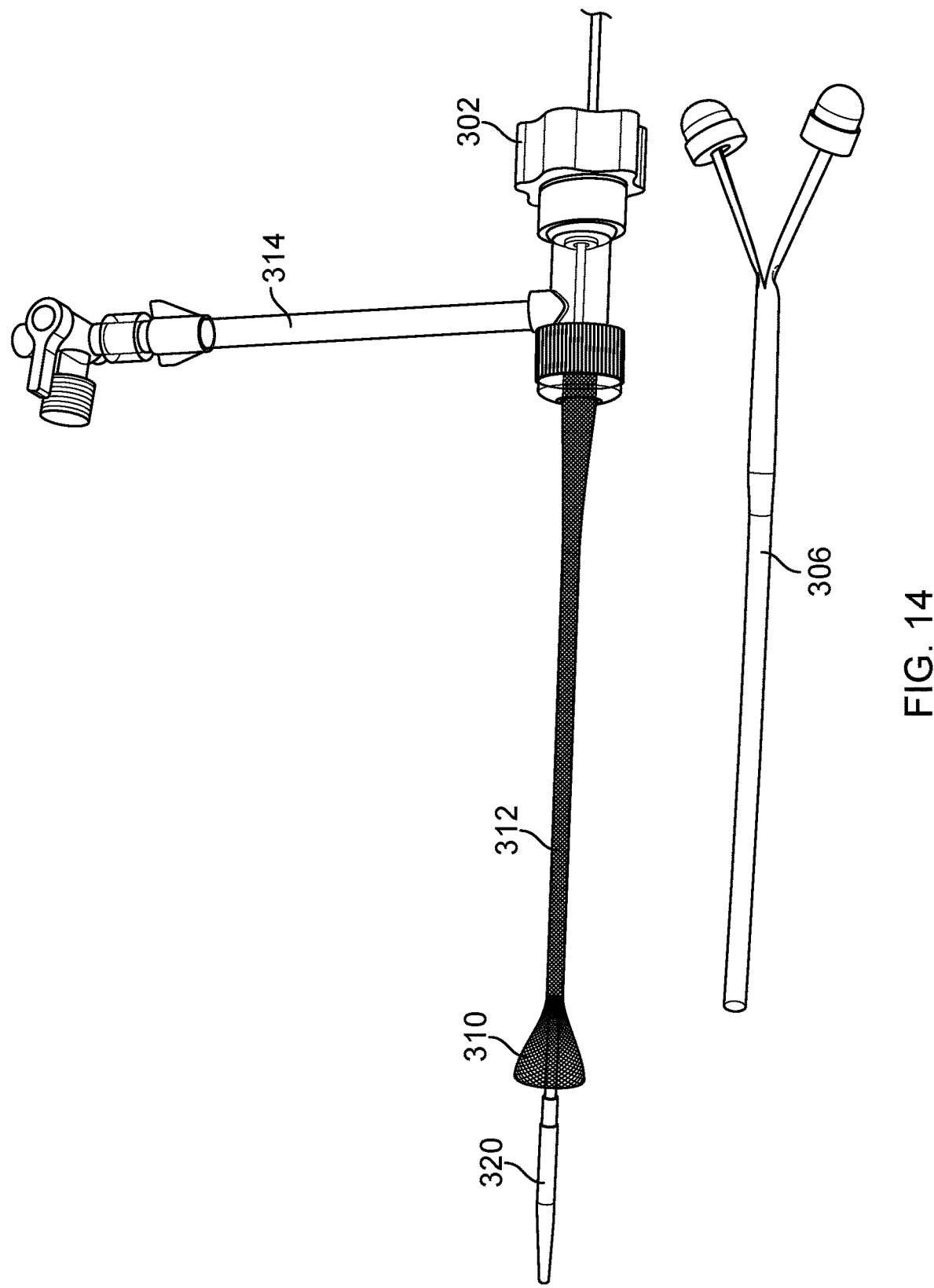
FIG. 14 illustrates an exploded view of the expandable funnel catheter.

FIGS. 13 and 14 illustrate an embodiment of an expandable funnel catheter 300. The expandable funnel catheter 300 can include any of the features of expandable funnel catheter 200. The expandable funnel catheter 300 can be utilized in combination with any system or method described herein. FIG. 13 illustrates the expandable funnel catheter 300 in a loaded configuration. The loaded configuration can be a delivery configuration. The loaded configuration can be a sterile packaged configuration. The expandable funnel catheter 300 can include a first hub 302. The expandable funnel catheter 300 can include a second hub 304. The expandable funnel catheter 300 can include a cover 306. The cover 306 can compress an expandable portion of the expandable funnel catheter 300. The cover 306 can be removable, as described herein. The expandable funnel catheter 300 can include a dilator 320. The dilator 320 can extend through a lumen of the expandable funnel catheter 300. The dilator 320 can include the second hub 304.

FIG. 14 illustrates the expandable funnel catheter 300 in a deployed configuration. The cover 306 can be removed to transition the expandable funnel catheter 300 between the loaded configuration and the deployed configuration. The expandable funnel catheter 300 can include an expandable funnel tip 310. The expandable funnel tip 310 can be located near the end of the expandable funnel catheter 300. The expandable funnel catheter 300 can include an expandable shaft 312. The expandable funnel catheter 300 can include an expandable body. The expandable funnel catheter 300 can be expandable along the length of the expandable funnel catheter 300. The expandable funnel catheter 300 can be entirely expandable. The expandable funnel catheter 300 can be selectively expandable, for instance only a portion of the expandable funnel catheter 300 is expanded during some methods. The expandable funnel catheter 300 can include the first hub 302. The expandable funnel catheter 300 can include a flush port 314.

Figure 15:
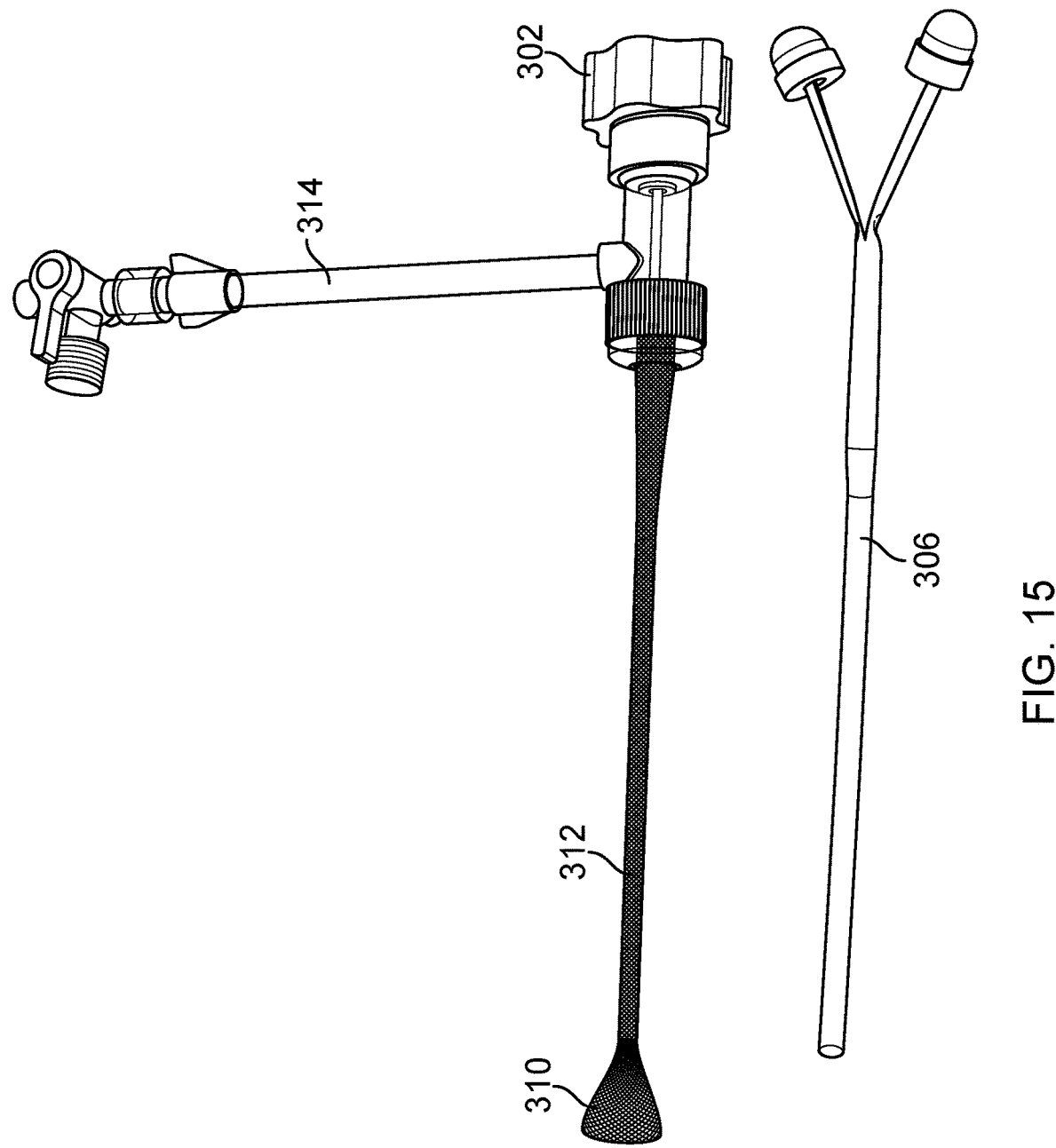
FIG. 15 illustrates another view of the expandable funnel catheter.

FIG. 15 illustrates an additional view. The cover 306 can be a peel-away cover. The cover 306 can be removed by pulling a tab. The cover 306 can be removed by breaking along a score line. The cover 306 can be removed by retracting the cover 306. The cover 306 can remain intact. The cover 306 can be severed. The cover 306 can be utilized with the expandable funnel catheter 300. The cover 306 can compress the expandable funnel tip 310. The cover 306 can compress the expandable shaft 312. The cover 306 can include one or more hubs 316.

Figure 16:
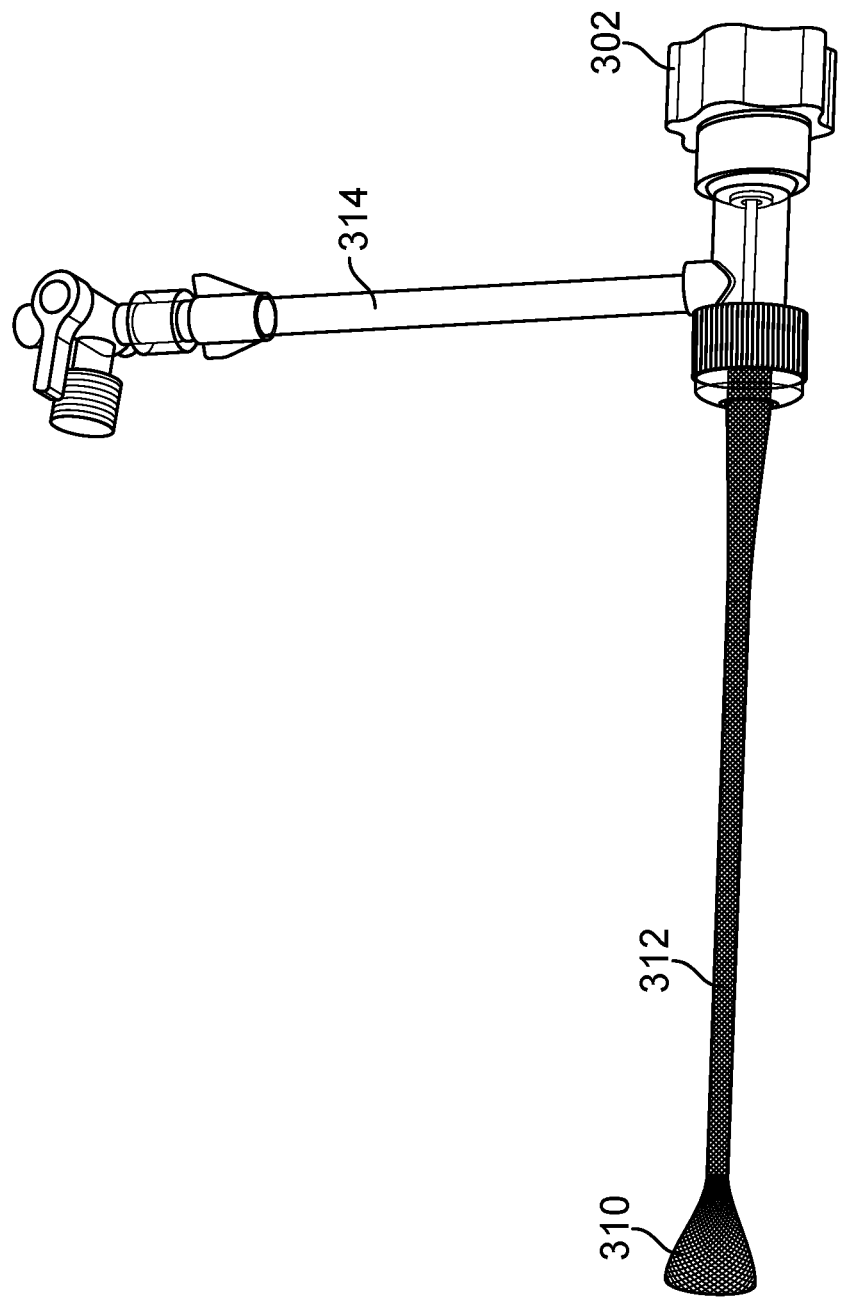
FIG. 16 illustrates a view of the expandable funnel body.

FIG. 16 illustrates an additional view. The expandable funnel body can include the expandable funnel tip 310. The expandable funnel body can include the expandable shaft 312. The proximal end is formed with an opening to couple to a housing or the first hub 302 and a flushing/aspiration port 314.

Figure 17:
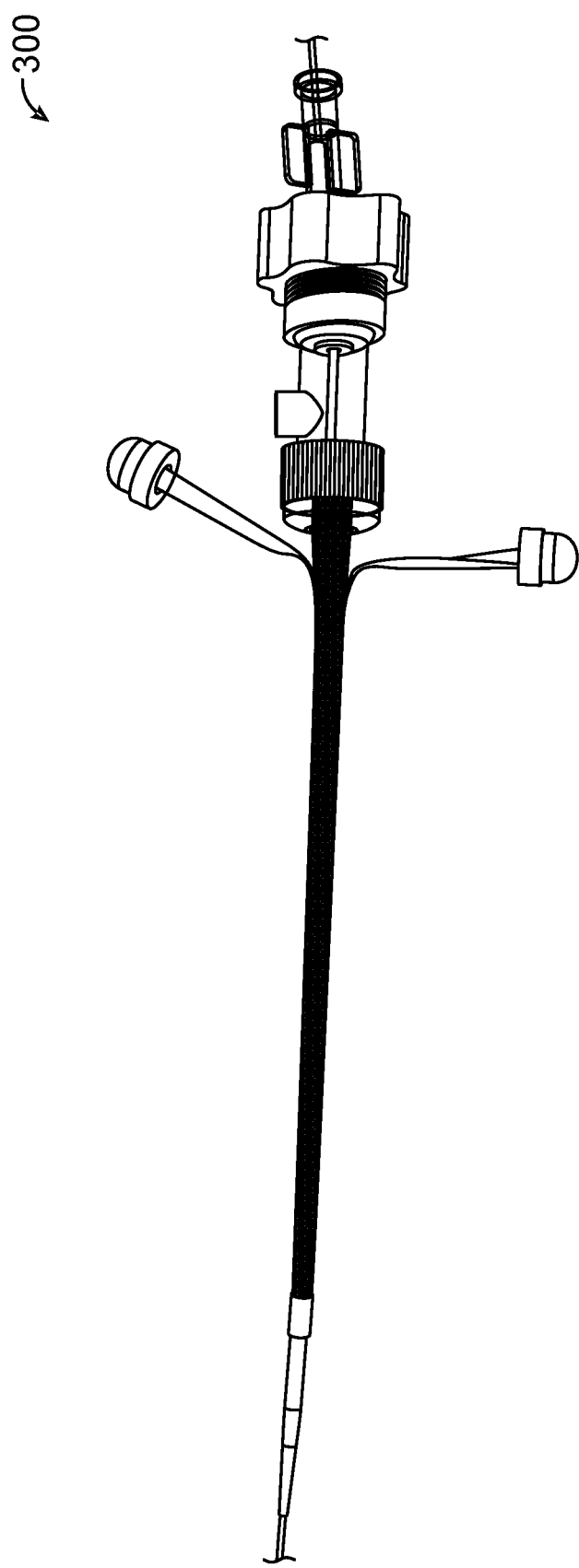
FIG. 17 illustrates an embodiment of an expandable funnel catheter in a delivery configuration.

FIG. 17 illustrates the expandable funnel catheter 300 in a loaded configuration. The loaded configuration can be a delivery configuration. The expandable funnel catheter 300 can be constrained for delivery. The expandable funnel catheter 300 can be expanded within the body of the patient.

Figure 18:
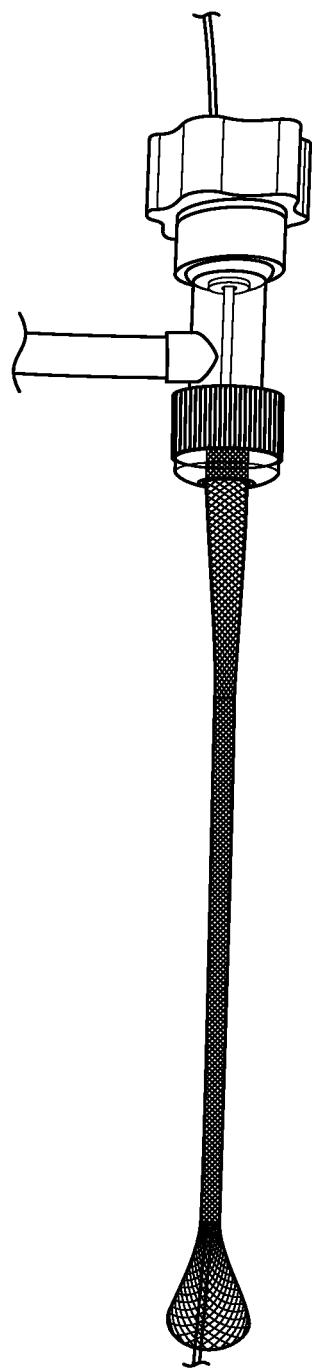
FIG. 18 illustrates an embodiment of the expandable funnel catheter without the peel-away cover.

FIG. 18 illustrates the expandable funnel catheter 300 in a deployed configuration. The expandable funnel catheter 300 is illustrated without the cover 306. The flush port can be used for flushing or aspirate to remove foreign materials or thrombus. The expandable funnel catheter 300 can be expandable along the entire length. The expandable funnel catheter 300 can accept material and/or tools larger than the resting diameter of the expandable shaft 312. The expandable shaft 312 can have a neutral diameter. The expandable shaft 312 can expand to the vessel wall to accept larger material and/or tools. In some embodiments, the expandable shaft 312 can radially expand. In some embodiments, the expandable shaft 312 can longitudinally contract upon expansion. In some embodiments, the construction of the expandable shaft 312 can facilitate expansion.

Figure 19A:
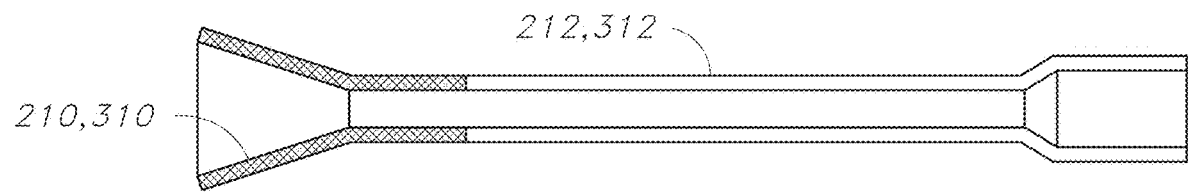
FIG. 19A illustrates an expandable funnel concept.

FIGS. 19A-19E illustrate additional expandable funnel concepts. FIG. 19A illustrates the location of the funnel braid. The expandable funnel tip 210, 310 can include a funnel braid. The expandable funnel tip 210, 310 can be conical. The expandable funnel tip 210, 310 can include a braided conical portion. The expandable funnel tip 210, 310 can include a braided cylindrical portion. The expandable funnel tip 210, 310 can include a mesh. The expandable funnel tip 210, 310 may or may not have conical portion.

FIGS. 19B-19E illustrate cross-sectional views of additional expandable funnel concepts. The expandable funnel catheter 200, 300 can include an inner layer. The expandable funnel catheter 200, 300 can include an outer layer. In some embodiments, the expandable funnel tip 210, 310 can include the inner layer and the outer layer. In some embodiments, the expandable shaft 212, 312 can include the inner layer and the outer layer.

Figure 19B:
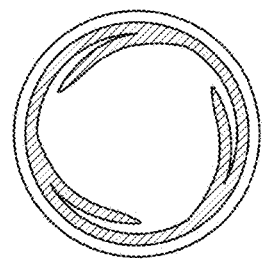
FIG. 19B illustrates a cross-sectional view of an additional expandable funnel concept.
Figure 19C:
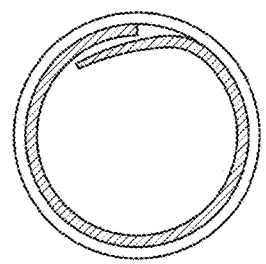
FIG. 19C illustrates a cross-sectional view of an additional expandable funnel concept.
Figure 19D:
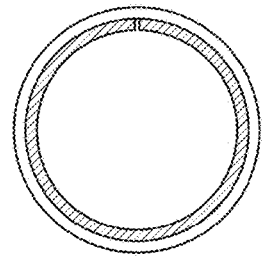
FIG. 19D illustrates a cross-sectional view of an additional expandable funnel concept.
Figure 19E:
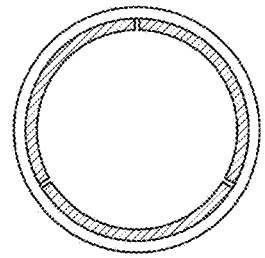
FIG. 19E illustrates a cross-sectional view of an additional expandable funnel concept.

FIG. 19B illustrates a first embodiment. The inner layer can allow expansion with folds. The outer layer can be a polymer material. FIG. 19C illustrates a second embodiment. The inner layer can have a fold that overlaps. The outer layer can be a polymer material. FIG. 19D illustrates a third embodiment. The inner layer can have a slit. The inner layer can have one or more slits. The inner layer can provide stiffness. The inner layer can be able to glide and open. The outer layer can allow expansion. FIG. 19E illustrates a fourth embodiment. The inner layer can have two, three, or more slits. The inner layer can be a polymeric material. The outer layer can be a polymeric material. The polymeric material can be the same, or different with respect to the inner layer and the outer layer. The outer layer can be stiffer. The inner layer can be stiffer with respect to the inner layer.

FIG. 20 illustrates the expandable funnel catheter 400 in a loaded configuration. The expandable funnel catheter 400 can have any features described herein. The expandable funnel catheter 400 can include a quick connection 450. The expandable funnel catheter 400 can include a peel-away cover 451. The expandable funnel catheter 400 can include an obturator 452. The expandable funnel catheter 400 can include a collapsed funnel catheter 455. The loaded configuration can be a delivery configuration. FIG. 20 illustrates the loaded funnel with a peel-away sheath.

FIG. 21 illustrates the expandable funnel catheter 400 in the expanded configuration. The expandable funnel catheter 400 can include a funnel shaft 453. The expandable funnel catheter 400 can include an expanded funnel 454. FIG. 21 illustrates the funnel deployed.

FIG. 22 illustrates the expandable funnel catheter 400. The expandable funnel catheter 400 can include a quick connection. The quick connection is disengaged wherein one member 460 is retracted proximally from second member 461 resulting the funnel 462 folding inward. FIG. 22 illustrates the funnel folding inward. The quick release is utilized to pull hub 460 proximally to fold the funnel 462 inward to a smaller profile.

FIG. 23 illustrates the expandable funnel catheter 400. The funnel is folded inward to the smaller profile. The funnel can be folded inward before removal from the body is minimize trauma at the access site. The distal end 463 includes the small profile end. The hub 460 is in a proximal position.

Figure 24:
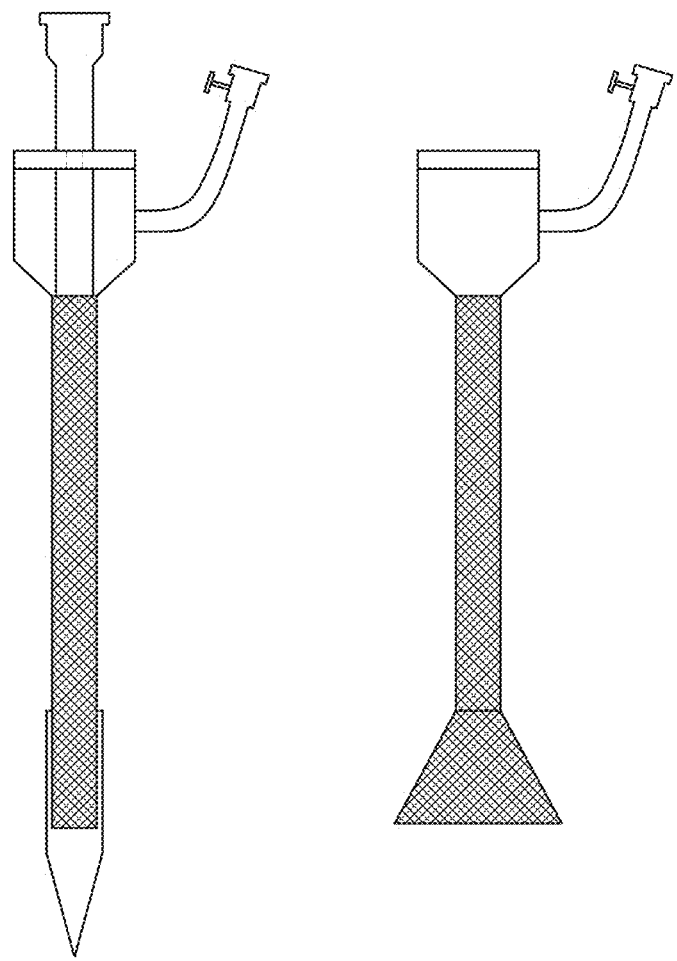
FIG. 24 illustrates an embodiment of an expandable funnel catheter.

FIG. 24 illustrates the funnel in a first configuration and a second configuration. The funnel can be delivered in a low profile configuration. The funnel can be expanded when delivered to the position within the body of the patient. The expandable funnel and the expandable shaft can be constrained for delivery. The system can include any feature to facilitate delivery. The system can include any feature to facilitate expansion.

FIGS. 25-29 illustrate a capture system 500 with a control handle to control the deploying of the tubular body and activate the tensioners. The control handle can be utilized with any system described herein. The capture system 500 can have any of the feature of the capture system 100 or any other system described herein. The capture system can have a nose tip 509. The capture system can have a guidewire lumen 508. The capture system can have a tubular body 507. The capture system can have one or more tensioners 505. The capture system can have a capture guide 506. The capture system can have a control knob 501. The control knob 501 can be moved to different positions. The capture system can have a pusher lock 502. The capture system can have a pusher rod 503. The capture system can have a flush port 504.

Figure 25:
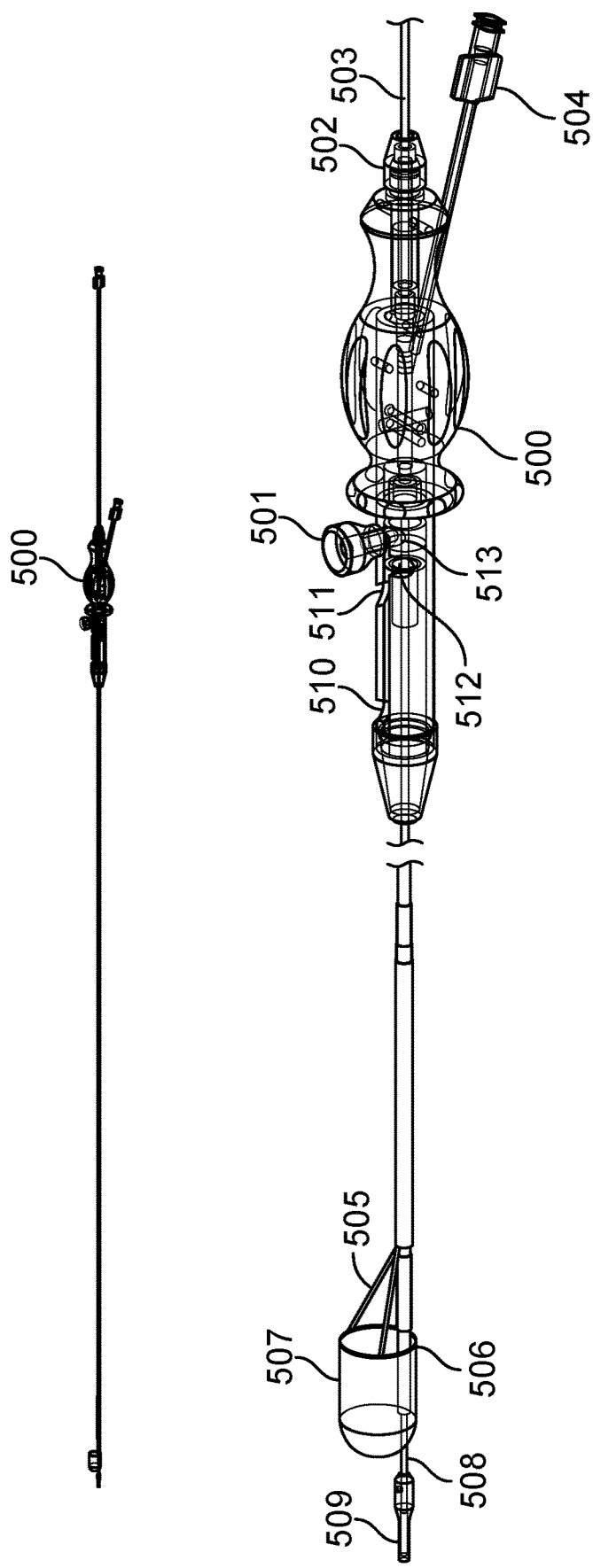
FIG. 25 illustrates a capture system with a control handle.
Figure 26:
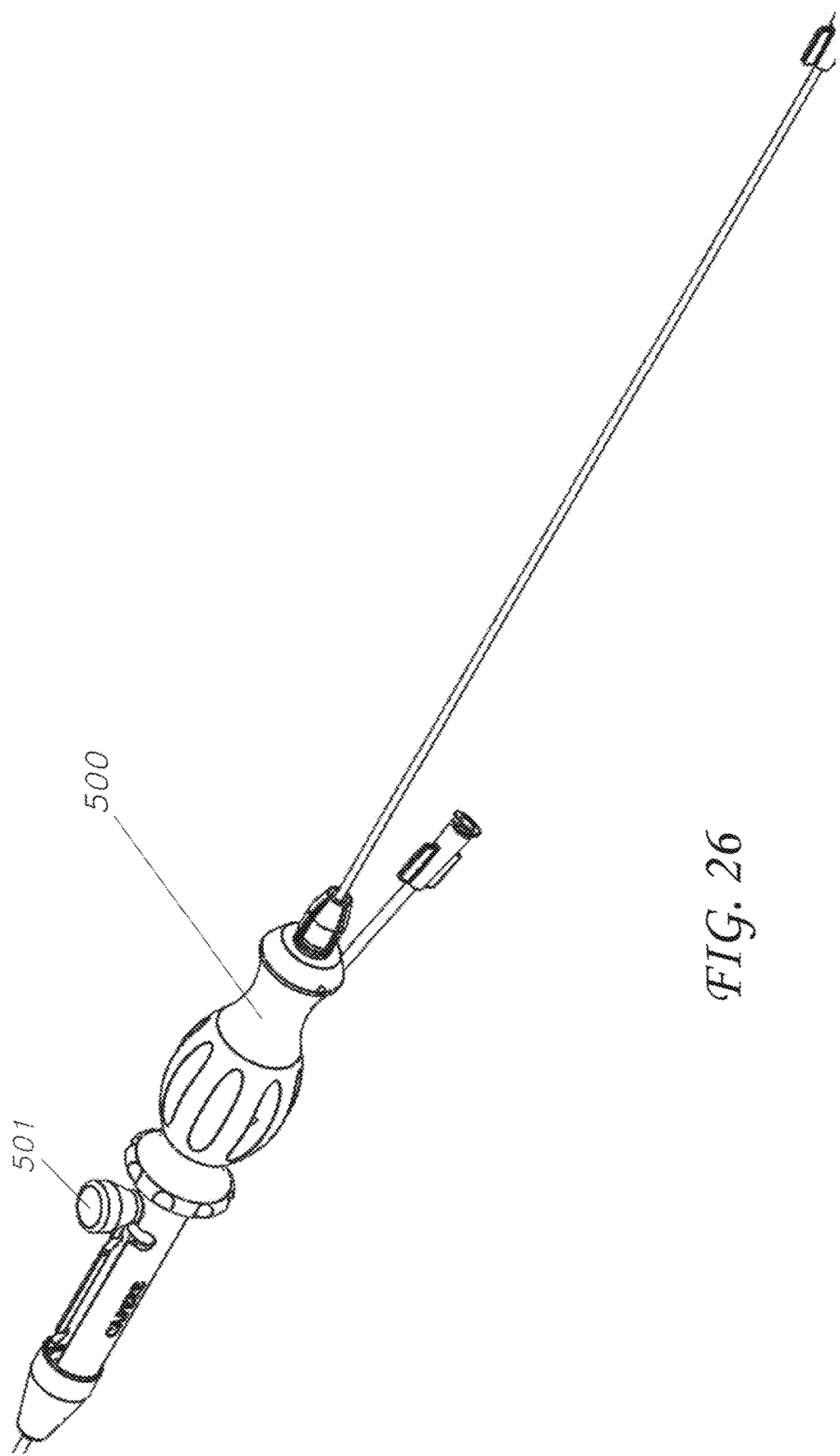
FIG. 26 illustrates the example capture system of FIG. 25.
Figure 27:
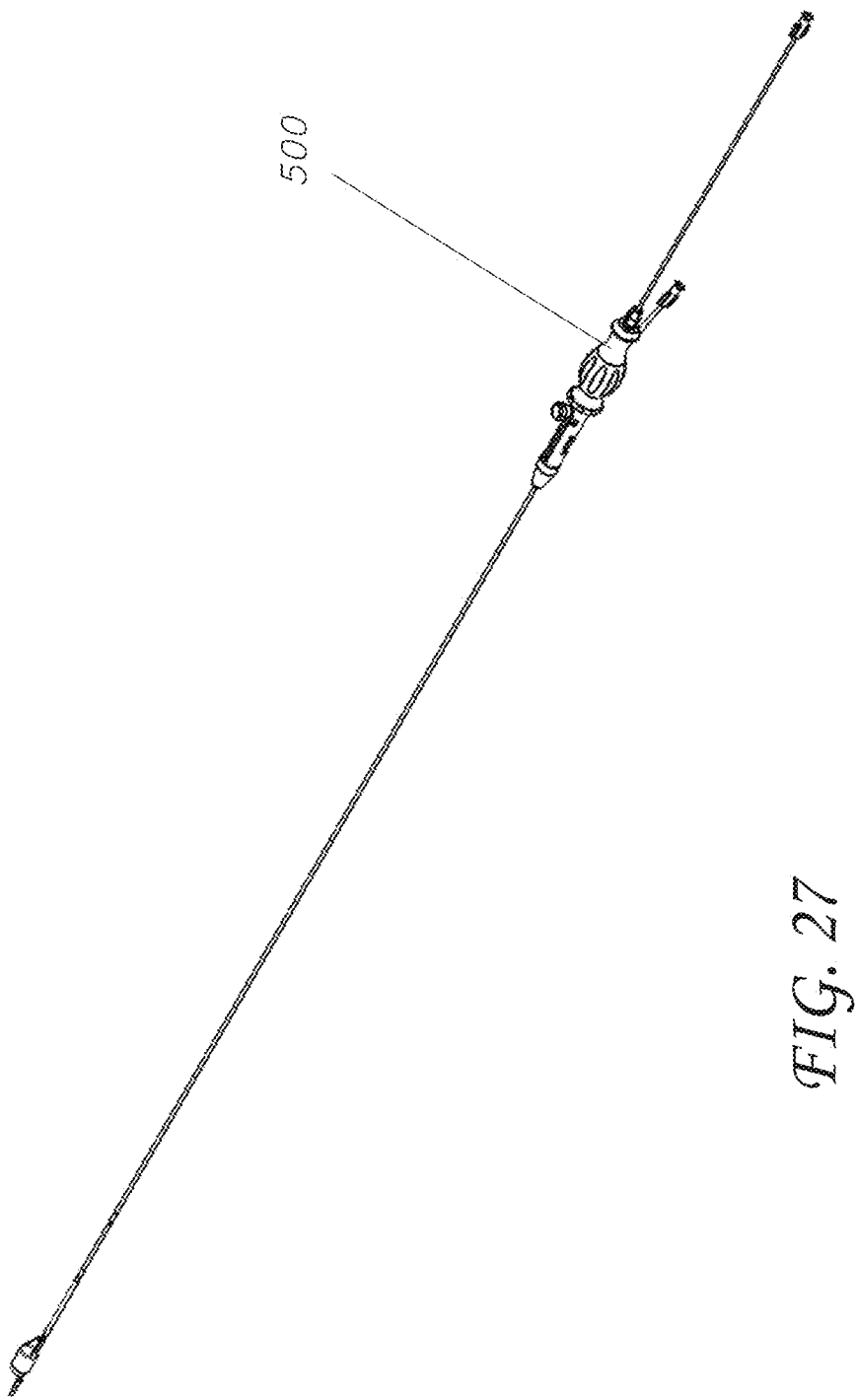
FIG. 27 illustrates the example capture system of FIG. 25.
Figure 28:
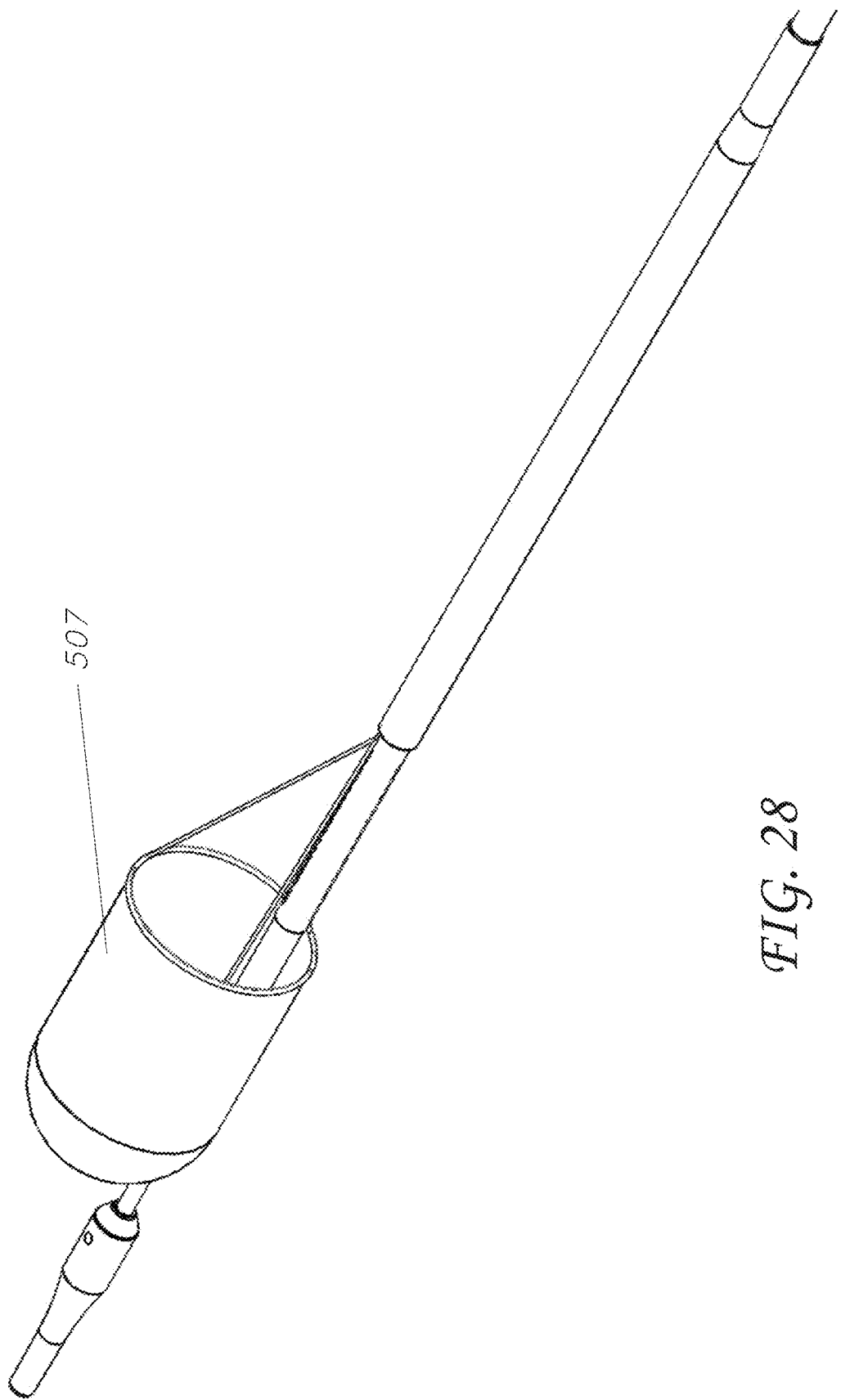
FIG. 28 illustrates the example capture system of FIG. 25.
Figure 29:
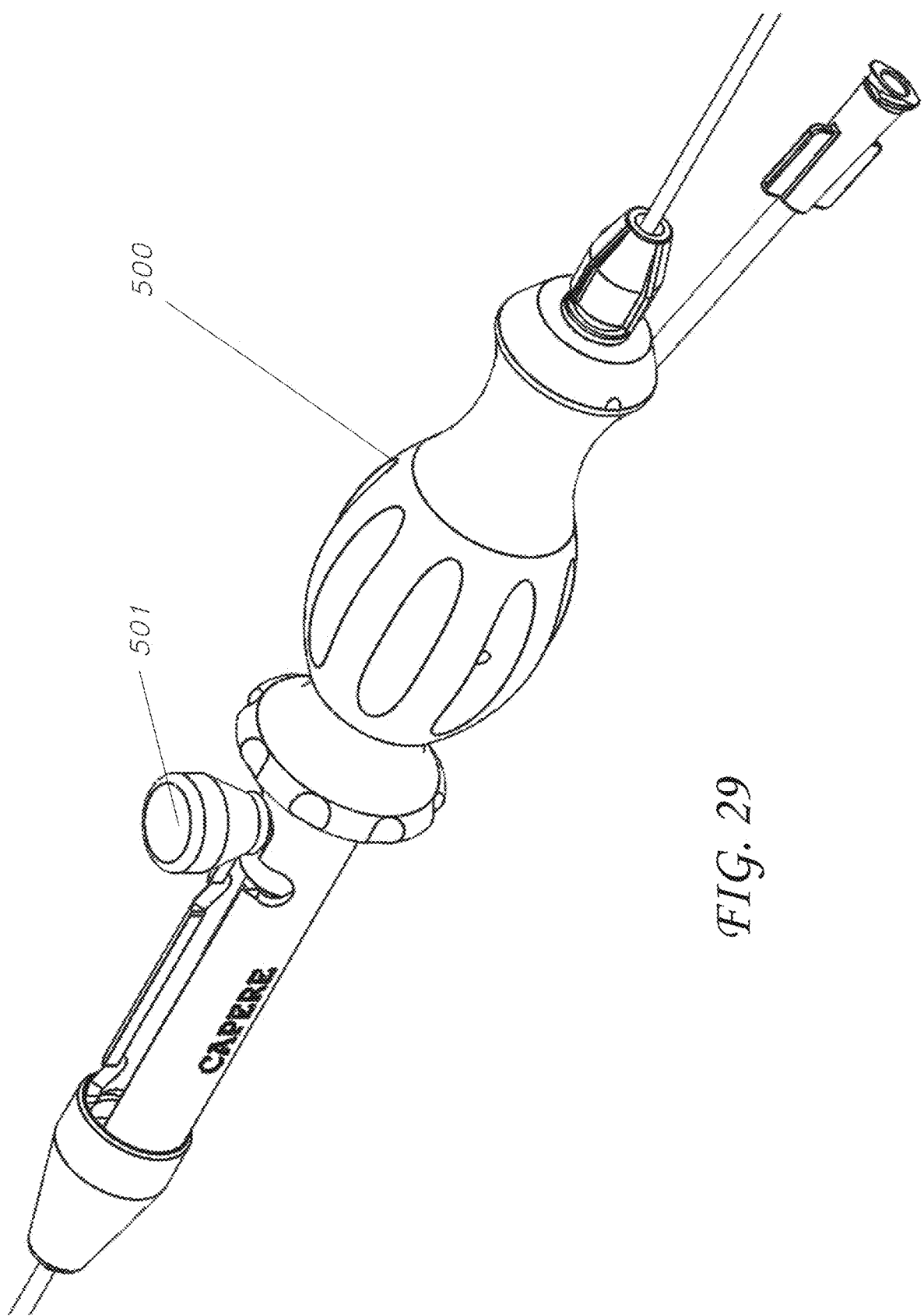
FIG. 29 illustrates the example capture system of FIG. 25.

When the control knob 501 is at the control handle position 510, this position indicates the tubular body 507 and the capture guide 506 are in the delivery configuration. When the control knob 501 is at the control handle position 513, this position indicates the tubular body 507 and the capture guide 506 are expanded and the one or more tensioners 505 are activated as shown in FIG. 25. When the control knob 501 is at the control handle position 511, this position indicates the tubular body 507 and the capture guide 506 are expanded and the one or more tensioners 505 are deactivated. When the control knob 501 is at the control handle position 512, this position indicates the tubular body 507 and the capture guide 506 are expanded and the one or more tensioners 505 have low tension. The positions 510, 511, 512, 513 change the deployment of the tubular body 507 and the capture guide 506. In position 510, the tubular body 507 and the capture guide 506 are in a low-profile configuration. In positions 511, 512, 513, the tubular body 507 and the capture guide 506 are expanded. The positions 511, 512, 513 change the tension of the one or more tensioners 505. In position 513, the tensioners are tensioned or have high tension. In position 512, the tensioners are in low tension. In position 512, the tensioners have low tension. In position 511, the tensioners are in little or no tension.

Figure 30B:
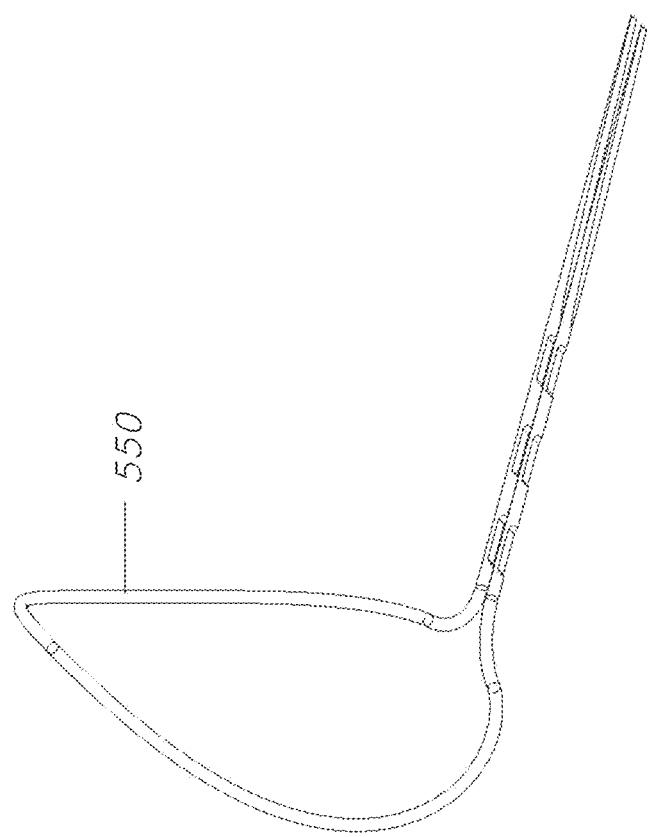
FIG. 30B illustrates the embodiment of the capture guide shown in FIG. 30A.
Figure 30A:
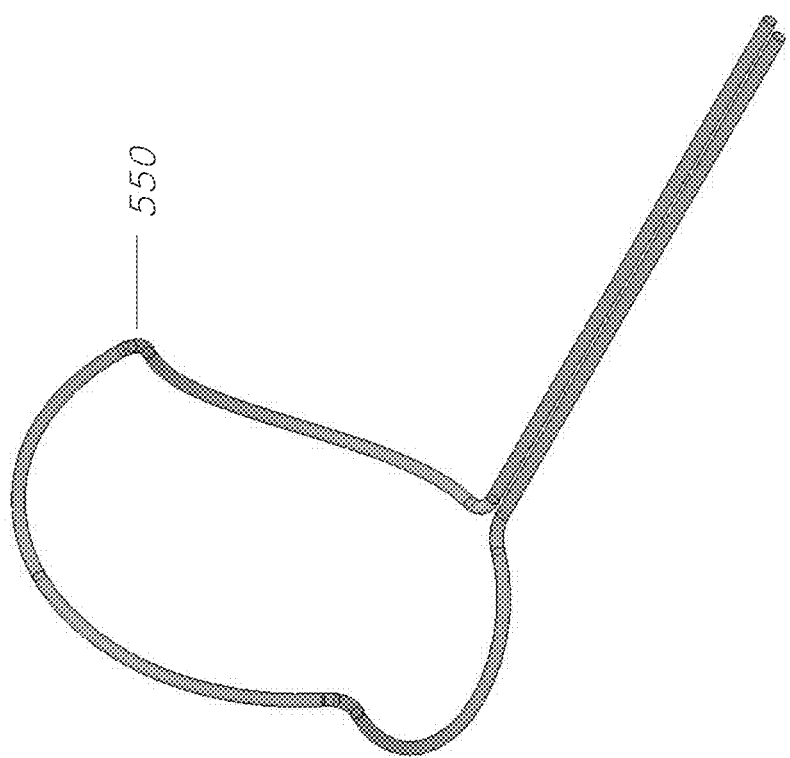
FIG. 30A illustrates an embodiment of a capture guide.

FIGS. 30A-30B illustrate embodiments of a capture guide 550. In some embodiments, the capture guide 550 comprises a pointed shape. In some embodiments, the capture guide 550 comprises a one point shape. In some embodiments, the capture guide 550 comprises a two point shape. In some embodiments, the capture guide 550 comprises a three point shape, see FIG. 7. The number of points can correspond to the number of tensioners. The tensioners can couple to the capture guide at the points. In some embodiments, the capture guide 550 comprises a non-linear shape. In some embodiments, the capture guide 166 comprises a wavy shape. In some embodiments, the capture guide 550 does not lie on a plane. In some embodiments, the capture guide 550 lies substantially on a plane. The capture can have different geometric configurations and bends along its circumference as shown in FIGS. 30A-30B. The bends can have an eyelet shape. The bend can be one or a plurality of bends along the capture guide circumference.

Figure 31:
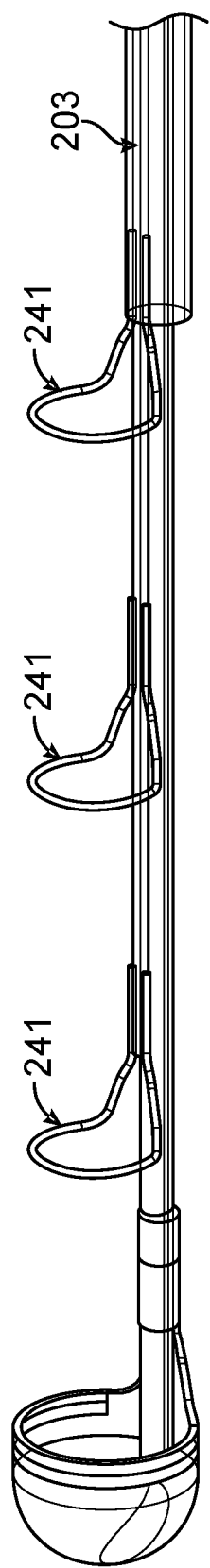
FIG. 31 illustrates a capture system including an anchor assembly.

FIG. 31 illustrates a capture system including an anchor assembly. The anchor assembly 221 can include about or at least about one, two, three, four, five, or more anchors 241 configured to secure a clot. One or more tensioners can couple to the one or more anchors 241. One or more tensioners can couple to the capture guide. One or more tensioners can couple to the one or more anchors 241 and the capture guide. Additional embodiments of capture systems can be found, for example, in U.S. Pat. No. 9,579,116 to Nguyen et al. issued Feb. 28, 2017, which is incorporated by reference in its entirety. Additional embodiments of capture systems can be found, for example, in U.S. Pat. No. 9,744,024 to Nguyen et al. issued Aug. 29, 2017, which is incorporated by reference in its entirety. Additional embodiments of capture systems can be found in U.S. Pat. No. 9,999,493 to Nguyen et al. issued Jun. 19, 2018 which is incorporated by reference in its entirety. In another embodiment, the tensioner's distal end can couple to the anchors or cutter 241 as shown in FIG. 31.

Figure 32A:
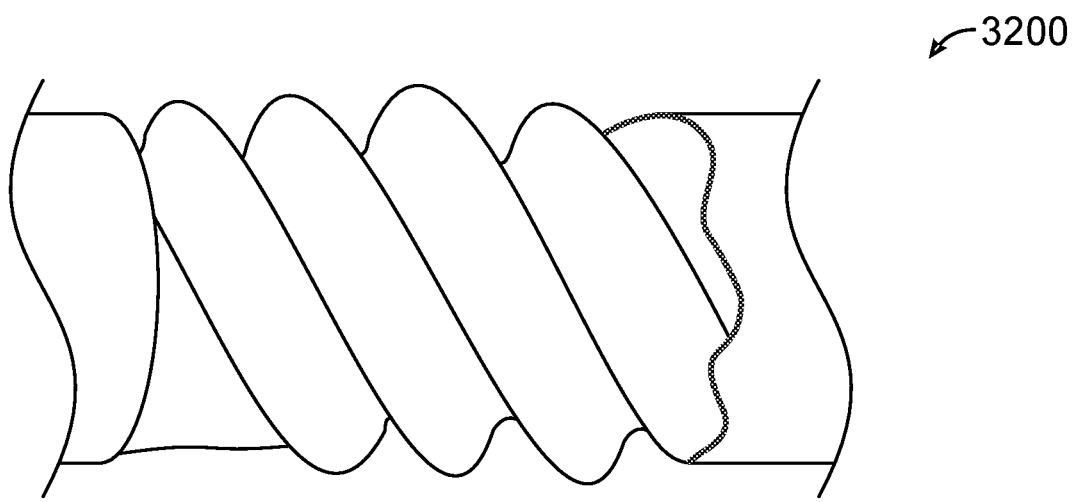
FIG. 32A illustrates a hemostasis seal assembly.
Figure 32B:
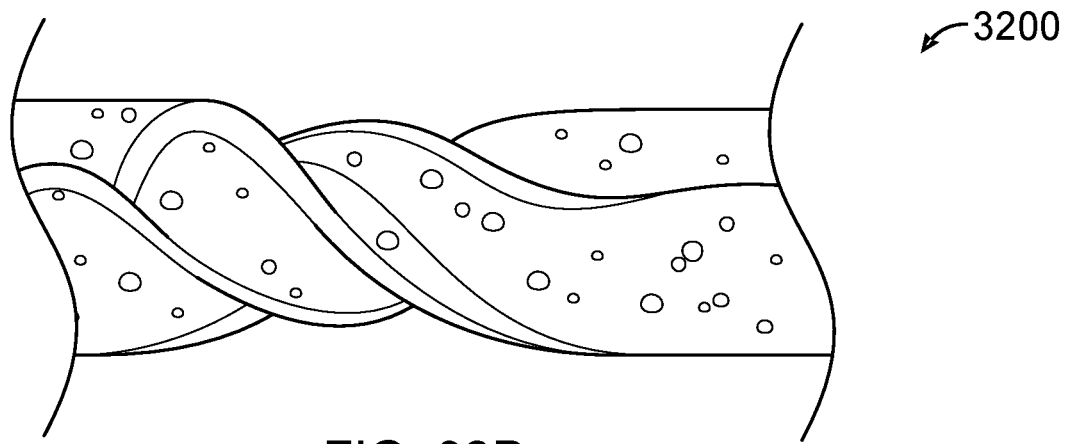
FIG. 32B illustrates the example hemostasis seal assembly of FIG. 32A.
Figure 32C:
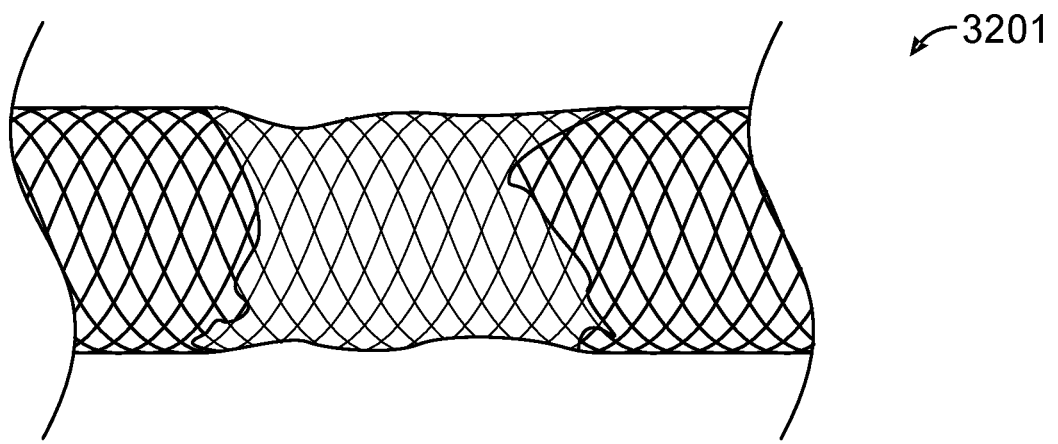
FIG. 32C illustrates the example hemostasis seal assembly of FIG. 32A.

FIGS. 32A-C illustrates a hemostasis seal assembly. In some embodiments, the hemostasis seal can be made of polymeric materials such as urethane or silicone. The hemostasis seal can include a tubular body and twist feature, such as a helical twist feature 3200. The twist feature allows the seal to be twist or rotate to reduce the inner diameter and close the inner lumen. The hemostasis seal tubular body can be reinforced with a frame such as a metallic or polymeric braid or coil or helix. The hemostasis seal is positioned or assembled with a housing or hub. The housing or hub can have a port for flushing or aspiration.

FIG. 33 illustrates a single suture 3300 configuration.

FIG. 34A-34C illustrates various forms of capture guide laser cut elements with struts. The capture guide can have one strut or a plurality of struts. The struts can be equal distance apart or non-equal distance apart. FIG. 34B indicates an element whereby allowing the struts to stretch under tensile stress. The element can also be a coil shape configuration.

FIG. 35 illustrates non-limiting different expandable funnel shaft configurations of laser cut patterns.

The expandable funnel catheter 200, 300, 400 can include the dilator 220, 220. The dilator can include an obturator 220, 320. The expandable funnel catheter 200, 300, 400 can include an expandable funnel sheath. The expandable funnel catheter 200, 300, 400 can include the expandable funnel tip 210, 310. The expandable funnel catheter 200, 300, 400 can include the expandable shaft 212, 312. The expandable funnel catheter 200, 300, 400 can include the peel-away cover 206, 306.

The dilator/obturator 220, 320 can function to aid in introducing the expandable funnel catheter 200, 300, 400 into the vasculature. The expandable funnel catheter 200, 300, 400 can functions to aid in the delivery of a device. In some embodiments, the device is a capture system including a tubular body. The tubular body is designed to axially lengthen. In some embodiments, the tubular body is configured to roll out, invert, evert, and/or variably lengthen proximally from the first configuration to the second configuration.

The expandable funnel catheter 200, 300, 400 can allow large volume of collected emboli, thrombi, or foreign materials to pass through easily. The collected emboli, thrombi or foreign materials is retracted into the expandable funnel catheter 200, 300, 400. The expandable funnel catheter 200, 300, 400 is expanded as needed in order to allow large volume of collected emboli, thrombi, or foreign materials to pass through. The peel-away cover 206, 306 can function to contain the expandable funnel catheter 200, 300, 400.

In some embodiments, the expandable funnel catheter 200, 300, 400 is constructed of a dual braid wire or plurality for wire filaments. In some embodiments, both ends terminate at the proximal end of the body of the expandable funnel catheter 200, 300, 400. In some embodiments, one braid end extends distally to the tip of the funnel and folds back and the second braid end extends from the fold back proximally to the body proximal end. The expandable funnel tip 210, 310 can include two layers of braided mesh. The expandable funnel tip 210, 310 can be folded over and coupled to the end of the expandable shaft 212, 212.

In some embodiment, the funnel catheter body is delivered in a single layer where the inner layer is extending distally to the outer layer. Upon removing the obturator, the braid end of the inner layer is inverting back inside the outer layer proximally to create the inner layer underneath the outer. The funnel portion is expanded when the inner layer is fully retracted to the proximal end.

In some embodiments, the expandable funnel catheter 200, 300, 400 has an inner portion and an outer portion. The inner portion can be slidable to expand the funnel tip. The inner portion can be slidable to collapse the funnel tip. The outer portion can be slidable to expand the funnel tip. The outer portion can be slidable to collapse the funnel tip.

The distal end is formed to shape a funnel like opening. In some embodiment, the distal end can have the same, larger or smaller than the opening as the body. The proximal end is formed with an opening to couple to a housing or the first hub 202, 302 with hemostasis seal and a flushing/aspiration port 214, 314. The proximal end opening can have same opening as the body or larger opening in some embodiment than the body opening.

The expandable funnel catheter 200, 300, 400 dual braid layers can be coated with polymeric materials. In some embodiments, the body such as the expandable shaft 212, 312 of the expandable funnel catheter 200, 300, 400 can be coated. In some embodiments, the funnel portion such as the expandable funnel tip 210, 310 can be noncoated. In some embodiment, the expandable funnel tip 210, 310 and expandable shaft 212, 312 are coated. In some embodiment, both the outer layer and the inner layer can be coated. In some embodiment, the inner layer is coated. In some embodiment, the outer layer is coated.

The body of the expandable funnel catheter 200, 300, 400 is coupled to the housing or the first hub 202, 302. The first hub 202, 302 can include a hemostasis seal. The first hub 202, 302 can include a port 214, 314 that can be used for either flushing and/or aspiration.

In some embodiments, the expandable funnel catheter 200, 300, 400 can have a braided shaft extending the entire length. The expandable funnel section can be up to the entire catheter length. The expandable funnel section can be about, e.g., 4 cm to 35 cm in length. The catheter can be expandable from the distal end all the way to the percutaneous entry point of the catheter. The outer diameter can range from, e.g., 4 F to 30 F. The inner diameter can range from, e.g., 3 F to 28 F. The expanded length section can be up to the entire catheter length. In some embodiments, the length can be about 4 cm to 35 cm. The funnel and shaft can be made as one component wherein the braided configuration is continuous. The shaft can be coupled to or continuous with the funnel tip. The braided shaft can have a funnel at the distal end. The expandable shaft 212, 312 and the expandable funnel tip 210, 310 can be integrated. The expandable shaft 212, 312 and the expandable funnel tip 210, 310 can form a unitary braided structure. The expandable shaft 212, 312 and the expandable funnel tip 210, 310 can be one contiguous member. The expandable shaft 212, 312 and the expandable funnel tip 210, 310 can be two separate members. The braid configuration can be a single wire or a plurality such as 8, 16, 32, 48, 288, or any range of the foregoing values.

The expandable shaft 212, 312 and the expandable funnel tip 210, 310 can be expanded from one diameter to a larger diameter. The expandable shaft 212, 312 and the expandable funnel tip 210, 310 can be expanded upon receiving a device, such as a capture device. The expandable shaft 212, 312 and the expandable funnel tip 210, 310 can be expanded upon receiving an emboli, foreign body, clot and/or thrombus.

The expandable shaft 212, 312 can include two braided layers. The expandable funnel tip 210, 310 can include two or more braided layers. The braided layers can be made of metallic wires such as nitinol or stainless steel or polymeric wires or filaments such as nylon, Polyester, PEEK, polyamides, and/or combinations thereof. The braided layers can be coated with polymeric material such as urethane or silicone. The outer braided layer can be coated. The inner braided layer can be coated. Both the outer and inner braided layer can be coated. The braid wire can have diameter from 0.0003" to 0.015". The braid pattern can be 1×1, 2×2, paired wire 1×1, paired wire 2×2, or any combination thereof.

The expandable funnel tip 210, 310 can be composed of either metallic or polymeric wires or filaments. The braided funnel can have two layers, an inner and outer layer. The inner and outer layer can be contiguous. The inner layer can extend from the proximal end to the distal end of the funnel sheath/catheter where it folds and transition to the outer layer and extend overlapping the inner layer. The expandable funnel tip 210, 310 can be coated with polymeric materials or uncoated. In some embodiments, the expandable funnel tip 210, 310 is uncoated.

The expandable funnel catheter 200, 300, 400 can be composed of a braid shaft and braid funnel extending from proximal end to the funnel end. The expandable funnel catheter 200, 300, 400 can be expanded from one diameter at one configuration to another configuration when a device, foreign material, emboli or thrombi, clot or thrombus is inside the expandable funnel catheter 200, 300, 400. The braid shaft and funnel can comprise a dual braid layer, inner and outer layer, extending from the proximal end to the distal end. The braid shaft outer layer can be coated or covered with material that allow the braid shaft to expand. The braid can be composed of Nitinol material in some embodiments. The braid inner and outer layer can be contiguous wherein the first end begins at the inner layer proximal end and extends distally to the tip of the funnel and fold or transition into the outer layer and extends proximally to the proximal end of the outer layer. The braid wire diameter can range from 0.0003" to 0.015". The wire can be round or flat (1×3, 2×4, 3×5 etc.) The braid pattern can be 1×1, 2×2 or 1×2 configuration.

The expandable funnel catheter can include a laser cut shaft. The laser cut funnel and shaft can have a geometric pattern that allow the laser cut shaft to expand. The funnel shaft can be coated with polymeric materials such as, e.g., urethane or silicone.

In some embodiments, the inner and outer layer of the braid shaft and the funnel can be coated or covered with polymeric material. In some embodiments, the inner layer of the braid shaft and funnel is coated and the outer layer of the braid shaft and funnel is not coated with polymeric material. In some embodiments, the inner layer of the braid shaft and the funnel inner and outer layer is not coated but only the outer layer of the braid shaft is coated. In some embodiments, the inner layer of the braid shaft and funnel is not coated, the outer layer of the braid shaft and funnel is coated. In some embodiments, when the inner layer braid shaft and funnel is not coated and the outer braid layer is coated and either the funnel outer layer is coated or uncoated, the uncoated inner layer braid shaft and funnel can be fixed or axially and/or radially movable. When the inner layer braid shaft and funnel axially and/or radially movable, the funnel can be collapsed. In some embodiments, the expandable funnel tip 210, 310 is fixed. In some embodiments, the expandable funnel tip 210, 310 is axially movable. In some embodiments, the expandable shaft 212, 312 is fixed. In some embodiments, the expandable shaft 212, 312 is axially or radially movable.

The braid shaft is connected to the hub 202 with hemostasis seal. The braid shaft funnel can be assembled with the dilator/obturator 220, 320 and the outer sheath or cover 206, 306. The cover 206, 306 can function to contain braid shaft and collapse the funnel during introduction in the vessel. Once inside the vessel, the cover 206, 306 can be peeled away to expand the expandable funnel tip 210, 310 and expandable shaft 212, 312. The obturator is inserted into the lumen of the funnel catheter to access the vessel. The outer sheath can compose of polymeric materials for example FEP, PTFE, PET, Pebax, Polyurethane or Silicone.

In some embodiments, the expandable funnel catheter 200, 300, 400 can have a funnel distal end and shaft body. The shaft body can have a composite structure wherein the inner layer is polymeric materials, the middle layer is metallic structure of either braid or stent-like structure, or laser cut geometric patterns (diamond, cell open structure, connecting z pattern) that can radial expand or contract and an outer layer of polymeric materials. The polymeric materials have sufficient rigidity to introduce into the vascular system and is able to expand upon encountering a large volume of material such as emboli, thrombi or clot thrombus or foreign materials.

In some embodiments, the body of the expandable funnel catheter 200, 300, 400 is a composite wherein the inner layer is made of low coefficient materials such as PTFE, polyamide, nylon, polyethylene, High Density Polyethylene and an outer layer made of low durometer polymeric material to allow expansion upon encountering large material. The inner layer is constructed to allow fold and/or overlap to enable the inner layer to slide or open more easily. In some embodiment, the inner layer has one slit along the length of catheter body. In some embodiment, the inner layer has two slits along the length of the catheter body. In some embodiment, the inner layer has a plurality of slits, for example three slits, along the catheter body. The outer layer is made of polymeric materials that can expand and contract. In some embodiment, the inner layer slit ends overlap each other. In some embodiment, the inner layer has either single fold or multiple folds such as two or three.

Various methods of use can accomplish using the expandable funnel catheter 200, 300, 400 with the thrombectomy system. In some embodiments, the method can include introducing the assembled expandable funnel catheter 200, 300, 400 into the vessel over the guidewire. The peel-away cover 206, 306 is then removed to deploy the expandable funnel tip 210, 310 and expandable shaft 212, 312. The obturator is then removed from the expandable funnel tip 210, 310 and expandable shaft 212, 312. The thrombectomy system can be introduced over the guidewire and through the expandable funnel tip 210, 310 and expandable shaft 212, 312 to the intended occluded treatment area. The area is thrombectomized to remove and collect the clot. As a thrombectomy catheter, balloon, basket, or collection bag deployed distally to the clot then pull the clot proximally, the expandable funnel tip 210, 310 acts as a barrier to stop embolies or unwanted materials moving proximally. A syringe can attach to the aspiration port 214, 314 of the expandable funnel catheter 200, 300, 400 to aspirate the clot as the clot gather into the funnel. Continue collecting a large clot volume into the funnel sheath will enable the expandable shaft 212, 312 to expand as the large clot volume passes through the expandable shaft 212, 312. The expandable funnel catheter 200, 300, 400 can be utilized with any capture system described herein.

In some embodiments, the expandable funnel catheter 200, 300, 400 does not include the expandable funnel tip 210, 310 at distal end. The expandable funnel catheter 200, 300, 400 can be used as a low profile for introduction sheath then the profile be able to expand to comply to bigger profile of other therapeutic devices such as stent delivery, percutaneous valve delivery, kidney stone removal.

The expandable funnel catheter 200, 300, 400 can include an expandable distal end, configured to be positioned away from a user, within a body of a patient. The expandable funnel catheter 200, 300, 400 or at least the distal end, can feature at least a dual braid layer including an outer layer and an inner layer. In some embodiments, the expandable funnel catheter 200, 300, 400 can include a dual layer structure. In some embodiments, the expandable funnel catheter 200, 300, 400 can include an outer braid layer. In some embodiments, the outer braid layer is coated with a material such as one or more polymeric materials. In some embodiments, the expandable funnel catheter 200, 300, 400 can include an inner braid layer. In some embodiments, the inner braid layer is not coated with a polymeric material. In some embodiments, a portion of the inner braid layer is not coated. In some embodiments, a distal portion of the inner braid layer is not coated. In some embodiments, a length of the inner braid layer is not coated. In some embodiments, the entire length of the inner braid layer is not coated. In some embodiments, a portion of the outer braid layer is coated. In some embodiments, a distal portion of the outer braid layer is coated. In some embodiments, a length of the outer braid layer is coated. In some embodiments, the entire length of the outer braid layer is coated. In some embodiments, the outer braid layer remains coated or encased with the polymer during the procedure.

In some embodiments, the outer braid layer is coated with a polymer. The polymer can be any material including, for example, Pellethane, Silicone, Tecoflex, Tecothane, Latex, Pebax, and combinations thereof. The polymer can function akin to a slip layer. The polymer can facilitate the sliding of the catheter against a target vessel. In some embodiments, the inner braid layer is not coated with a polymer, instead, retains the mesh-like structure as shown. The inner braid layer advantageously provides decreased surface area, decreased surface contact, and/or decreased friction relative to an object within the lumen of the catheter. For instance, the mesh-like structure of the inner braid layer has less surface area to contact the object within the lumen than a solid, inner wall. The inner braid layer allows for a retrieval catheter, one or more tools, materials, or the capture system 100, 500 to more easily slide axially when withdrawn proximally through the lumen. In some methods of use described herein, the capture system 100, 500 can be axially lengthened over one or more materials before retraction into the expandable funnel catheter 200, 300, 400. In some methods of use described herein, the capture system 100, 500 can be axially lengthened over an obstruction such as a clot before retraction into the expandable funnel catheter 200, 300, 400. In some methods of use described herein, the capture system 100, 500 can provide distal protection to prevent the loss of material as the capture system 100, 500 is retracted into the expandable funnel catheter 200, 300, 400.

In some embodiments, the expandable funnel catheter 200, 300, 400 has a funnel shape at the distal end. In some embodiments, distal refers to the portion of the expandable funnel catheter 200, 300, 400 or component thereof, which is furthest from the user during use, while proximal refers to the portion of the expandable funnel catheter 200, 300, 400 or component thereof which is closest to the user. In some embodiments, the distal end of the expandable funnel catheter 200, 300, 400 is positioned within the body of the patient and the proximal end is outside the body of the patient.

In some embodiments, the expandable funnel catheter 200, 300, 400 can include any of the features of the capture system 100, 500 described herein. In some embodiments, the mesh can be made from metallic materials such as individual non-elastic wires. In some embodiments, the mesh can be made from elastic elements. In some embodiments, the mesh can be made from a combination of elastic and non-elastic wires. In some embodiments, the dual braid can be made of either polymeric or metallic materials. In some embodiments, the metallic materials can be Nitinol, stainless steel, steel, shape memory alloy, elastic alloy, Nickel Titanium alloy, etc. In some embodiments, the braid wire diameter can range from 0.0005" to 0.030", e.g., 0.0005", 0.001", 0.0015", 0.002", 0.0025", or 0.003", between 0.0005"–0.0015", between 0.001"–0.002", between 0.0015"–0.0025", between 0.002"–0.003" etc. Other configurations of braid wire diameter are contemplated. The braid wire can be woven in any pattern. In some embodiments, the expandable funnel catheter 200, 300, 400 can include at least one polymer layer. The at least one polymer layer can applied to any surface of the braid wire. The braid wire can include one or more woven patterns, for instance a first wave pattern in a first portion of the expandable funnel catheter 200, 300, 400 and a second wave pattern in a second portion of the expandable funnel catheter 200, 300, 400. The woven pattern can be a typical over under pattern, e.g., two over, two under; one over, one under, etc. The woven paten can from a tubular braid. In some embodiments, the expandable funnel catheter 200, 300, 400 can include multiple layers of braid wire.

The braid wire can form a mesh. In some embodiments, the cross-section of the wire can be any shape including round, polygonal, elliptical, etc. The shape of the wire can be flat, square, ribbon, round, etc. In some embodiments, the total braid angle can range from 10 degrees to 170 degrees. In some embodiments, the total braid angle is 0 degrees, 10 degrees, 20 degrees, 30 degrees, 40 degrees, 50 degrees, 60 degrees, 70 degrees, 80 degrees, 90 degrees, 100 degrees, 110 degrees, 120 degrees, 130 degrees, 140 degrees, 150 degrees, 160 degrees, 170 degrees, 180 degrees, between 0-45 degrees, between 45-90 degrees, between 90-135 degrees, between 135-180 degrees, etc. In some embodiments, the braid density can range from 5 PPI to 60 PPI. In some embodiments, the braid density is less than 5 PPI, 5 PPI, 10 PPI, 15 PPI, 20 PPI, 25 PPI, 30 PPI, 35 PPI, 40 PPI, 45 PPI, 50 PPI, 55 PPI, 60 PPI, 65 PPI, 70 PPI, 75 PPI, 80 PPI, between 0-20 PPI, between 20-40 PPI, between 40-60 PPI, between 60-80 PPI, etc. In some embodiments, the inner diameter can range from 1 F to 30 F. In some embodiments, the inner diameter is less than 1 F, 1 F, 2 F, 3 F, 4 F, 5 F, 6 F, 7 F, 8 F, 9 F, 10 F, 11 F, 12 F, 13 F, 14 F, 15 F, 16 F, 17 F, 18 F, 19 F, 20 F, 21 F, 22 F, 23 F, 24 F, 25 F, 26 F, 27 F, 28 F, 29 F, 30 F, 31 F, 32 F, 33 F, 34 F, 35 F, between 0 F-5 F, between 5 F-10 F, between 15 F-20 F, between 20 F-25 F, between 25 F-30 F, between 30 F-35 F, etc. In some embodiments, the outer diameter can range from 2 F up to 33 F. In some embodiments, the outer diameter is less than 1 F, 1 F, 2 F, 3 F, 4 F, 5 F, 6 F, 7 F, 8 F, 9 F, 10 F, 11 F, 12 F, 13 F, 14 F, 15 F, 16 F, 17 F, 18 F, 19 F, 20 F, 21 F, 22 F, 23 F, 24 F, 25 F, 26 F, 27 F, 28 F, 29 F, 30 F, 31 F, 32 F, 33 F, 34 F, 35 F, between 0 F-5 F, between 5 F-10 F, between 15 F-20 F, between 20 F-25 F, between 25 F-30 F, between 30 F-35 F, etc.

In some embodiments, the expandable funnel catheter 200, 300, 400 can include the expandable shaft 212, 312. In some embodiments, the expandable funnel catheter 200, 300, 400 can include a shaft that expands under compression. In some embodiments, the expandable funnel catheter 200, 300, 400 can include a shaft that lengthens under compression. In some embodiments, the expandable funnel catheter 200, 300, 400 can include a shaft that expands upon release of a constraint. In some embodiments, the expandable funnel catheter 200, 300, 400 can include a shaft that expands due to temperature. In some embodiments, the expandable funnel catheter 200, 300, 400 can include a shaft that expands to assume a neutral configuration.

In some embodiments, the expandable funnel catheter 200, 300, 400 can include an inverted structure. In some embodiments, one end of the braid begins at the proximal end and extends to the distal end where it folds inward and extends back to the proximal end. In some embodiments, the dual braid extends from the proximal end to the distal end. In some embodiments, the braid at the distal end can be continuous. In some embodiments, the braid at the distal end can be discontinuous. In some embodiments, one end of the braid begins at the proximal end and extends to the distal end wherein it folds inward and extends back to the proximal region. In some embodiments, one end of the braid begins at the proximal end and extends to the distal end wherein it folds outward and extends back to the proximal region. The outer braid layer and the inner braid layer are concentric.

In some embodiments, the outer layer braid is encapsulated with polymeric materials. In some embodiments, the polymer layer can have uniform wall thickness. In some embodiments, the polymer layer can have uniform density. In some embodiments, the polymer layer can have uniform wall thickness throughout the entire catheter length. In some embodiments, the polymer layer can have non-uniform wall thickness. In some embodiments, the proximal end of the catheter wall thickness is thicker than the wall thickness at the distal end. In some embodiments, the polymeric material can have the same softness (durometer) through the catheter length. In some embodiments, the polymeric material can have different or a variety of softness (durometer) through the catheter length. In some embodiments, the polymeric material is expandable. In some embodiments, the polymeric material is flexible. In some embodiments, the outer layer composite is expandable. In some embodiments, polymeric materials can be any elastomer materials such as Polyurethane, Pellethane, Silicone, Tecoflex, Tecothane, Latex, Pebax and/or combination thereof. In some embodiments, the polymer can be coupled to the braid material through any methods known in the art. In some embodiments, the polymer can be coated, molded, dipped or thermally fused onto the braid.

In some embodiments, the expandable funnel catheter 200, 300, 400 has a funnel shape at distal end. In some embodiments, the guide catheter outer braid is encapsulated from the proximal end to the distal end near the funnel. In some embodiments, the funnel outer and inner braid layer is not encapsulated with polymer. In some embodiments, the funnel outer braid is encapsulated with polymer. In some embodiments, the inner braid layer can be encapsulated with polymer and the outer layer is not.

The expandable funnel catheter 200, 300, 400 can function as an access system. In some embodiments, the expandable funnel catheter 200, 300, 400 is introduced in a compressed diameter configuration. In some embodiments, after introduction, the expandable funnel catheter 200, 300, 400 may be radially expanded to accommodate passage of larger diameter surgical instruments therethrough such as capture system and/or the anchors described herein.

The expandable funnel catheter 200, 300, 400 can be useful for forming and enlarging access area in target locations within a patient's body. In some embodiments, the expandable funnel catheter 200, 300, 400 is delivered in a small diameter configuration and expanded. In some embodiments, only a distal end or a funnel end is expanded. In some embodiments, the expandable funnel catheter 200, 300, 400 can change the size of the lumen that the expandable funnel catheter 200, 300, 400 is inserted into, such as enlarging a vessel by pressing against the vessel wall. The expandable funnel catheter 200, 300, 400 can include a polymeric coating that facilitates sliding contact with the vessel wall.

In some embodiments, passage of the capture system 100, 500 through the expandable funnel catheter 200, 300, 400 can cause expansion of the expandable funnel catheter 200, 300, 400. In some embodiments, the collapsed capture system 100, 500 can be sized to fit within the expandable funnel catheter 200, 300, 400. In some embodiments, the expanded capture system can be sized to fit within the expandable funnel catheter 200, 300, 400. In some embodiments, the expanded capture system 100, 500 can be retracted through the expandable funnel catheter 200, 300, 400. In some embodiments, the one or more materials can be retracted through the expandable funnel catheter 200, 300, 400. In some embodiments, the one or more tools can be sized to fit within the expandable funnel catheter 200, 300, 400. The uncoated inner braid layer reduces sliding contact between the expandable funnel catheter 200, 300, 400 and any components passed therethrough.

In some embodiments, the expandable funnel catheter 200, 300, 400 can function as a variable sized cannula. In some embodiments, the expandable funnel catheter 200, 300, 400 can function as a tissue dilator. In some embodiments, the expandable funnel catheter 200, 300, 400 can change shape during axial compression of the braid. In some embodiments, axial shortening can cause radial expansion of the expandable funnel catheter 200, 300, 400. In some embodiments, the expandable funnel catheter 200, 300, 400 can be variably expanded based on the amount of compressive force. In some embodiments, the expandable funnel catheter 200, 300, 400 is self-expanding. In some embodiments, the expandable funnel catheter 200, 300, 400 is expanded by a mechanism e.g., pull strings, release from a constraint, application of compressive force, application of tension, etc. In some embodiments, the expandable funnel catheter 200, 300, 400 is a shape memory material.

In some embodiments, the expandable funnel catheter 200, 300, 400 can facilitate the removal of a blockage within the vasculature of a patient. In some embodiments, the expandable funnel catheter 200, 300, 400 can surround the capture system 100, 500 that is entangled in the clot. In some embodiments, the surface of the clot can slide easily within the expandable funnel catheter 200, 300, 400, due in part, to the inner surface of the expandable funnel catheter 200, 300, 400. In some embodiments, the expandable funnel catheter 200, 300, 400 can slide easily within the target vessel, due in part, to the outer surface of the expandable funnel catheter 200, 300, 400. In some embodiments, the expandable funnel catheter 200, 300, 400 can be collapsed after receiving the capture system 100, 500, material, and/or tool. In some embodiments, the expandable funnel catheter 200, 300, 400 can surround the captures system 100, 500 which itself encapsulates the material. In some embodiments, the outer surface of the capture system 100, 500 can slide easily within the expandable funnel catheter 200, 300, 400, due in part, to the inner surface of the expandable funnel catheter 200, 300, 400. In some embodiments, the expandable funnel catheter 200, 300, 400 can be collapsed after receiving the capture system 100, 500.

In some methods of use, the capture system 100, 500 is used in combination with a thrombectomy catheter, such as an AngioJet® thrombectomy device or potentially an aspiration catheter may be used to remove the embolic debris. In some methods of use, one or more anchors described herein is used in combination with a thrombectomy catheter or an aspiration catheter, such as an AngioJet® thrombectomy device. The use of the AngioJet®, a rheolytic cross stream thrombectomy catheter, can include an inherent ability to remove thrombus of larger diameter than the catheter's diameter. However, the disruptive strength of the device falls off with the radial distance from the catheter. Hence, at some radial distance the clot can be stronger than the disruptive force generated by the AngioJet® cross stream flow patterns. In the case of organized thrombus, this radial distance from the catheter can be smaller than for softer thrombus.

Water jet thrombectomy procedures in general can be limited in ability in some cases. However, adding mechanical disruption such as by use of the anchors described herein can unexpectedly and synergistically improve water jet ablation. By combining mechanical agitation, e.g., abrasive intimate contact of thrombus by a flexible and expandable anchor component and the capture system 100, 500 with a rheolytic thrombectomy catheter (AngioJet®), a variety of thrombus can be cleared than can be cleared by mechanical agitators or rheolytic cross stream thrombectomy catheters individually.

Another aspect and feature of some embodiments of the devices of the present disclosure is a device having the ability to capture large and small embolic debris. Another aspect and feature of the devices of the present disclosure is a device having the ability to temporarily capture debris which may later be removed by manual aspiration or by the use of an AngioJet® thrombectomy device and catheter or which may be treated by thrombolytics. Another aspect and feature of the devices of the present disclosure is a device having the ability to macerate debris to a clinically insignificant size (depending on the area of the body) or to a size which can be pharmacologically treated or removed by another device, such as an AngioJet® thrombectomy device and catheter. Another aspect and feature of the devices of the present disclosure is a device having the ability to macerate non-embolic debris, such as a stationary thrombus, by pulling the device through such an obstruction.

An intravascular ultrasound (IVUS) transducer can be incorporated into the systems described herein. In some embodiments, an intravascular ultrasound (IVUS) transducer can be added to or incorporated into the delivery system and method. A pressure sensor can be used to measure the pressure at various positions within the vasculature, which can be used to determine blood flow, while the intravascular ultrasound (IVUS) transducer can be used to measure fluid flow and/or provide imaging within the vessel. In some embodiments, the pressure sensor and/or IVUS transducer can be incorporated into the guidewire at one or more locations, such as the distal end or distal portion of a guidewire, as well as being incorporated into intermediate and proximal portions of the guidewire. The guidewire with the pressure sensor and/or the IVUS transducer can be used much like a normal guidewire to help navigate the delivery device through the vasculature, with the added benefit of providing pressure measurements and ultrasound imaging to help in the navigation, to visualize the device placement site, and to monitor and ensure proper device deployment. In some embodiments, the IVUS transducer generates image slices as it is advanced and retracted which can then be assembled together to form a three dimensional reconstruction of the vasculature and/or the device within the vasculature. In some embodiments, the guidewire with the pressure sensor and/or IVUS transducer can be fastened to a catheter in a similar manner to that described below for a catheter having a pressure sensor and/or IVUS transducer that is fastened to another catheter.

Use of the ultrasound imaging system can allow the operator to deliver the device without fluoroscopy or using less fluoroscopy, thereby reducing the radiation exposure to the patient, while allowing more accurate evaluation of the vasculature, aiding placement of the device and allowing confirmation that device placement was proper. The imaging can be used to aid in the deployment of the filters or other devices. The imaging can also be used to aid in the retrieval of the deployed devices by providing visualization of, for example, the retrieval features on the deployed device and of the retrieval features, such as loops on a snare, of the retrieval device. The vasculature and implant location can be imaged prior to deployment, after deployment and/or during deployment. The imaging can be used during the retrieval process. The imaging can be used to aid in positioning of the filter or device within the vasculature. The imaging can be used to image the deployment location and determine the appropriate sizing of the filter or other device. The imaging can be used to help estimate treatment duration.

Although imaging systems described above have been primarily described as ultrasound based, other imaging systems can be used instead or in addition. For example, the imaging system can be based on intravascular ultrasound (IVUS), Forward-Looking IVUS (FLIVUS), optical coherence tomography (OCT), piezoelectric micro-machined ultrasound traducer (PMUT), and/or FACT.

Other components can also be incorporated into the systems described herein. All or some of the device can be designed to increase their ability to adhere to the obstruction. For example, the wires may be coupled to an energy source (e.g., RF, ultrasonic, or thermal energy) to "weld" to the obstruction. Application of energy to the device can allow the surrounding portion to deform into the obstruction and "embed" within the obstruction. Alternatively, the device can impart a positive charge to the obstruction to partially liquefy the obstruction sufficiently to allow for easier removal. In another variation, a negative charge could be applied to further build thrombus and nest the device for better pulling force. The wires can be made stickier by use of a hydrophilic substance(s), or by chemicals that would generate a chemical bond to the surface of the obstruction. Alternatively, the filaments may reduce the temperature of the obstruction to congeal or adhere to the obstruction.

Another aspect applicable to variations of the devices can be to configure the devices (whether the traversing filament or the surrounding portion) for better adherence to the obstruction. One such mode includes the use of coatings that bond to certain clots (or other materials causing the obstruction.) For example, the wires may be coated with a hydrogel or adhesive that bonds to a thrombus. Accordingly, as the device secures about a clot, the combination of the additive and the mechanical structure of the device may improve the effectiveness of the device in removing the obstruction. Coatings may also be combined with the capturing portions or catheter to improve the ability of the device to encapsulate and remove the obstruction (e.g., a hydrophilic coating).

Such improvements may also be mechanical or structural. Any portion of the capturing portion can have hooks, fibers, or barbs that grip into the obstruction as the device surrounds the obstruction. The hooks, fibers, or barbs can be incorporated into any portion of the device. However, it will be important in some embodiments that such features do not hinder the ability of the practitioner to remove the device from the body.

In addition to additives, the device can be coupled to an RF, microwave, magnetic, thermal, cryo, or other power source, to allow electrical, current, ultrasound or RF energy to transmit through the device and induce clotting or cause additional coagulation of a clot or other obstruction.

The methods described herein may also include treating the obstruction prior to attempting to remove the obstruction. Such a treatment can include applying a chemical or pharmaceutical agent with the goal of making the occlusion shrink or to make it more rigid for easier removal. Such agents include, but are not limited to chemotherapy drugs, or solutions, lytic agents such as tPA, urokinase, or streptokinase for example, an anticoagulant, a mild formalin, or aldehyde solution.

Various other modifications, adaptations, and alternative designs are of course possible in light of the above teachings. Therefore, it should be understood at this time that the inventions may be practiced otherwise than as specifically described herein. It is contemplated that various combinations or subcombinations of the specific features and aspects of the embodiments disclosed above may be made and still fall within one or more of the inventions. Further, the disclosure herein of any particular feature, aspect, method, property, characteristic, quality, attribute, element, or the like in connection with an embodiment can be used in all other embodiments set forth herein. Accordingly, it should be understood that various features and aspects of the disclosed embodiments can be combined with or substituted for one another in order to form varying modes of the disclosed inventions. Thus, it is intended that the scope of the present inventions herein disclosed should not be limited by the particular disclosed embodiments described above. Moreover, while the inventions are susceptible to various modifications, and alternative forms, specific examples thereof have been shown in the drawings and are herein described in detail. It should be understood, however, that the inventions are not to be limited to the particular forms or methods disclosed, but to the contrary, the inventions are to cover all modifications, equivalents, and alternatives falling within the spirit and scope of the various embodiments described. Any methods disclosed herein need not be performed in the order recited. The methods disclosed herein include certain actions taken by a practitioner; however, they can also include any third-party instruction of those actions, either expressly or by implication. For example, actions such as "inserting a catheter transfemorally" includes "instructing the insertion of a catheter transfemorally." The ranges disclosed herein also encompass any and all overlap, subranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

What is claimed is:

1. A capture system comprising:
a tubular body comprising a first end, a second end, and an axial length therebetween, the first end having an opening and a capture guide;
one or more tensioners coupled to the capture guide,
wherein the tubular body has a first configuration in which the first end and the capture guide are expanded and the one or more tensioners are activated while the second end and a majority of the tubular body remains compressed and the tubular body has a first expanded axial length and a first width along the first expanded axial length,
wherein the one or more tensioners are configured to be deactivated while the capture guide is expanded,
wherein, when the one or more tensioners are activated, a tension of the one or more tensioners is adjustable between a plurality of predetermined tension levels,
wherein, when activated, the one or more tensioners are configured to limit or prevent deflection of the capture guide relative to when the one or more tensioners are deactivated,
wherein the tubular body is transformable to a second configuration in which the tubular body has a second expanded axial length greater than the first expanded axial length and the tubular body has a second width along the second expanded axial length; and
a funnel system comprising an expandable funnel tip and a shaft coupled to or continuous with the funnel tip, wherein the shaft and the funnel tip are configured to receive the tubular body,
a control handle defining a longitudinal slot and a plurality of lateral slots branching from the longitudinal slot, the control handle including a control member configured to move in the longitudinal slot to adjust the tension of the one or more tensioners, wherein the control member is configured to be positioned in the plurality of lateral slots,
wherein when the control member is positioned in a first lateral slot of the plurality of lateral slots, the one or more tensioners are configured to be deactivated while the capture guide is in a relatively low-profile delivery configuration, and
wherein when the control member is positioned in a second lateral slot of the plurality of lateral slots, the one or more tensioners are configured to remain deactivated while the capture guide is expanded.

2. The capture system of claim 1, wherein the capture guide forms the opening.

3. The capture system of claim 1, wherein the one or more tensioners extend proximally from the capture guide.

4. The capture system of claim 1, wherein the tubular body comprises a shape memory material.

5. The capture system of claim 1, wherein the second width of the tubular body along the second expanded axial length is substantially the same as the first width of the tubular body along the first expanded axial length.

6. The capture system of claim 1, wherein the one or more tensioners are equally spaced around a circumference of the capture guide.

7. The capture system of claim 1, wherein the one or more tensioners are unequally spaced around a circumference of the capture guide.

8. The capture system of claim 1, wherein the one or more tensioners are configured to apply tension to the capture guide such that the capture guide is rigid.

9. The capture system of claim 1, wherein the one or more tensioners comprise rods, tubes, coils, springs, wires, or laser cut elements.

10. The capture system of claim 1, wherein the one or more tensioners comprise one or more metallic wires.

11. The capture system of claim 1, wherein the one or more tensioners comprise one or more polymeric filaments.

12. The capture system of claim 1, wherein the capture guide comprises a shape memory material.

13. The capture system of claim 1, wherein the capture guide comprises a Nitinol loop.

14. The capture system of claim 1, wherein the capture guide is configured to conform to different vessel diameters and/or different geometric configurations.

15. The capture system of claim 1, wherein the one or more tensioners are configured to deactivate and remove tension to the capture guide such that the capture guide is not rigid.

16. The capture system of claim 1, wherein the funnel tip and the shaft are expandable.

17. The capture system of claim 1, wherein the one or more tensioners, when activated, are configured to hold the capture guide more rigid when the capture guide encounters material adhered to a vessel wall compared to when the one or more tensioners are deactivated.

18. The capture system of claim 1, wherein the control member is configured to move between a plurality of predetermined positions, wherein at least some positions of the plurality of predetermined positions correspond to respective tension levels of the plurality of predetermined tension levels.

19. The capture system of claim 1, wherein the predetermined tension levels include a first tension level, a second tension level higher than the first tension level, and a third tension level higher than the second tension level.

20. The capture system of claim 1, further comprising a first member comprising a central lumen, wherein the tubular body is configured to be received in the central lumen.

21. The capture system of claim 20, wherein the one or more tensioners are coupled to the first member.

22. The capture system of claim 20, wherein the one or more tensioners extend through the central lumen of the first member.

23. The capture system of claim 20, wherein the control handle is located at a proximal portion of the first member, wherein the one or more tensioners are coupled to the control handle.

24. The capture system of claim 23, wherein the control handle is configured to adjust the tension of the one or more tensioners.

25. The capture system of claim 20, further comprising a second member configured to be disposed within the central lumen, wherein the tubular body is coupled to the second member.

26. The capture system of claim 25, further comprising a guidewire lumen configured to receive a guidewire, wherein the capture system is configured to be introduced over the guidewire to a treatment site within a patient.

27. The capture system of claim 25, wherein the one or more tensioners are not coupled to the second member.

28. A capture system comprising:
a tubular body defining an axial length, the tubular body defining a proximal opening and including a capture guide at the proximal opening;
one or more tensioners coupled to the capture guide;
an inner shaft coupled to the tubular body;
an outer shaft defining a lumen configured to receive the inner shaft and the tubular body; and
a control handle comprising a control member configured to move between a plurality of predetermined positions to adjust a tension of the one or more tensioners,
wherein the one or more tensioners are configured to be deactivated while the capture guide is expanded and configured to be activated while the capture guide remains expanded,
wherein, when activated, the one or more tensioners are configured to limit or prevent deflection of the capture guide relative to when the one or more tensioners are deactivated,
wherein the tubular body has a first configuration in which a first end and the capture guide are expanded while a second end and a majority of the tubular body remains compressed and the tubular body has a first expanded axial length along the first expanded axial length, and
wherein the tubular body is transformable from the first configuration to a second configuration in which the tubular body has a second expanded axial length greater than the first expanded axial length,
wherein the control handle defines a longitudinal slot and a plurality of lateral slots branching from the longitudinal slot, wherein the control member is configured to move proximally and distally along the longitudinal slot, wherein the control member is configured to move laterally from the longitudinal slot to a first lateral slot of the plurality of lateral slots or a second lateral slot of the plurality of lateral slots, wherein each lateral slot of the plurality of lateral slots corresponds to a predetermined position of the plurality of predetermined positions, wherein when the control member is positioned in the first lateral slot, the one or more tensioners are configured to be deactivated while the capture guide is in a relatively low-profile delivery configuration, and wherein when the control member is positioned in the second lateral slot, the one or more tensioners are configured to remain deactivated while the capture guide is expanded.

29. The capture system of claim 28, wherein the one or more tensioners are not coupled to the inner shaft.

30. The capture system of claim 28, wherein the capture guide and the tubular body are configured to move between a low-profile configuration and an expanded configuration in response to movement of the control member.

* * * * *